(12) United States Patent
deLong et al.

(10) Patent No.: US 11,059,789 B2
(45) Date of Patent: Jul. 13, 2021

(54) ISOQUINOLINE-STEROID CONJUGATES AND USES THEREOF

(71) Applicant: Aerie Pharmaceuticals, Inc., Bedminster, NJ (US)

(72) Inventors: Mitchell A. deLong, Chapel Hill, NC (US); Eric Carlson, Irvine, CA (US); Casey Kopczynski, Chapel Hill, NC (US); Jill M. Sturdivant, Chapel Hill, NC (US); Cynthia Lichorowic, Raleigh, NC (US)

(73) Assignee: Aerie Pharmaceuticals, Inc., Bedminster, NJ (US)

( * ) Notice: Subject to any disclaimer, the term of this patent is extended or adjusted under 35 U.S.C. 154(b) by 0 days.

(21) Appl. No.: 16/557,779

(22) Filed: Aug. 30, 2019

(65) Prior Publication Data
US 2020/0071275 A1 Mar. 5, 2020

Related U.S. Application Data

(60) Provisional application No. 62/725,941, filed on Aug. 31, 2018.

(51) Int. Cl.
*C07D 217/22* (2006.01)
*A61K 47/28* (2006.01)
*A61K 9/00* (2006.01)

(52) U.S. Cl.
CPC ............ *C07D 217/22* (2013.01); *A61K 47/28* (2013.01); *A61K 9/0048* (2013.01)

(58) Field of Classification Search
CPC .................................................. C07D 217/22
USPC ......................................................... 546/113
See application file for complete search history.

(56) References Cited

U.S. PATENT DOCUMENTS

| 3,193,459 A | 7/1965 | Korman et al. |
| 8,450,344 B2 | 5/2013 | Delong et al. |
| 9,402,912 B2 | 8/2016 | Sinha et al. |
| 9,402,913 B2 | 8/2016 | Sinha et al. |
| 2015/0119419 A1 | 4/2015 | deLong et al. |

FOREIGN PATENT DOCUMENTS

WO 2010/127329 A1 11/2010

OTHER PUBLICATIONS

Levine J. Med. Chem. 2014, 57, 8224-8237.*
Venkatesh, J. Pharm. Sci. 89, 145-54 (2000) (p. 146, left column).*
J. G. Cannon, Chapter Nineteen in Burger's Medicinal Chemistry and Drug Discovery, Fifth Edition, vol. I: Principles and Practice, Wiley-Interscience 1995, pp. 783-802, 784.*
International Search Report and Written Opinion dated Nov. 15, 2019, for International Patent Application Serial No. PCT/US2019/049195 filed on Aug. 30, 2019.
PUBCHEM-CID: 656804, Created Jun. 24, 2005, pp. 1-20, "Prednisolone hemisuccinate."
International Patent Application Serial No. PCT/US2019/049195 filed on Aug. 30, 2019.

* cited by examiner

*Primary Examiner* — Nizal S Chandrakumar
(74) *Attorney, Agent, or Firm* — K&L Gates LLP; Louis C. Cullman; Benjamin D. Heuberger

(57) ABSTRACT

Provided herein are compounds and pharmaceutical compositions useful in modulating kinase activity, and related diseases. Also provided herein are methods of treating an eye disease or disorder in a subject. Also provided herein are methods of reducing intraocular pressure in a subject. Also provided herein are methods of modulating kinase activity in a cell. Also provided herein are methods of making the compounds provided herein, and compounds useful for the preparation of the compounds provided herein.

30 Claims, 6 Drawing Sheets

ISOQUINOLINE-STEROID CONJUGATES AND USES THEREOF

RELATED APPLICATIONS

This application claims priority of U.S. Provisional Patent Application No. 62/725,941, filed Aug. 31, 2018, the entire content of which is incorporated herein by reference.

BACKGROUND

Isoquinoline-steroid conjugates are provided herein.

A variety of hormones, neurotransmitters and biologically active substances control, regulate or adjust the functions of living bodies by way of specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs). The biological effects of activating or inhibiting these receptors is not direct, but is mediated by a host of intracellular proteins.

The importance of these secondary proteins has been recognized, and modulation of this class is now being investigated as intervention points in disease states. One of the most important classes of these downstream effectors is the "kinase" class. The various kinases have roles in the regulation of various physiological functions. For example, kinases have been implicated in a number of disease states.

Since the various kinases have roles in the regulation of various physiological functions and thereby have roles in many disease states, there is an urgent and continuing need for small molecule ligands which inhibit or modulate the activity of kinases. Without wishing to be bound by theory, it is thought that modulation of the activity of kinases, in particular ROCK and JAK kinases, by the compounds of the present disclosure is, at least in part, responsible for their beneficial effects.

Ocular inflammatory diseases or disorders, such as uveitis, an infectious corneal ulcer, endophthalmitis, an autoimmune disease of the cornea or ocular surface, or an ophthalmic manifestation of HIV disease, can slightly reduce vision or lead to severe vision loss or blindness. "Uveitis" is a general term describing a group of inflammatory diseases that produces swelling and destroys eye tissues. The term "uveitis" is used because the diseases often affect a part of the eye called the uvea. Nevertheless, uveitis is not limited to the uvea. These diseases also affect the lens, retina, optic nerve, and vitreous, producing reduced vision or blindness. Uveitis may be caused by diseases or disorders occurring in the eye or it can be part of an inflammatory disease affecting other parts of the body. Eye care professionals may describe such a disease or disorder more specifically as anterior uveitis, intermediate uveitis, posterior uveitis, or panuveitis uveitis.

To treat an ocular inflammatory disease or disorder, an eye care professional may prescribe steroidal anti-inflammatory medication. Examples of such steroidal anti-inflammatory medication that can be used to treat an ocular inflammatory disease include, but are not limited to prednisone (sold under many brand names, such as DELTASONE and STERAPRED), methylprednisolone (MEDROL), prednisolone (PRELONE, PEDIAPRED), dexamethasone (DECADRON, HEXADROL), and hydrocortisone (ACTICORT, CORTEF).

Unfortunately, use of steroidal anti-inflammatory medication may cause deleterious side effects, such as increasing intraocular pressure (e.g. a rise above 20 mmHg from baseline). This side effect may result in glaucoma, or if the patient already suffers from glaucoma, it may further aggravate the patient's condition. In addition, at higher doses cataracts are possible with steroids. Further, many steroids have limited water solubility, which further limits their usefulness.

Consequently, what is needed is a treatment for disease or disorder associated with kinase activity.

What is also needed is a treatment for an ocular inflammatory disease or disorder that does not increase intraocular pressure.

What is also needed is a treatment that reduces intraocular pressure. Such a treatment would have applications in treating an eye disease or disorder.

SUMMARY

In one aspect, provided herein are compounds of Formula (I):

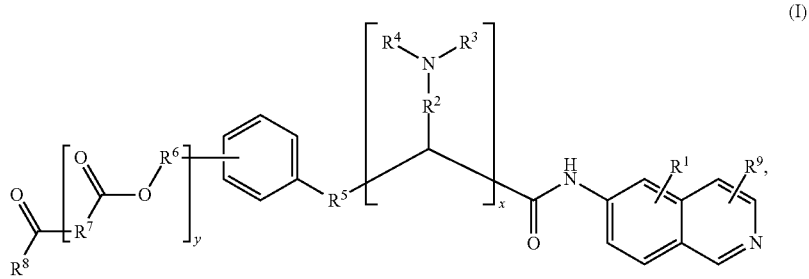

or a pharmaceutically acceptable salt thereof;
wherein
$R^1$ is H, —$C_{1-3}$ alkyl, —$C_{1-3}$ haloalkyl, or halogen;
$R^2$ is $C_{1-3}$ alkylene or $C_{1-3}$ haloalkylene;
$R^3$ is H, —$C_{1-6}$ alkyl, or —$C_{1-6}$ haloalkyl;
$R^4$ is H, —$C_{1-6}$ alkyl, or —$C_{1-6}$ haloalkyl;
$R^5$ is a bond or

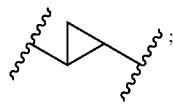 [SMILES: *C1CC1*]

$R^6$ is $C_{1-6}$ alkylene or $C_{1-6}$ haloalkylene;

$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;

$R^8$ is a steroidal moiety, wherein $R^8$ and the carbonyl to which it is attached form an ester linkage;

$R^9$ is H, —$C_{1-3}$ alkyl, —$C_{1-3}$ haloalkyl, or halogen;

x is 0 or 1; and y is 0 or 1.

In another aspect, provided herein are compounds of Formula (Ia):

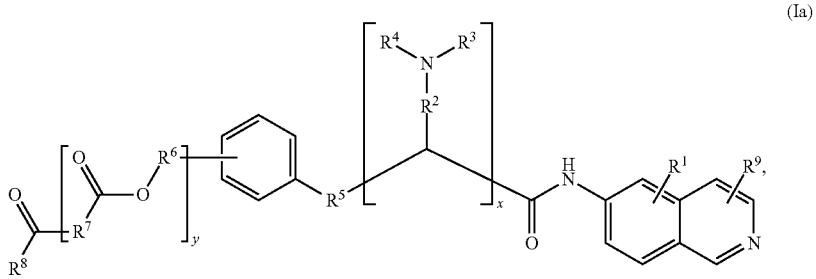

(Ia)

or a pharmaceutically acceptable salt thereof;
wherein $R^1$ is H, —$C_{1-3}$ alkyl, —$C_{1-3}$ haloalkyl, or halogen;

$R^2$ is a bond, $C_{1-3}$ alkylene or $C_{1-3}$ haloalkylene;

$R^3$ is H, —$C_{1-6}$ alkyl, or —$C_{1-6}$ haloalkyl;

$R^4$ is H, —$C_{1-6}$ alkyl, or —$C_{1-6}$ haloalkyl;

$R^5$ is a bond or

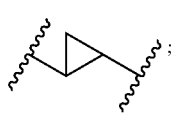 [SMILES: *C1CC1*];

$R^6$ is $C_{1-6}$ alkylene or $C_{1-6}$ haloalkylene;

$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;

$R^8$ is a steroidal moiety, wherein $R^8$ and the carbonyl to which it is attached form an ester linkage;

$R^9$ is H, —$C_{1-3}$ alkyl, —$C_{1-3}$ haloalkyl, halogen, —CN, —($C_{1-10}$ alkylene)-CN, or —($C_{1-10}$ alkylene)-OH;

x is 0 or 1; and y is 0 or 1.

In another aspect, provided herein are compounds of Formula (XI):

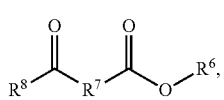

(XI)

or a pharmaceutically acceptable salt thereof;
wherein $R^6$ is H, $C_{1-6}$ haloalkyl or $C_{1-6}$ alkyl;

$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl; and $R^8$ is a steroidal moiety, wherein $R^8$ and the carbonyl to which it is attached form an ester linkage.

In another aspect, provided herein are compounds of Formula (XII):

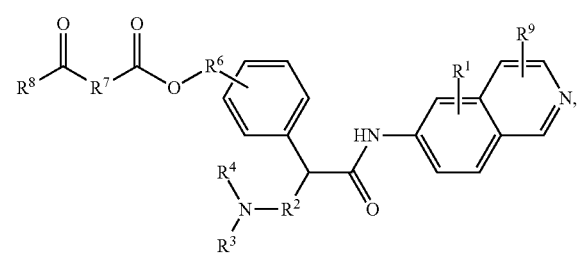

(XII)

or a pharmaceutically acceptable salt thereof;
wherein $R^1$ is H, —$C_{1-3}$ alkyl, —$C_{1-3}$ haloalkyl, or halogen;

$R^2$ is $C_{1-3}$ alkylene or $C_{1-3}$ haloalkylene;

$R^3$ is an acid-labile protecting group;

$R^4$ is H, —$C_{1-6}$ alkyl, or —$C_{1-6}$ haloalkyl;

$R^6$ is $C_{1-6}$ alkylene or $C_{1-6}$ haloalkylene;

$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;

$R^8$ is a steroidal moiety, wherein $R^8$ and the carbonyl to which it is attached form an ester linkage; and $R^9$ is H, —$C_{1-3}$ alkyl, —$C_{1-3}$ haloalkyl, or halogen.

In another aspect, provided herein are compounds of Formula (XII):

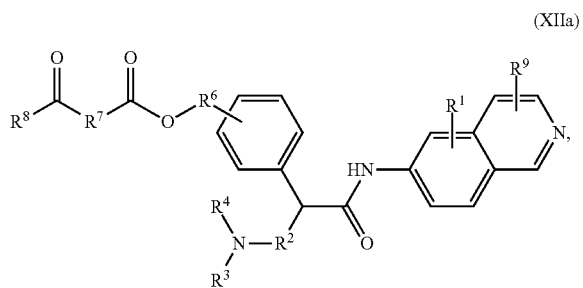

(XIIa)

or a pharmaceutically acceptable salt thereof;
wherein
$R^1$ is H, —$C_{1-3}$ alkyl, —$C_{1-3}$ haloalkyl, or halogen;
$R^2$ is a bond, $C_{1-3}$ alkylene or $C_{1-3}$ haloalkylene;
$R^3$ is an acid-labile protecting group;
$R^4$ is H, —$C_{1-6}$ alkyl, or —$C_{1-6}$ haloalkyl;
$R^6$ is $C_{1-6}$ alkylene or $C_{1-6}$ haloalkylene;
$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;
$R^8$ is a steroidal moiety, wherein $R^8$ and the carbonyl to which it is attached form an ester linkage; and
$R^9$ is H, —$C_{1-3}$ alkyl, —$C_{1-3}$ haloalkyl, halogen, —CN, —($C_{1-10}$ alkylene)-CN, or —($C_{1-10}$ alkylene)-OH.

In another aspect, provided herein are methods of preparing a compound of Formula (X):

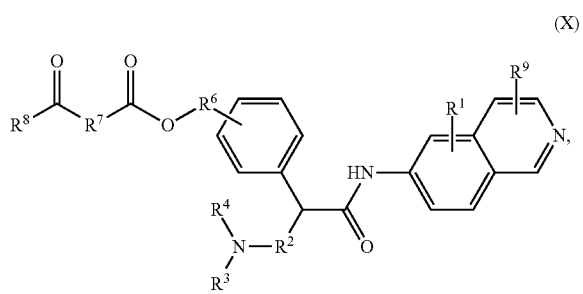

(X)

or a pharmaceutically acceptable salt thereof,
wherein
$R^1$ is H, —$C_{1-3}$ alkyl, —$C_{1-3}$ haloalkyl, or halogen;
$R^2$ is $C_{1-3}$ alkylene or $C_{1-3}$ haloalkylene;
$R^3$ is H, —$C_{1-6}$ alkyl, or —$C_{1-6}$ haloalkyl;
$R^4$ is H;
$R^6$ is $C_{1-6}$ alkylene or $C_{1-6}$ haloalkylene;
$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;
$R^8$ is a steroidal moiety, wherein $R^8$ and the carbonyl to which it is attached form an ester linkage; and
$R^9$ is H, —$C_{1-3}$ alkyl, —$C_{1-3}$ haloalkyl, or halogen;
comprising contacting a compound of Formula (XII) with an acid such that the compound of Formula (X) is formed.

In another aspect, provided herein are methods of preparing a compound of Formula (X):

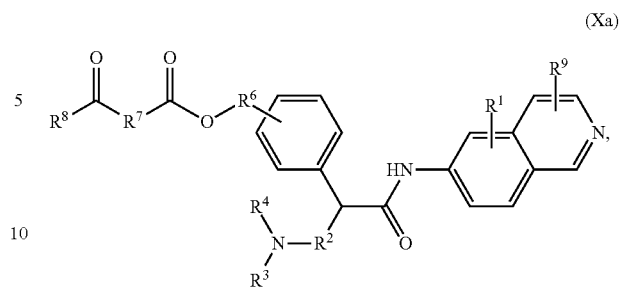

(Xa)

or a pharmaceutically acceptable salt thereof,
wherein
$R^1$ is H, —$C_{1-3}$ alkyl, —$C_{1-3}$ haloalkyl, or halogen;
$R^2$ is a bond, $C_{1-3}$ alkylene or $C_{1-3}$ haloalkylene;
$R^3$ is H, —$C_{1-6}$ alkyl, or —$C_{1-6}$ haloalkyl;
$R^4$ is H;
$R^6$ is $C_{1-6}$ alkylene or $C_{1-6}$ haloalkylene;
$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;
$R^8$ is a steroidal moiety, wherein $R^8$ and the carbonyl to which it is attached form an ester linkage; and
$R^9$ is H, —$C_{1-3}$ alkyl, —$C_{1-3}$ haloalkyl, halogen, —CN, —($C_{1-10}$ alkylene)-CN, or —($C_{1-10}$ alkylene)-OH;
comprising contacting a compound of Formula (XII) with an acid such that the compound of Formula (X) is formed.

In another aspect, provided herein are methods of treating an eye disease or disorder in a subject in need thereof, comprising administering to the subject an effective amount of a compound or composition provided herein.

In another aspect, provided herein are methods of reducing intraocular pressure in an eye of a subject in need thereof, comprising administering to the subject an effective amount of a compound or composition provided herein.

In another aspect, provided herein are methods of modulating kinase activity in a cell, comprising contacting the cell with an amount of a compound or composition provided herein effective to modulate kinase activity.

In another aspect, provided herein are methods of treating an ocular inflammatory disease or disorder in a subject in need thereof, comprising administering to the subject an effective amount of a compound or composition provided herein. In a particular embodiment of such a method, intraocular pressure is not increased. In even more particular embodiments of such a method, intraocular pressure is maintained at physiological intraocular pressure, or reduced.

DETAILED DESCRIPTION

Figure 1:
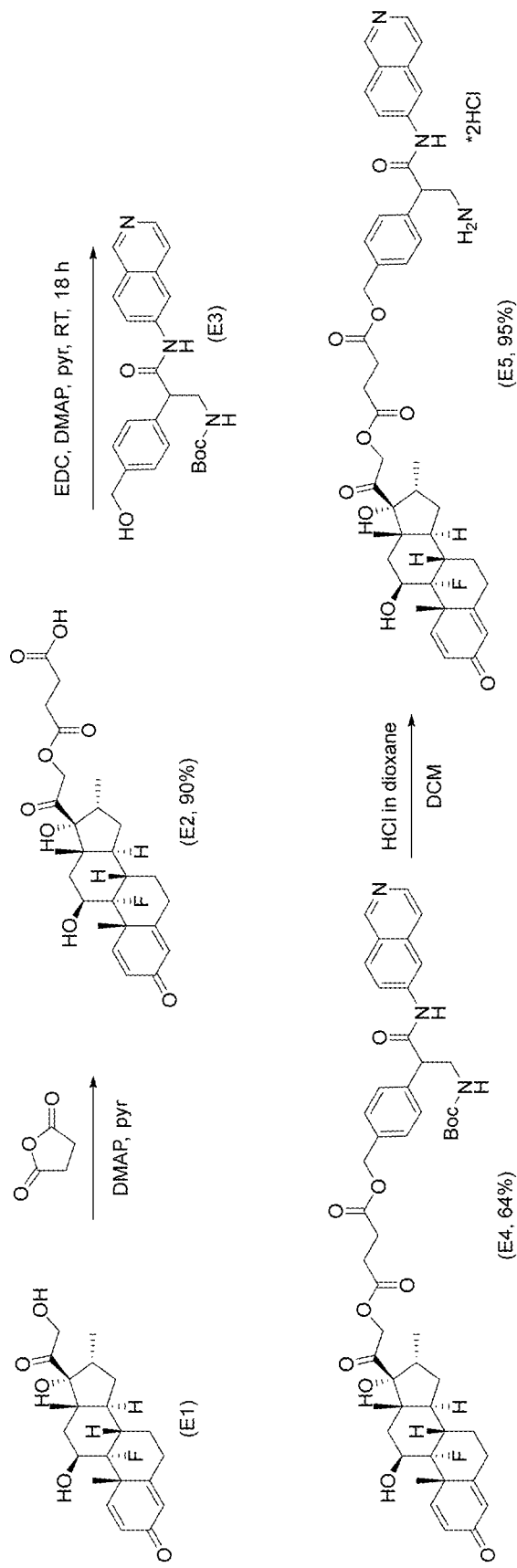
FIG. 1 shows a synthetic scheme for the synthesis of 4-(3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate dihydrochloride (E5 2HCl).

Listed below are definitions of various terms used to describe the present disclosure. These definitions apply to the terms as they are used throughout this specification and claims, unless otherwise limited in specific instances, either individually or as part of a larger group.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by one of ordinary skill in the art and will vary to some extent on the context in which it is used. As used herein when referring to a measurable value such as an amount, a temporal duration, and the like, the term "about" is meant to encompass variations of ±20% or ±10%, including ±5%, ±1%, and ±0.1% from the specified value, as such variations are appropriate to perform the disclosed methods.

As used herein, the term "administering" refers to administration of the compounds provided herein to a cell or a subject as needed to achieve the desired effect.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. In some embodiments the alkyl is $C_{1-6}$ alkyl, such as ethyl, methyl, isopropyl, isobutyl, n-pentyl, n-hexyl, or cyclopropylmethyl.

As used herein, the term "alkylene" by itself or as part of another substituent means, unless otherwise stated, a divalent alkyl.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. In some embodiments, the aryl is phenyl or naphthyl. In some embodiments, the aryl is phenyl.

As used herein, the terms "composition" or "pharmaceutical composition" refer to a mixture of at least one compound—useful as described herein—with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary, and topical administration.

As used herein, the term "contacting a cell" refers to contacting a cell in vitro or in vivo, i.e. in a subject, such as a mammal, including humans, livestock, rabbits, cats, dogs, and mice.

As used herein, the term "controlling the disease or disorder" is used to mean changing the activity of one or more kinases to affect the disease or disorder.

As used herein, the term "cycloalkyl" refers to a mono cyclic or polycyclic nonaromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle, which contains at least one carbon-carbon double bond or one carbon-carbon triple bond.

As used herein, the term "disease or disorder associated with kinase activity" refers to a disease, condition or disorder treatable, in whole or in part, by inhibition of one or more kinases.

As used herein, the terms "effective amount," "pharmaceutically effective amount" and "therapeutically effective amount" refer to a nontoxic but sufficient dosage amount of an agent (e.g., the compounds or compositions provided herein) to provide the desired biological result, which result may be reduction or alleviation, or both, of the signs, symptoms, or causes of a disease, or any other desired alteration of a biological system including influencing, reducing or inhibiting the activity of or preventing activation of a kinase (e.g., modulating kinase activity). An appropriate therapeutic amount in any individual case may be determined by one of ordinary skill in the art using routine experimentation. These terms as used herein may also refer to an amount effective at bringing about a desired in vivo effect in an animal—where in some embodiments, the animal is a human—including, but not limited to, uveitis, reduction in intraocular pressure, or dry eye.

As used herein, the term "excipient" refers to physiologically compatible additives useful in preparation of a pharmaceutical composition. Examples of pharmaceutically acceptable carriers and excipients can, for example, be found in Remington Pharmaceutical Science, $16^{th}$ Ed.

As used herein, the term "eye disease or disorder" refers to, but is not limited to, glaucoma, allergy, cancers of the eye, neurodegenerative diseases or disorders of the eye, such as diabetic eye disease, macular degeneration (AMD), an ocular inflammatory disease or disorder, and dry eye.

As used herein, a "glucocorticoid response element" is one that responds to the presence of corticosteroids by facilitating new transcription.

As used herein, a negative side effect is one that causes a doctor or medical professional to stop or consider stopping, the use of the steroid prematurely to prevent ocular damage that might arise from the continued use thereof. A non-limiting example is the ocular hypertension that often occurs with long-term steroid use.

As used herein, the term "ocular inflammatory disease or disorder" refers to, but is not limited to uveitis, a corneal ulcer, endophthalmitis, an autoimmune disease of the cornea or ocular surface, an ophthalmic manifestation of HIV disease, or any combination thereof.

As used herein, the term "halo" or "halogen" alone or as part of another substituent (e.g., haloalkyl, haloalkylene, haloaryl, halocycloalkyl, and the like) means, unless otherwise stated, a fluorine, chlorine, bromine, or iodine atom. In some embodiments, the halo or halogen is fluorine, chlorine, or bromine. In some embodiments, the halo or halogen is fluorine or chlorine. When used as part of another substituent, examples may include more than one halogen (e.g., 2, 3, 4, 5, 6, 7, 8, 9, 10, or 11 or more halogens) wherein each halogen is independently fluorine, chlorine, bromine, or iodine.

As used herein, the terms "subject," "patient" or "individual" refer to a human or a non-human mammal. Non-human mammals include, for example, livestock and pets, such as ovine, bovine, porcine, canine, feline, and murine mammals. In some embodiments, the patient, subject, or individual is human.

As used herein, the term "pharmaceutically acceptable" refers to a material that does not abrogate the biological activity or properties of the compound, and is relatively non-toxic, i.e. the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The term "pharmaceutically acceptable carrier" may further include a pharmaceutically acceptable salt of the compound useful within the invention. Other additional ingredients that may be included in the pharmaceutical compositions used in the practice of the invention are described, for example, in Remington's Pharmaceutical Sciences (Genaro, Ed., Mack Publishing Co., 1985, Easton, Pa.), which is incorporated herein by reference. The "pharmaceutically acceptable carrier" is useful for the preparation of a pharmaceutical composition that is: generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal or oral administration. "Pharmaceutically acceptable carrier" also includes agents for preparation of aqueous dispersions and sterile powders for injection or dispersions.

As used herein, the term "pharmaceutically acceptable salt" refers to derivatives of the compounds provided herein wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by combining the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile may be used. Lists of suitable salts are found in Remington's Pharmaceutical Sciences, $17^{th}$ ed., Mack Publishing Company, Easton, Pa., 1985, p. 1418 and Journal of Pharmaceutical Science, 66, 2 (1977), each of which is incorporated herein by reference in its entirety.

As used herein, the terms "prevent" or "prevention" refer to no disorder or disease development if none had occurred, or no further disorder or disease development if there had already been development of the disorder or disease. Also considered is the ability of one to prevent some or all of the symptoms associated with the disorder or disease.

As used herein, a "proinflammatory transcription factor" is a factor that causes the transcription of a proinflammatory protein (e.g., a proinflammatory cytokine such as IL-6).

As used herein, the term "protecting group" refers to a chemical moiety used to control the reactivity of a chemical functional group that is attached to a parent molecule while the parent molecule is involved in a multi-step synthetic procedure. Protecting groups may be sensitive to specific chemical environments, wherein the protecting group will cleave upon exposure to the chemical environment thereby producing the chemical functional group of the parent molecule. For example, exposure of a parent molecule comprising an amine—that is protected with an acid-labile protecting group—to an acidic environment will cleave the acid-labile protecting group and produce a molecule comprising an amine (i.e. an unprotected amine, i.e. a primary amine or a secondary amine). Protecting groups are described in Greene and Wuts, Protective Groups in Organic Synthesis $3^{rd}$ Ed., (Wiley 1999), which is incorporated herein by reference. Examples of acid-labile protecting groups include, but are not limited to, t-butyloxycarbonyl (Boc), benzyloxycarbonyl (Cbz), o-chlorobenzyloxycarbonyl, biphenylisopropyloxycarbonyl, t-amyloxycarbonyl (Amoc), isobornyloxycarbonyl, α,α-dimethyl-3,5-dimethoxybenzyloxy-carbonyl, o-nitrophenylsulfenyl, 2-cyano-t- butoxycarbonyl, 9-fluorenyl-methoxycarbonyl (Fmoc) and the like. In some embodiments, the acid-labile protecting group is Boc or Fmoc.

As used herein, "transactivation" refers to the activation of transcription.

As used herein, "transrepression" refers to the inhibition of translation.

As used herein, the terms "treatment" or "treating" refer to the application or administration of a therapeutic agent, i.e. a compound provided herein, to a patient, or application or administration of a therapeutic agent to an isolated tissue or cell line from a patient (e.g., for diagnosis or ex vivo applications), who has a disease, a symptom of the disease or the potential to develop the disease, with the purpose to heal, alleviate, relieve, alter, remedy, ameliorate, improve or affect the disease, the symptoms of the disease, or the potential to develop the disease. Such treatments may be specifically tailored or modified, based on knowledge obtained from the field of pharmacogenomics.

As used herein, the term "physiological intraocular pressure" refers to the intraocular pressure found in individuals not suffering from a disease or disorder that increases intraocular pressure, such as glaucoma. For most of the population, physiological intraocular pressure ranges between about 10 mm Hg and about 21 mm Hg, inclusive.

Compounds

In one aspect, provided herein are compounds of Formula (I):

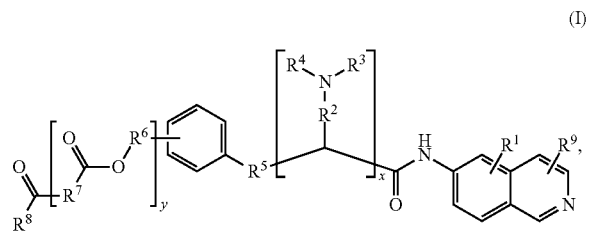

(I)

or a pharmaceutically acceptable salt thereof;
wherein
$R^1$ is H, —$C_{1-3}$ alkyl, —$C_{1-3}$ haloalkyl, or halogen;
$R^2$ is $C_{1-3}$ alkylene or $C_{1-3}$ haloalkylene;
$R^3$ is H, —$C_{1-6}$ alkyl, or —$C_{1-6}$ haloalkyl;
$R^4$ is H, —$C_{1-6}$ alkyl, or —$C_{1-6}$ haloalkyl;
$R^5$ is a bond or

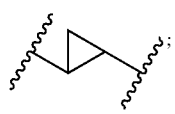 [SMILES: *C1CC1*]

$R^6$ is $C_{1-6}$ alkylene or $C_{1-6}$ haloalkylene;
$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;
$R^8$ is a steroidal moiety, wherein $R^8$ and the carbonyl to which it is attached form an ester linkage;

$R^9$ is H, —$C_{1-3}$ alkyl, —$C_{1-3}$ haloalkyl, or halogen;
x is 0 or 1; and
y is 0 or 1.

In some embodiments, Formula (I) is of Formula (II):

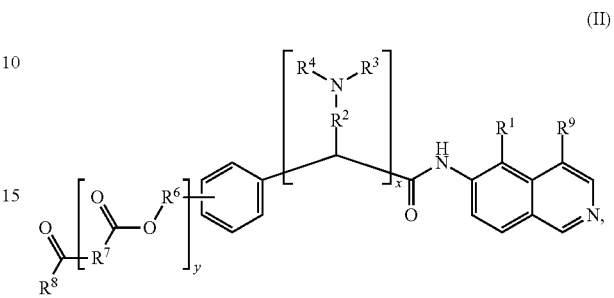

(II)

or a pharmaceutically acceptable salt thereof.

In some embodiments, Formula (I) is of Formula (V):

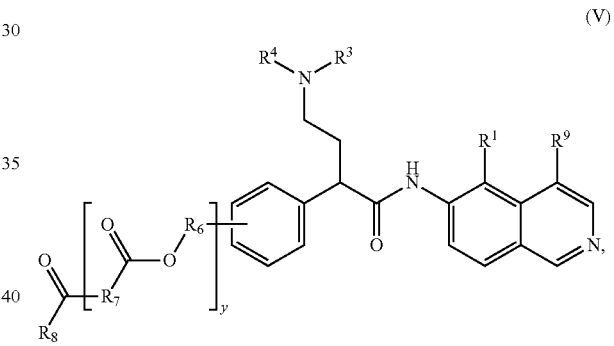

(V)

or a pharmaceutically acceptable salt thereof.

In some embodiments, Formula (I) is of Formula (VI):

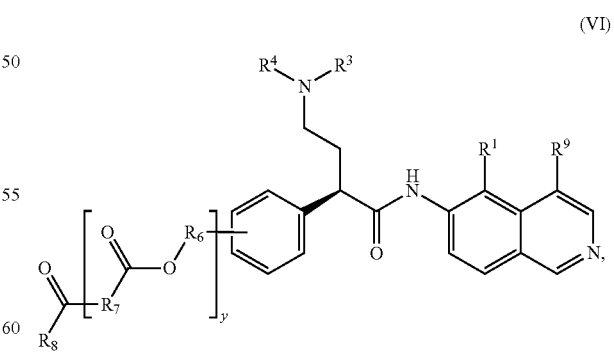

(VI)

or a pharmaceutically acceptable salt thereof.

In some embodiments, Formula (I) is of Formula (VII):

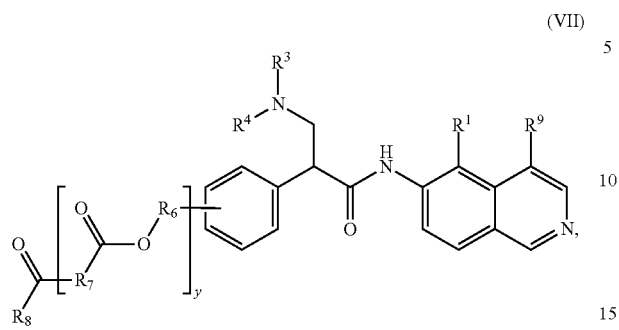

(VII)

or a pharmaceutically acceptable salt thereof.
In some embodiments, Formula (I) is of Formula (VIII):

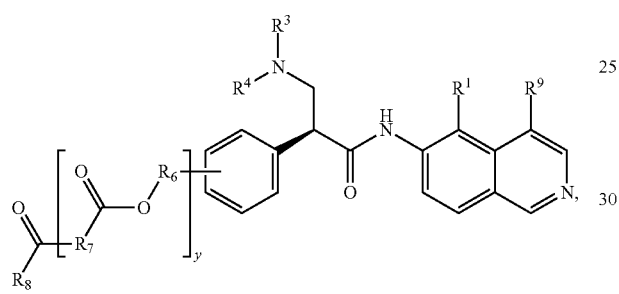

(VIII)

or a pharmaceutically acceptable salt thereof.
In some embodiments, Formula (I) is of Formula (IX):

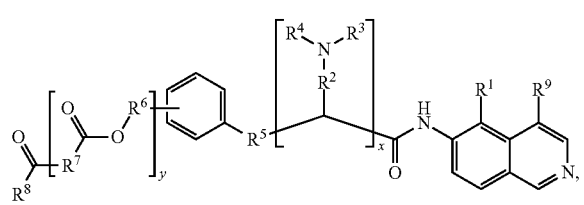

(IX)

or a pharmaceutically acceptable salt thereof.
In some embodiments, Formula (I) is of Formula (X):

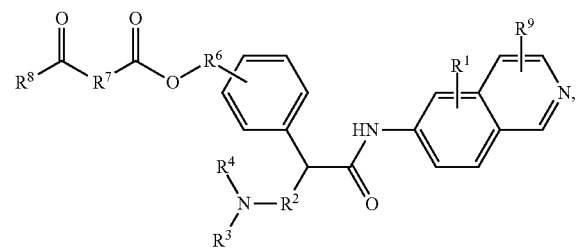

(X)

or a pharmaceutically acceptable salt thereof.

In some embodiments, Formula (I) is of Formula (III):

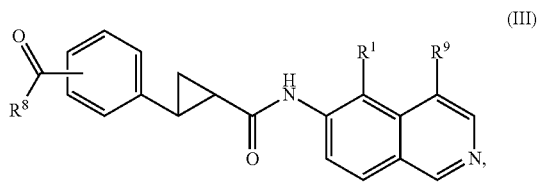

(III)

or a pharmaceutically acceptable salt thereof.
In some embodiments, Formula (I) is of Formula (IV):

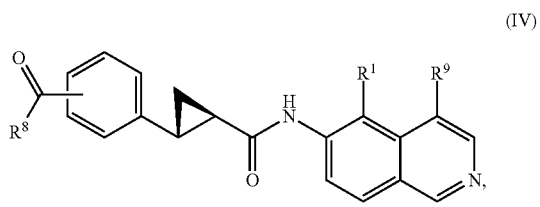

(IV)

or a pharmaceutically acceptable salt thereof.
In another aspect, provided herein are compounds of Formula (XI):

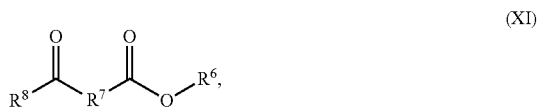

(XI)

or a pharmaceutically acceptable salt thereof;
wherein
$R^6$ is H, $C_{1-6}$ haloalkyl or $C_{1-6}$ alkyl;
$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl; and
$R^8$ is a steroidal moiety, wherein $R^8$ and the carbonyl to which it is attached form an ester linkage.

In another aspect, provided herein are compounds of Formula (XII):

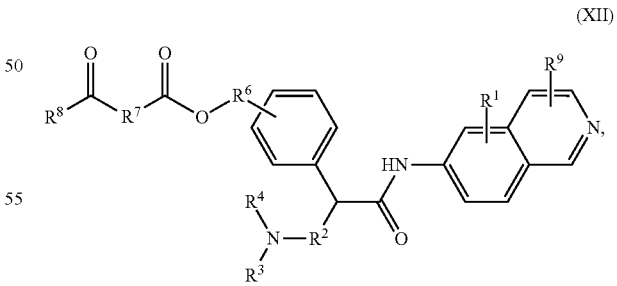

(XII)

or a pharmaceutically acceptable salt thereof;
wherein
$R^1$ is H, —$C_{1-3}$ alkyl, —$C_{1-3}$ haloalkyl, or halogen;
$R^2$ is $C_{1-3}$ alkylene or $C_{1-3}$ haloalkylene;
$R^3$ is an acid-labile protecting group;
$R^4$ is H, —$C_{1-6}$ alkyl, or —$C_{1-6}$ haloalkyl;
$R^6$ is $C_{1-6}$ alkylene or $C_{1-6}$ haloalkylene;

$R^7$ is $C_{1-10}$ alkylene, $C_{1-10}$ haloalkylene, $C_{1-10}$ alkylene substituted with —$NH_2$, $C_{6-10}$ aryl, $C_{6-10}$ haloaryl, $C_{3-8}$ cycloalkyl, or $C_{3-8}$ halocycloalkyl;

$R^8$ is a steroidal moiety, wherein $R^8$ and the carbonyl to which it is attached form an ester linkage; and $R^9$ is H, —$C_{1-3}$ alkyl, —$C_{1-3}$ haloalkyl, or halogen.

In some embodiments of the Formulae provided herein, $R^3$, together with the nitrogen to which it is attached, forms a carbamate.

In some embodiments, $R^3$ is —C(O)O—$C_{1-6}$ alkyl, —C(O)O—$C_{1-6}$ haloalkyl, —C(O)O— benzyl, or —C(O)O-halobenzyl.

In some embodiments, $R^6$ is H, $C_{04}$ haloalkyl or $C_4$ alkyl.

In some embodiments:
$R^1$ is H, methyl, F, Cl, Br, or I;
$R^2$ is $C_{1-3}$ alkylene;
$R^3$ is H or —$C_{1-6}$ alkyl;
$R^4$ is H or —$C_{1-6}$ alkyl;
$R^6$ is $C_{1-6}$ alkylene;
$R^7$ is $C_{1-10}$ alkylene, $C_{1-10}$ alkylene substituted with —$NH_2$, phenylene,

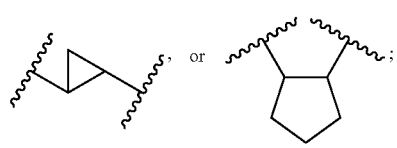 [SMILES: *C1CC1* ; *C1CCCC1*]

and
$R^9$ is H, methyl, F, Cl, Br, or I.

In some embodiments, $R^1$ is H, methyl, F, or Cl, and $R^9$ is H, methyl, F, or Cl.

In some embodiments, $R^1$ is H or F, and $R^9$ is H.

In some embodiments:
$R^1$ is H, and $R^9$ is H, —$C_{1-3}$ alkyl, —$C_{1-3}$ haloalkyl, or halogen; or
$R^1$ is H, —$C_{1-3}$ alkyl, —$C_{1-3}$ haloalkyl, or halogen, and $R^9$ is H.

In some embodiments:
$R^1$ is H, and $R^9$ is —$C_{1-3}$ alkyl, —$C_{1-3}$ haloalkyl, or halogen; or
$R^1$ is —$C_{1-3}$ alkyl, —$C_{1-3}$ haloalkyl, or halogen, and $R^9$ is H.

In some embodiments, $R^2$ is methylene or ethylene.
In some embodiments, $R^2$ is a bond.
In some embodiments, $R^3$ and $R^4$ are H.
In some embodiments, $R^3$ and $R^4$ are H, methyl, or ethyl.
In some embodiments, $R^3$ and $R^4$ are, independently, H, methyl, or ethyl.
In some embodiments, $R^5$ is

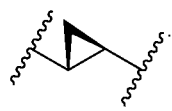 [SMILES: *[C@@H]1C[C@H]1*]

In some embodiments, $R^6$ is $C_{1-3}$ alkylene.
In some embodiments, $R^7$ is $C_{1-3}$ alkylene, $C_{1-3}$ alkylene substituted with —$NH_2$, phenylene, or $C_{3-6}$ cycloalkyl.
In some embodiments, $R^7$ is $C_{1-3}$ alkylene, $C_{1-3}$ alkylene substituted with —$NH_2$,

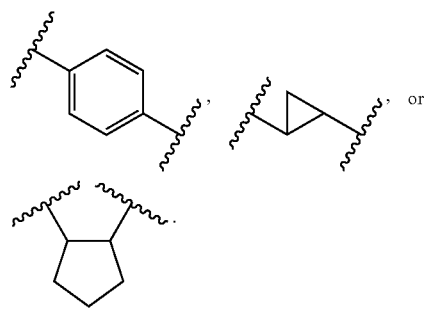 [SMILES: *c1ccc(*)cc1 ; *C1CC1* ; *C1CCCC1*]

In some embodiments, $R^6$ and $R^7$ are, independently, methylene or ethylene.

In some embodiments, $R^8$ is a corticosteroidal moiety or a derivative thereof. In some embodiments, $R^8$ is a glucocorticoidyl moiety or a derivative thereof. In some embodiments, $R^8$ is a mineralocorticoidyl moiety or a derivative thereof.

In some embodiments, $R^8$ is dexamethasonyl, prednisolonyl, fluocinolonyl, or triamcinolonyl.

In some embodiments, $R^8$ is prednisonyl, hydrocortisonyl, cortisonyl, dexamethasonyl, prednisolonyl, fluocinolonyl, or triamcinolonyl.

In some embodiments, $R^8$ is

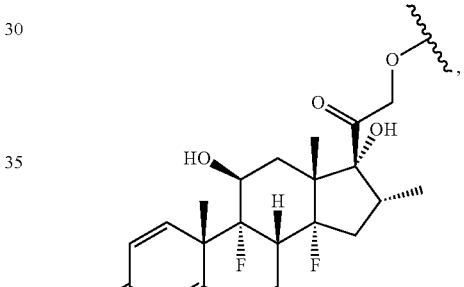

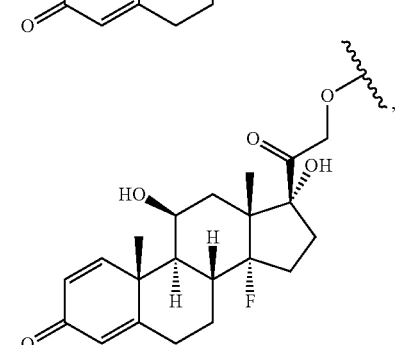

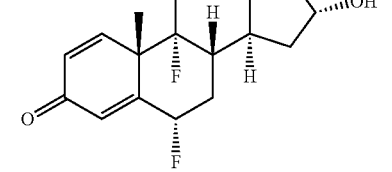

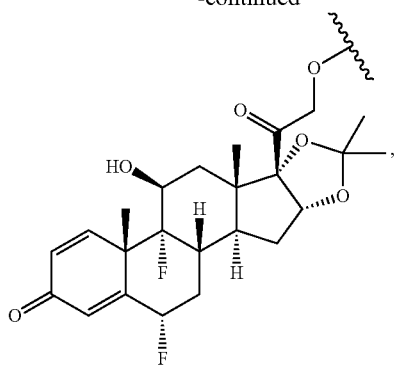
,
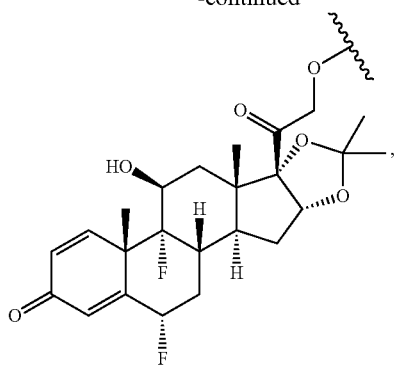 or
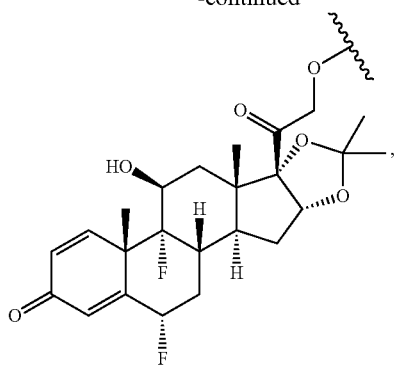.
In some embodiments, $R^8$ is
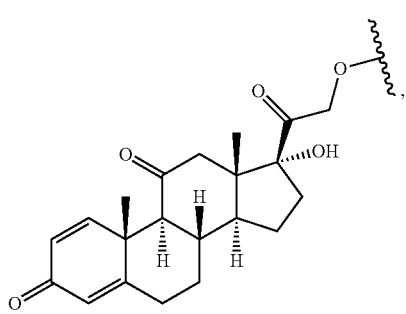,
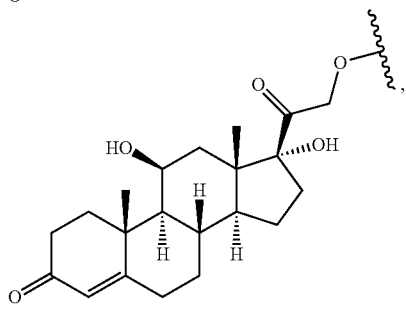,
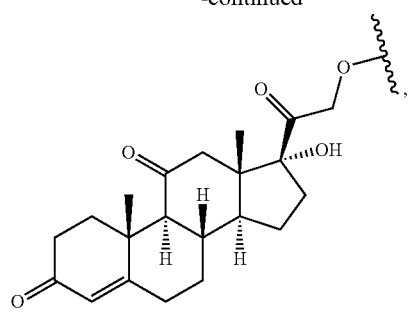,
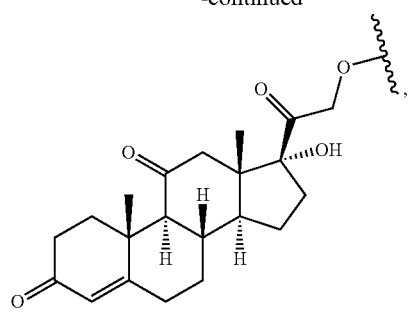,
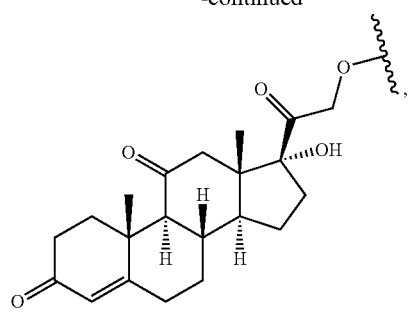,
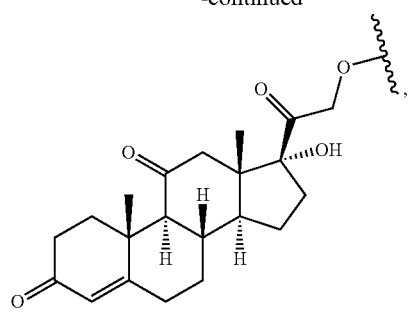,
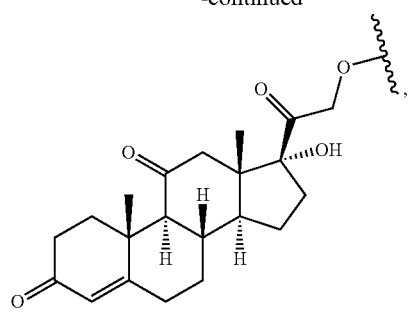,

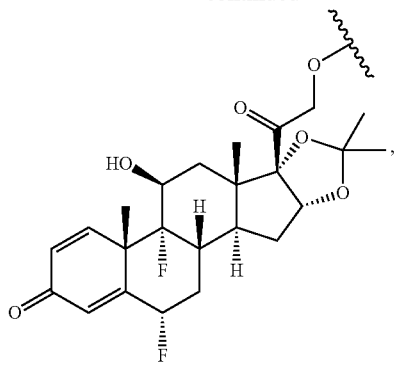

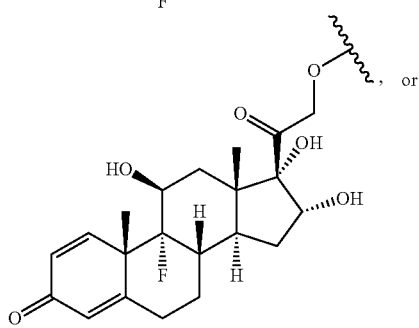

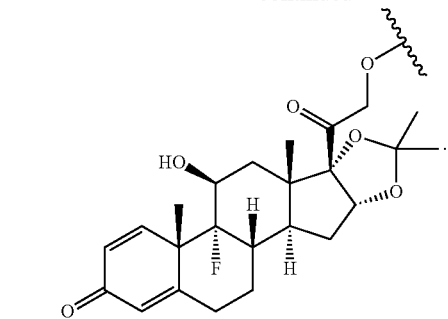

In some embodiments, $R^9$ is —$C_{1-3}$ alkyl, —$C_{1-3}$ haloalkyl, halogen, —CN, —($C_{1-10}$ alkylene)-CN, or —($C_{1-10}$ alkylene)-OH.

In some embodiments, $R^9$ is H, —$C_{1-3}$ alkyl, —$C_{1-3}$ haloalkyl, halogen, —CN, —($C_{1-3}$ alkylene)-CN, or —($C_{1-3}$ alkylene)-OH.

In some embodiments, $R^9$ is —$C_{1-3}$ alkyl, —$C_{1-3}$ haloalkyl, halogen, —CN, —($C_{1-3}$ alkylene)-CN, or —($C_{1-3}$ alkylene)-OH.

In some embodiments, $R^9$ is —CN, —($C_{1-3}$ alkylene)-CN, or —($C_{1-3}$ alkylene)-OH.

In some embodiments, the compound is:

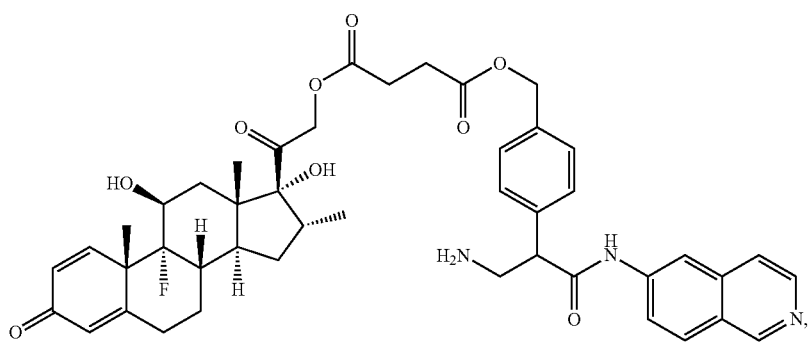

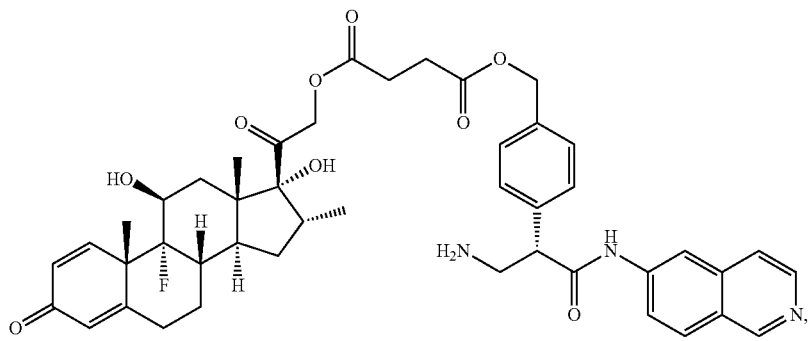

-continued
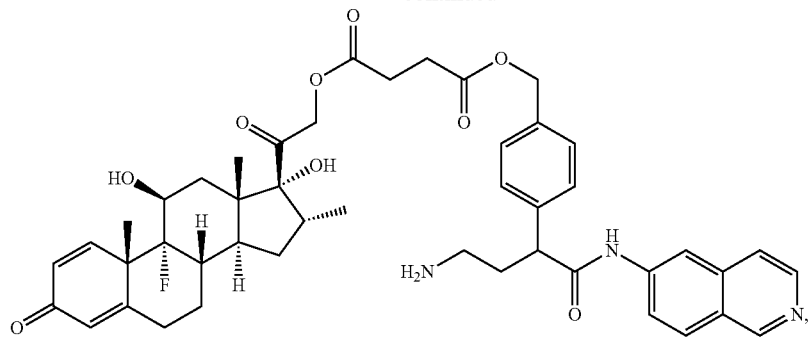
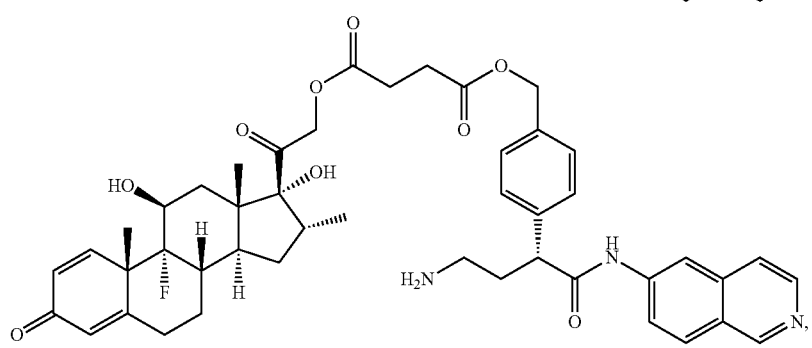
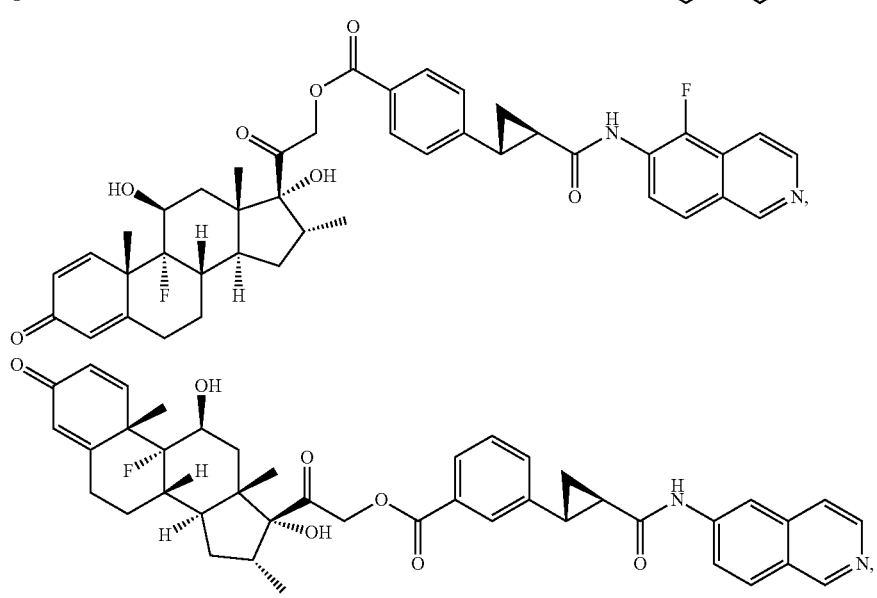
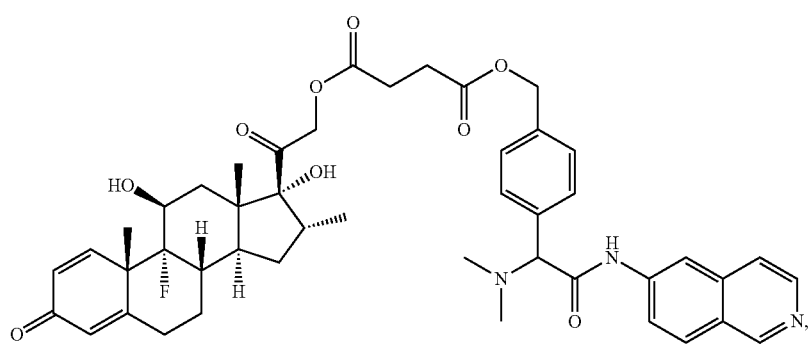

-continued
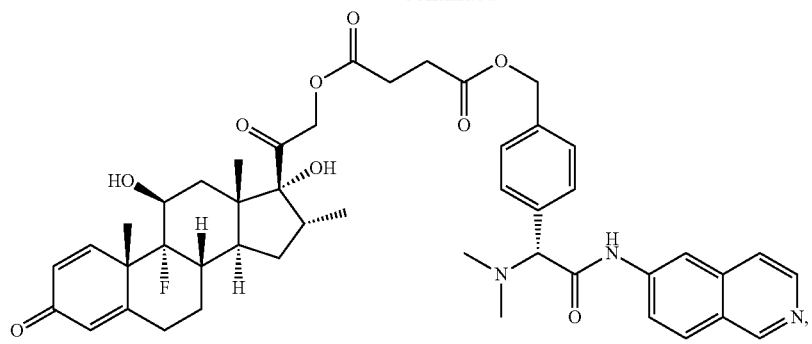
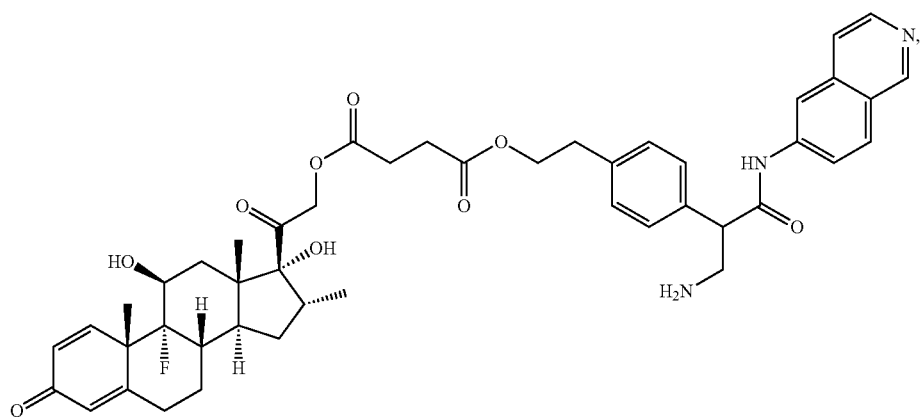
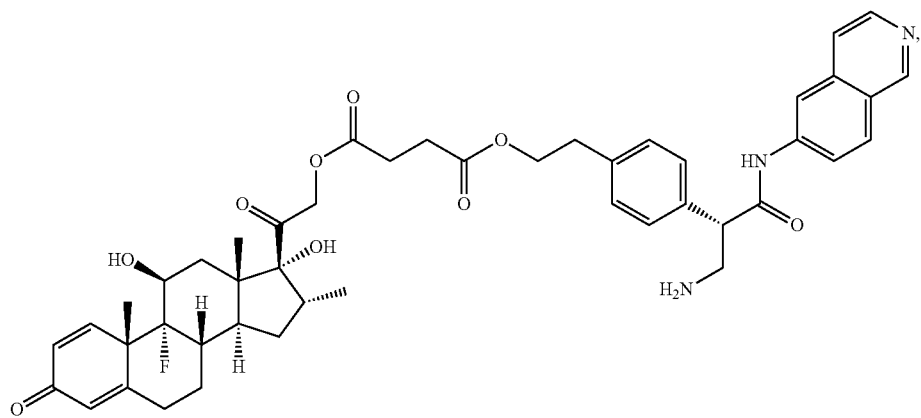
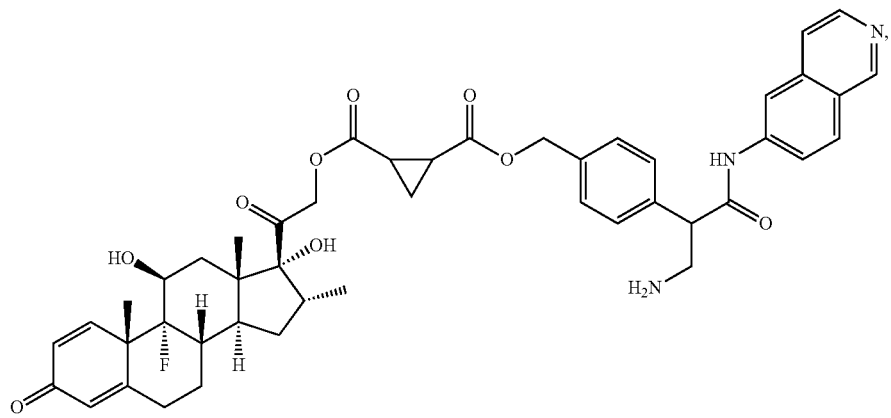

-continued
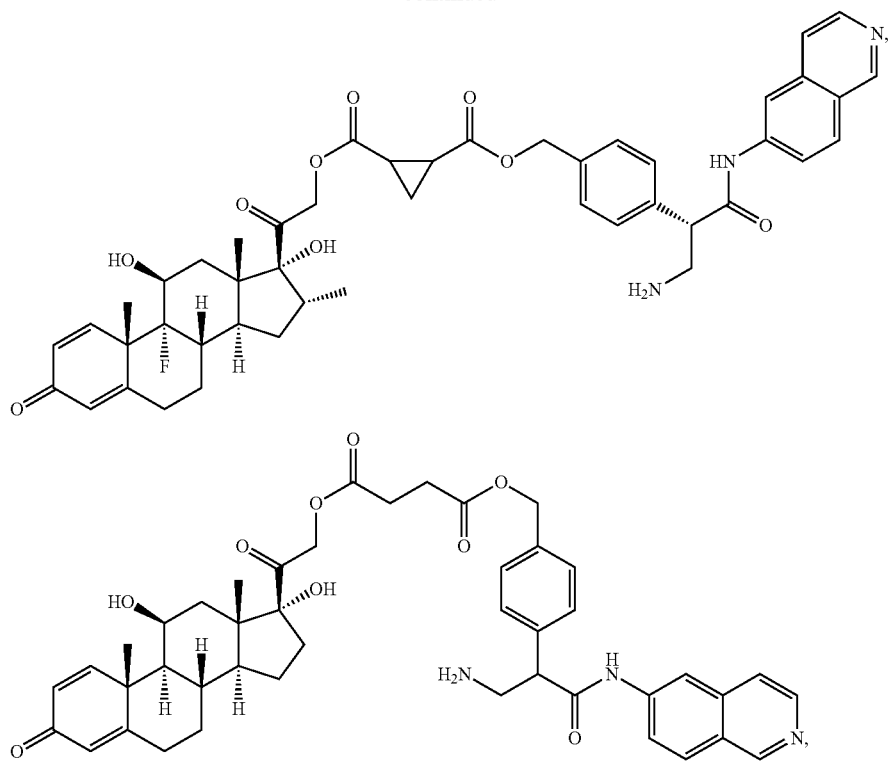
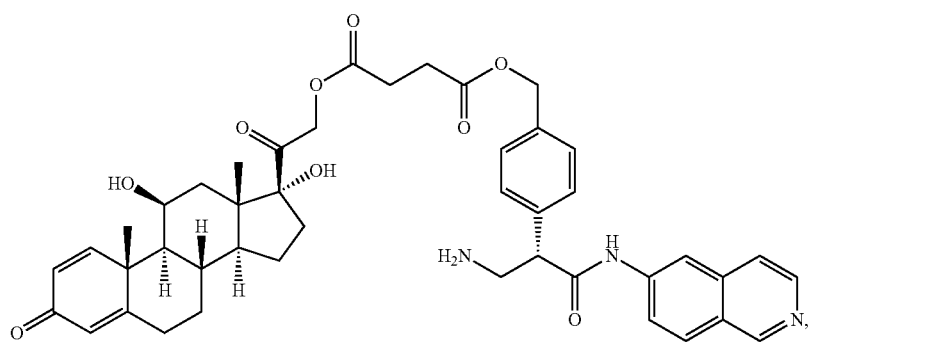
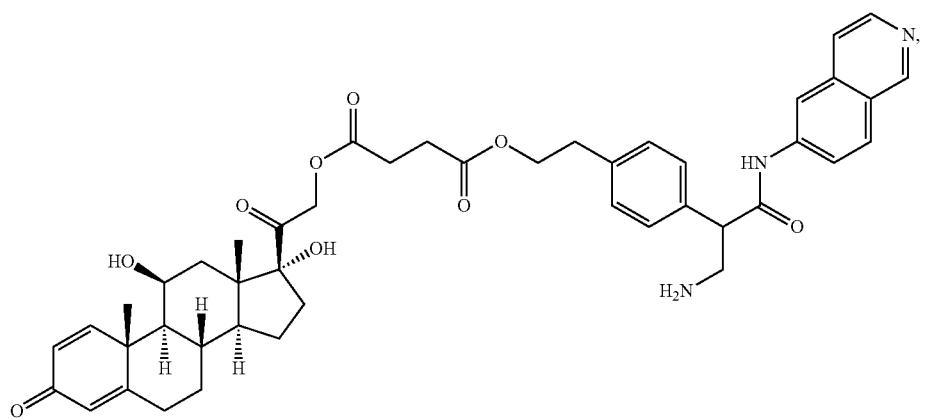

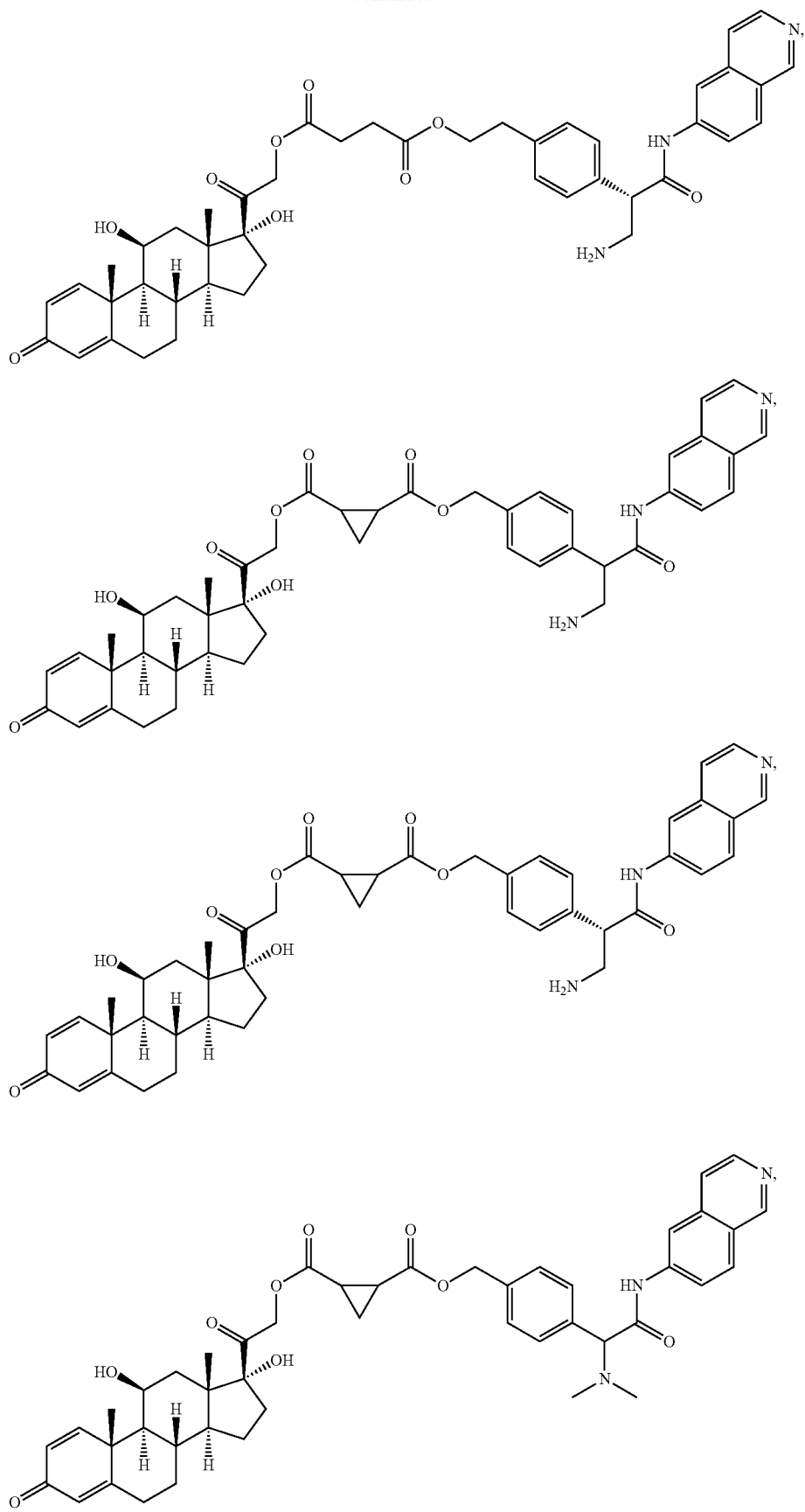

-continued
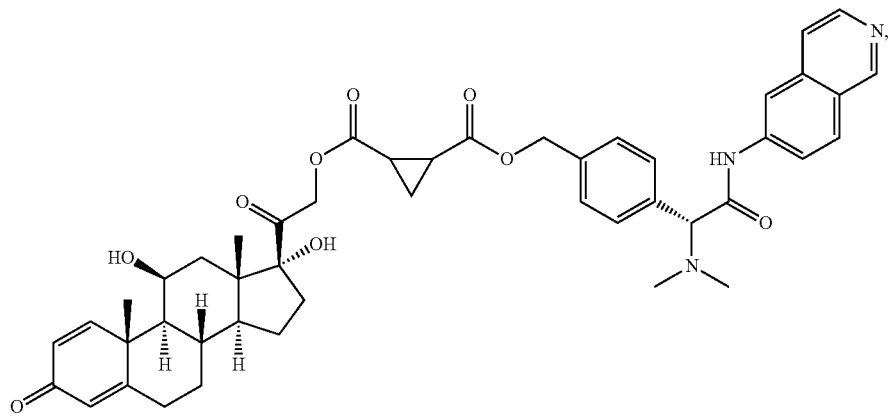
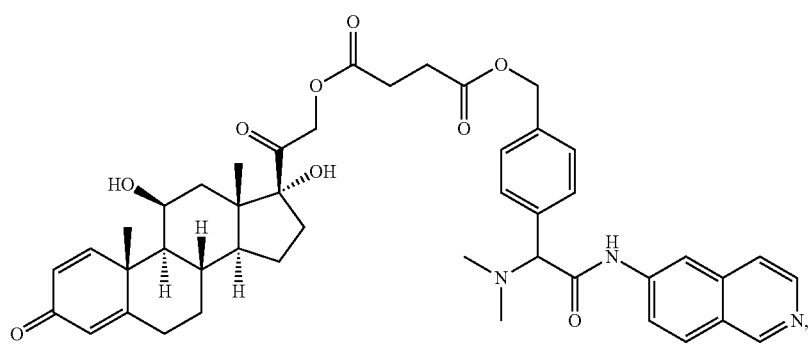
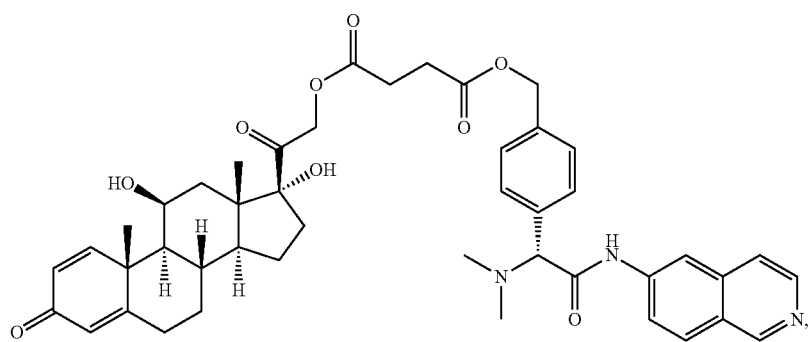
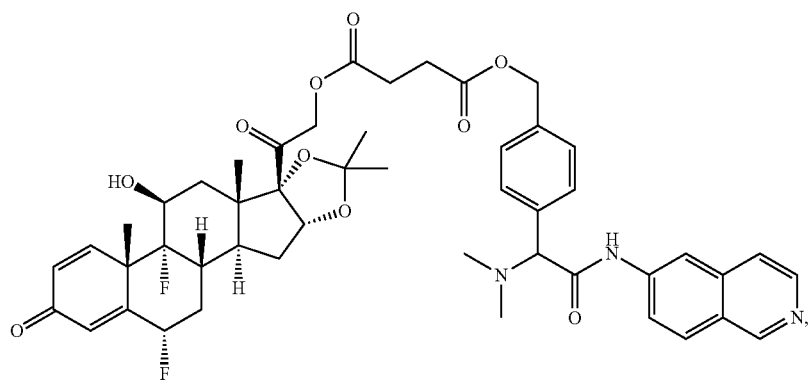

-continued
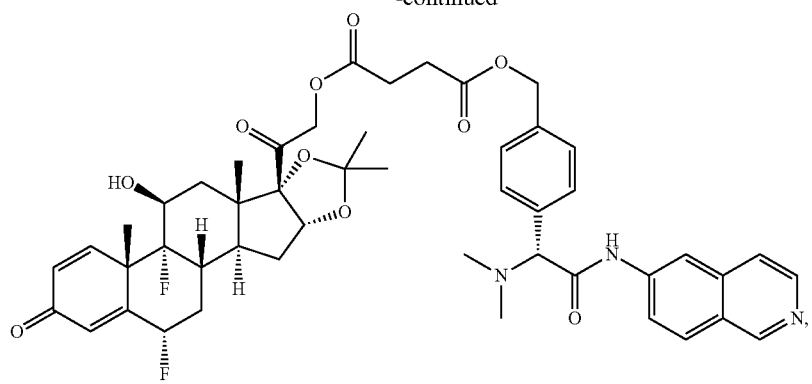
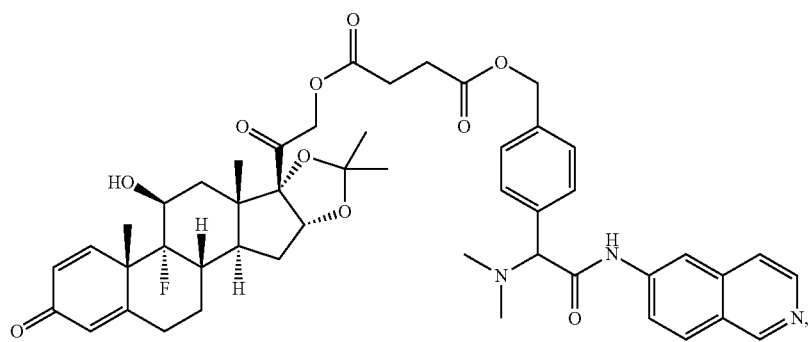
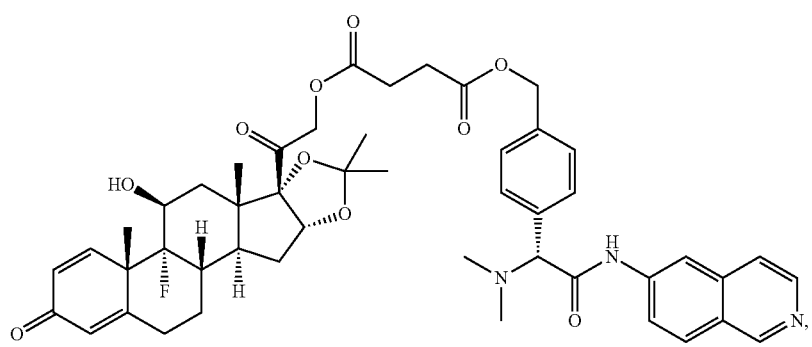
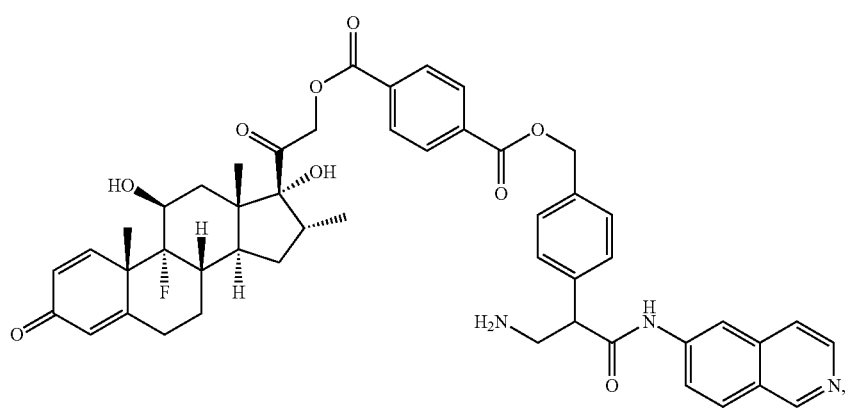

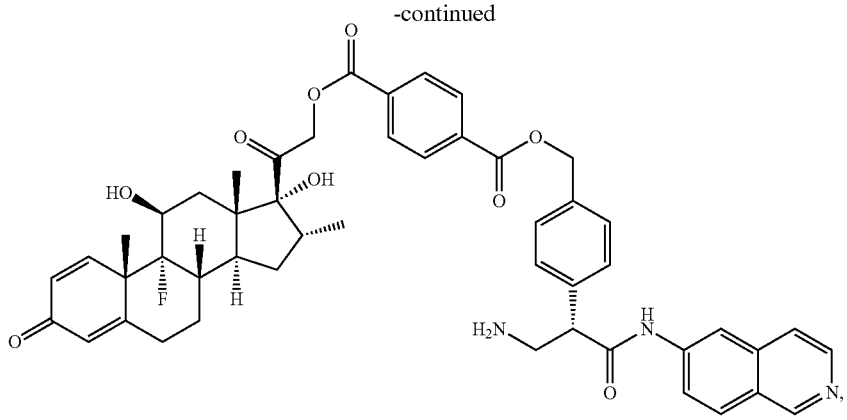
or a pharmaceutically acceptable salt thereof.
In some embodiments, the compound of Formula (I) is a compound of Formula (IX):
$$R^8\text{—}R^{10}\text{—}R^{11} \qquad (IX)$$
or a pharmaceutically acceptable salt thereof, wherein
$R^8$ is
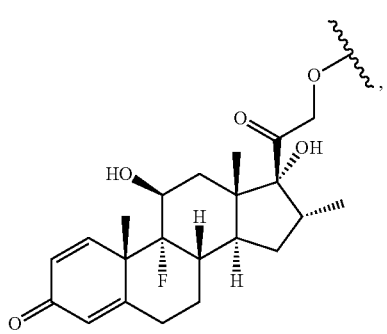
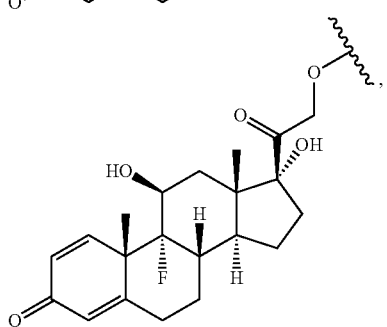
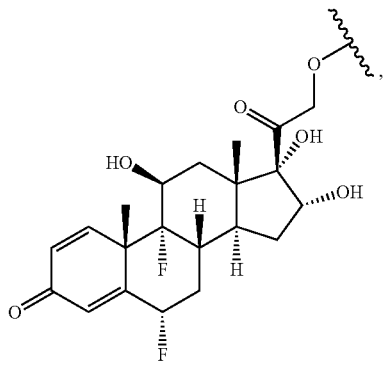
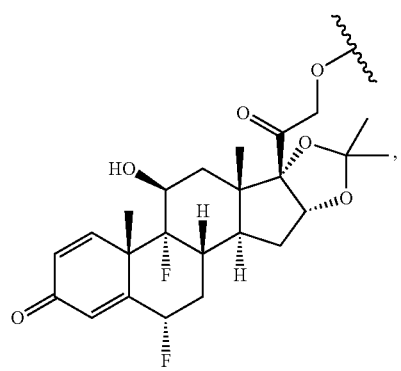
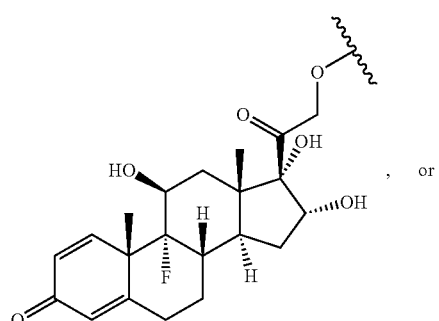, or
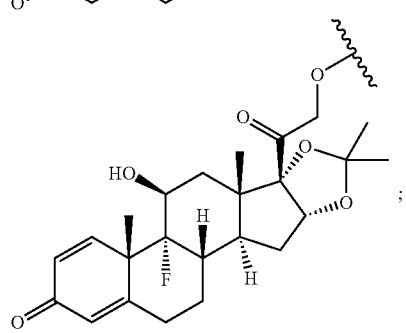;
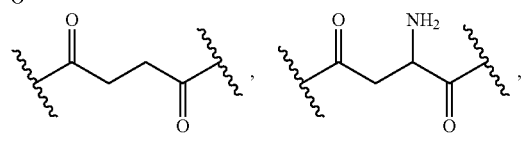

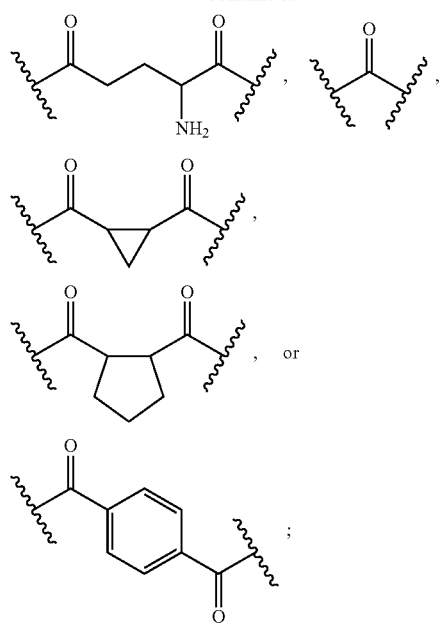
$R^{10}$ is
and
$R^{11}$ is
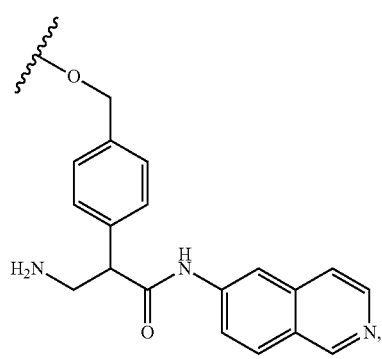
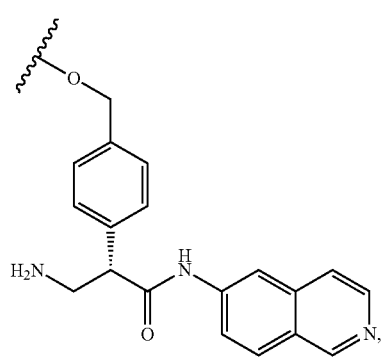
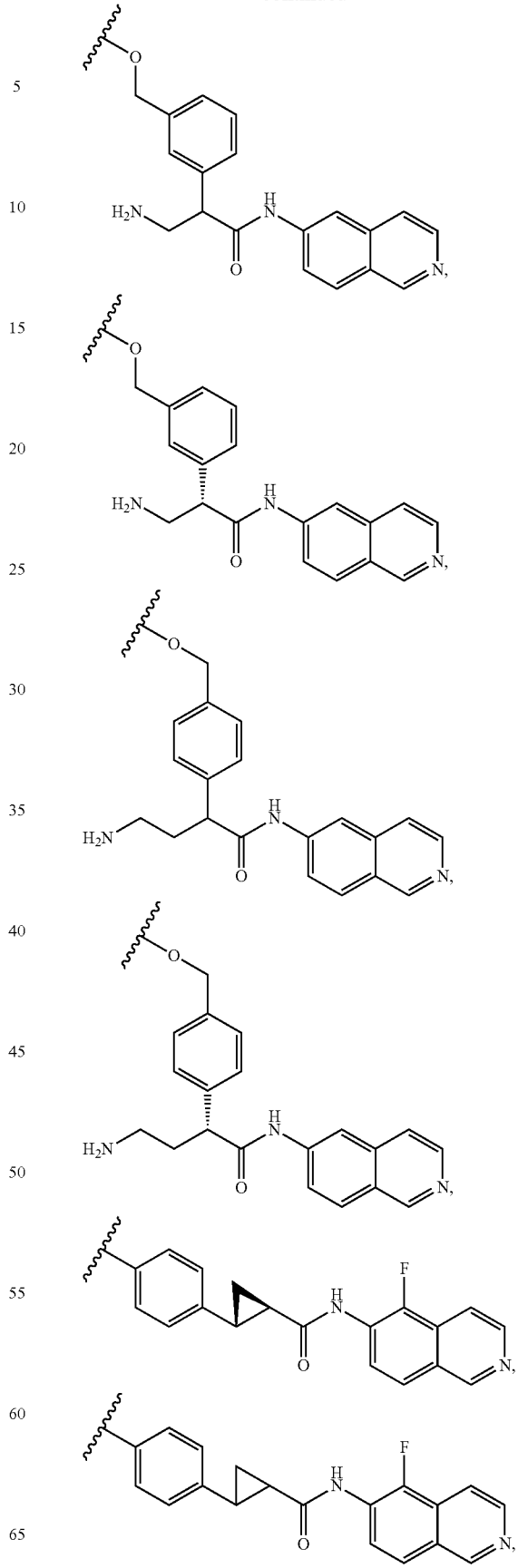

-continued
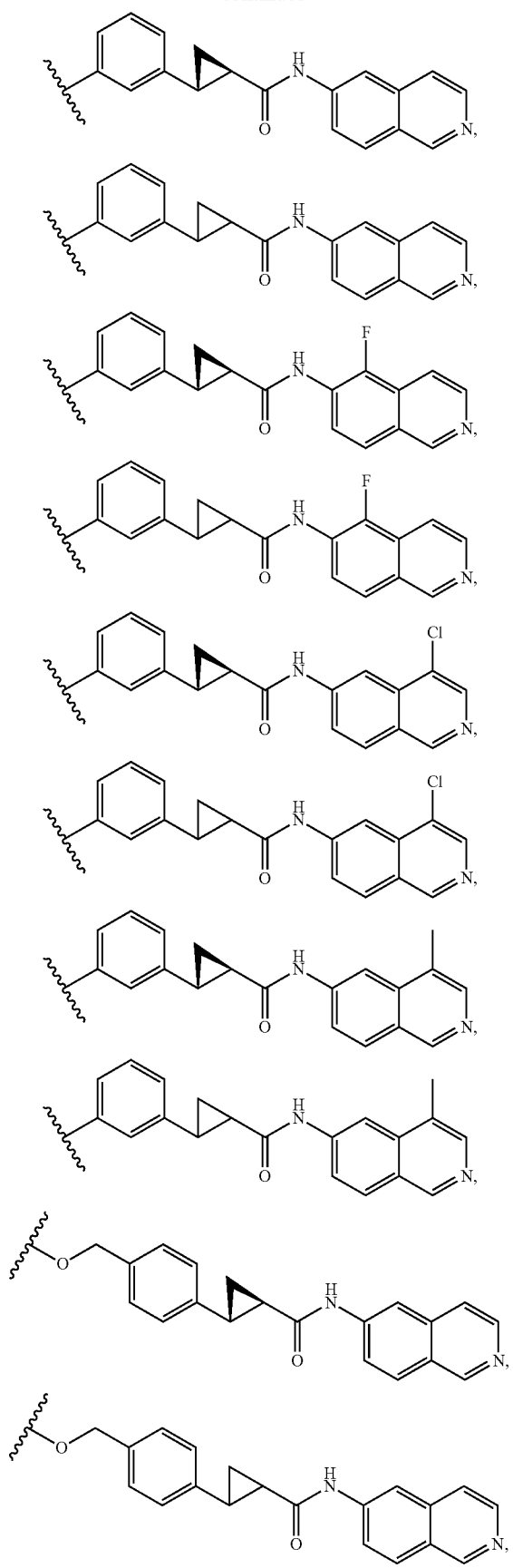
-continued
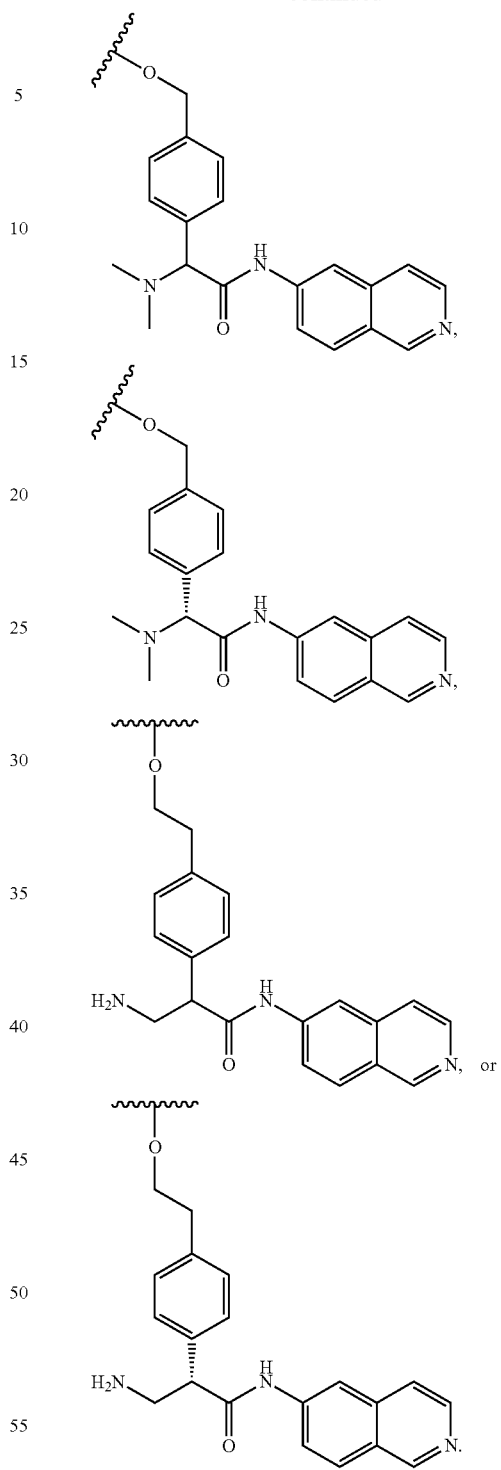
In some embodiments, the compound of Formula (I) is a compound of Formula (IX):
$$R^8-R^{10}-R^{11}$$ (IXa)

or a pharmaceutically acceptable salt thereof, wherein
R⁸ is
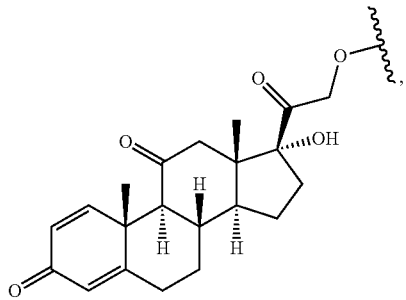
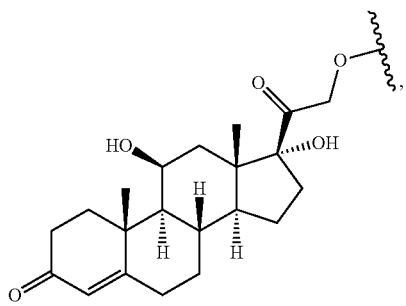
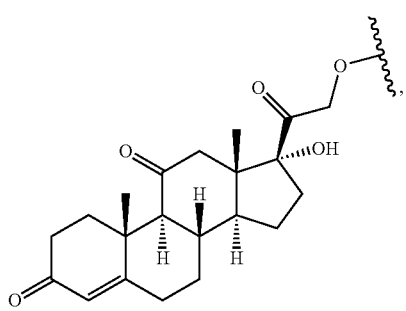
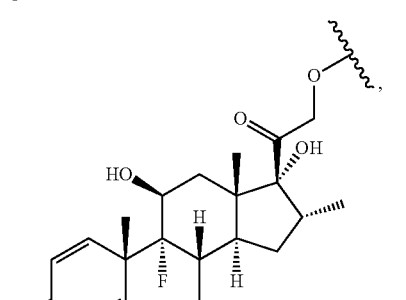
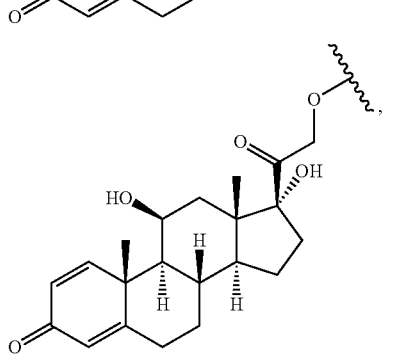
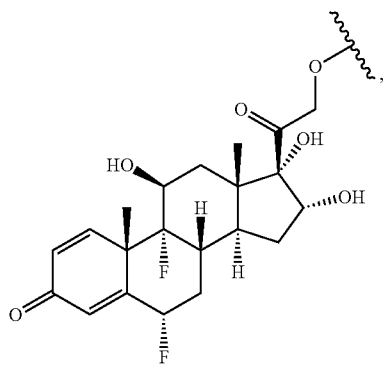
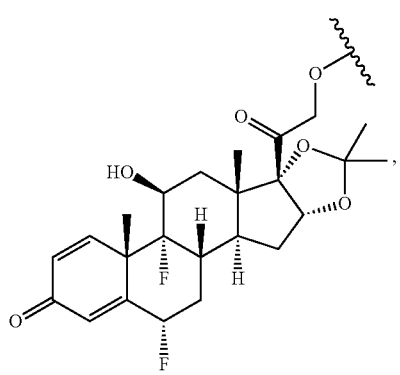
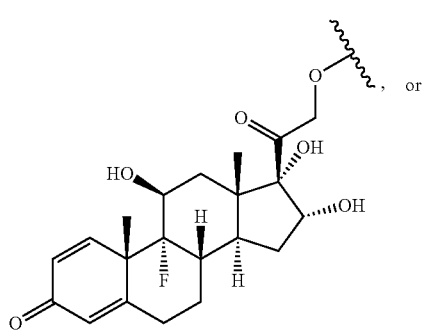, or
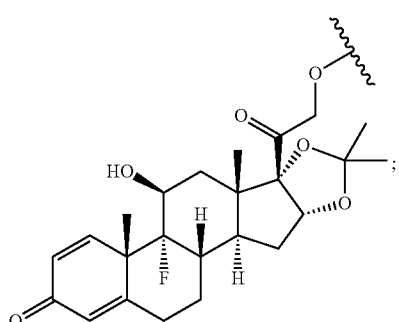
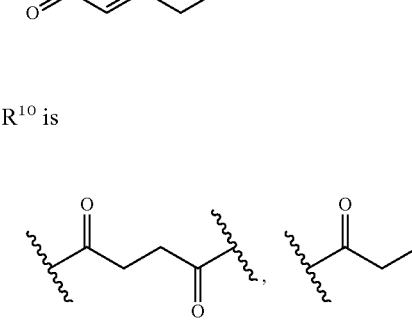;
R¹⁰ is
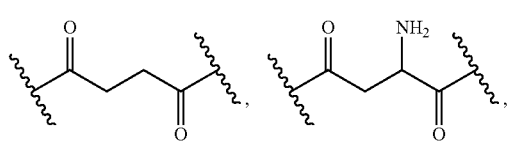

-continued
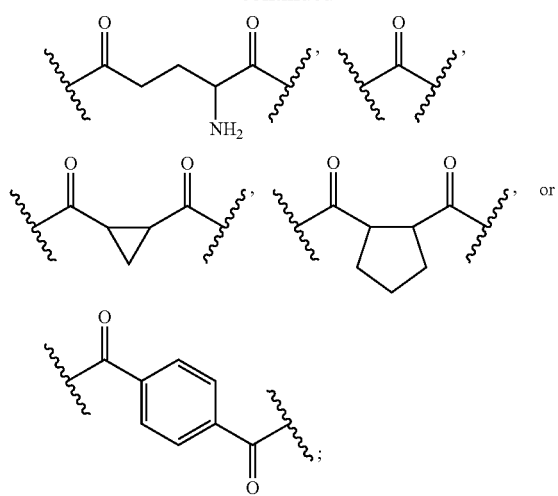
and
R[11] is
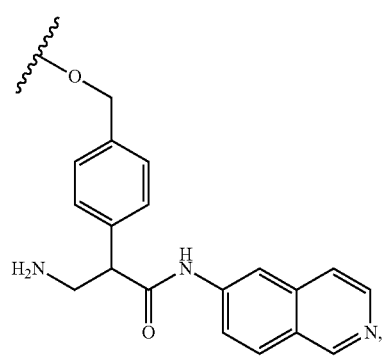
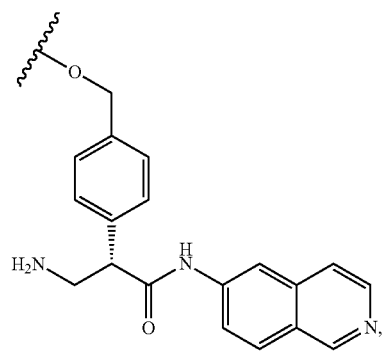
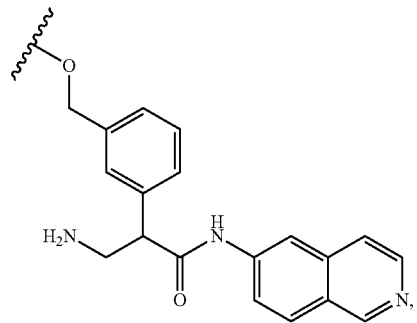
-continued
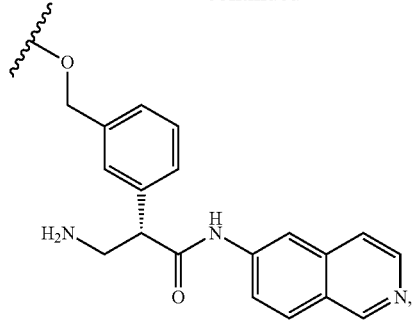
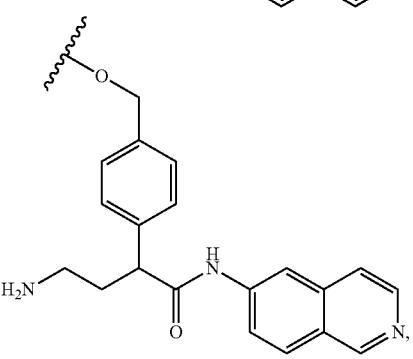
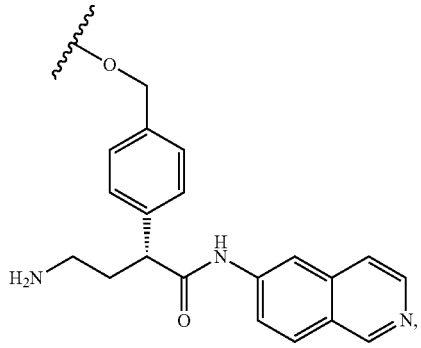
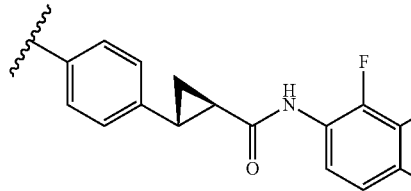
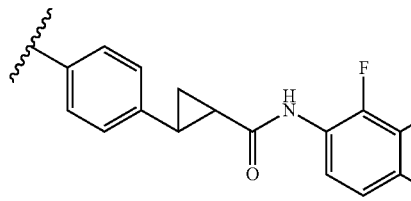
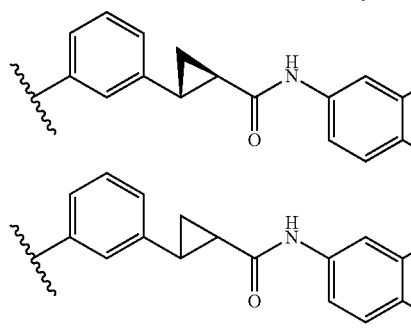

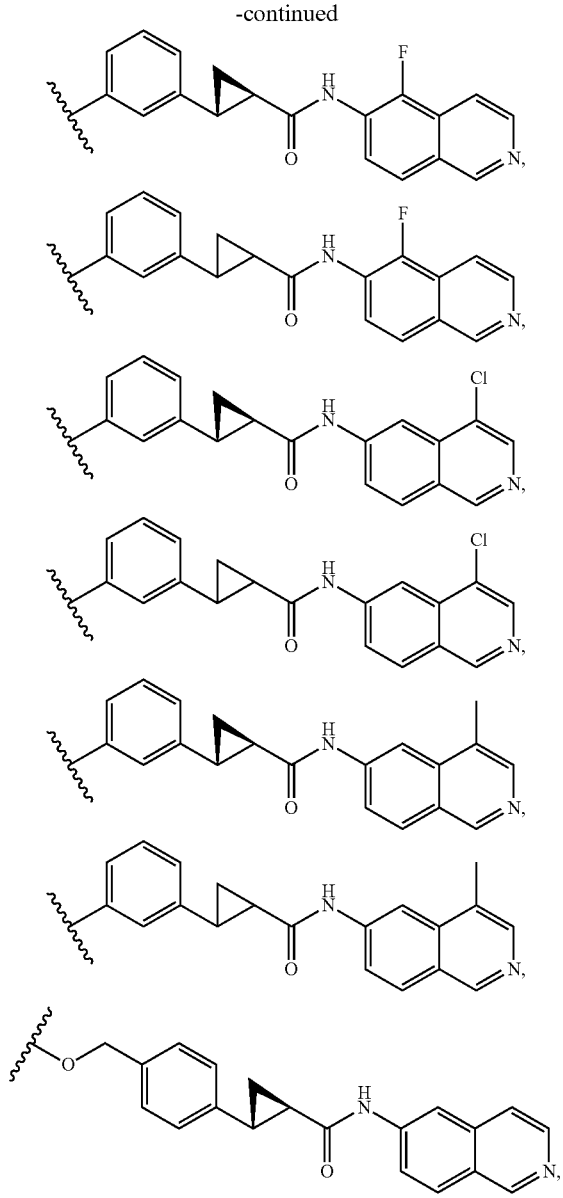
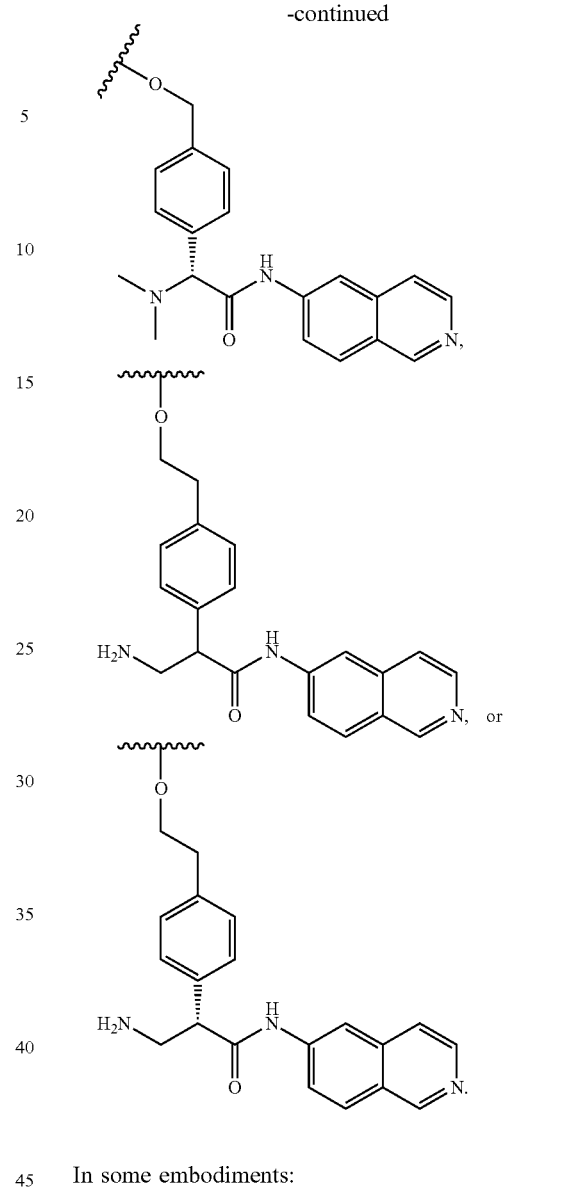
In some embodiments:
R[10] is
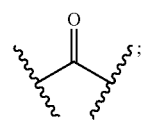
and
R[11] is
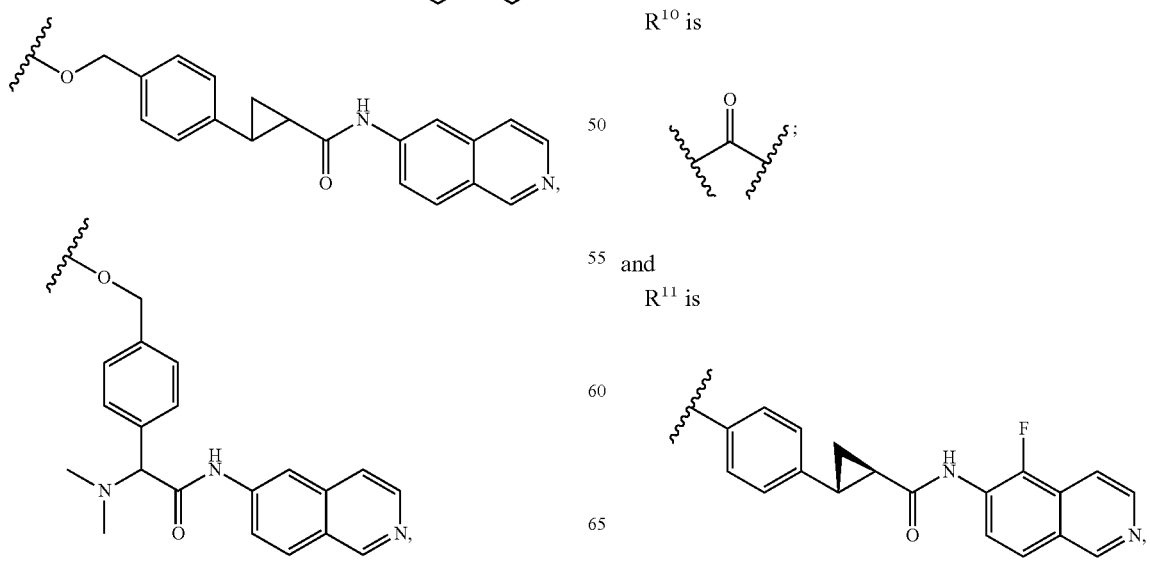

-continued
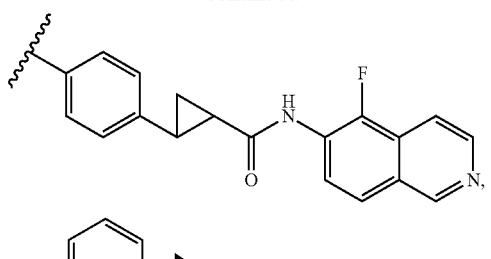
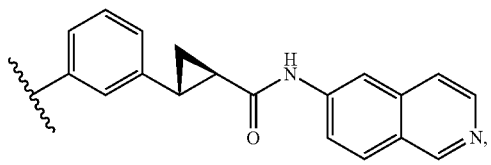
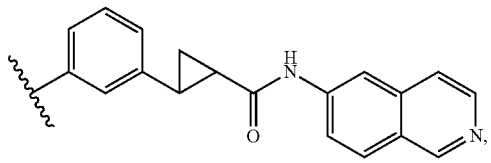
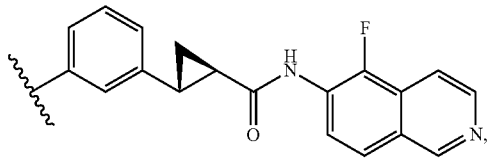
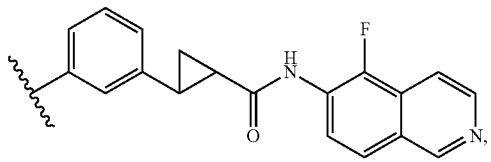
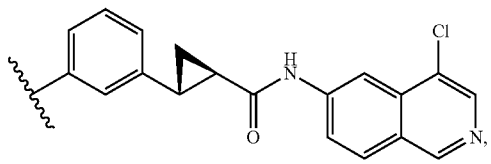
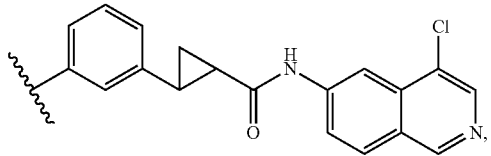
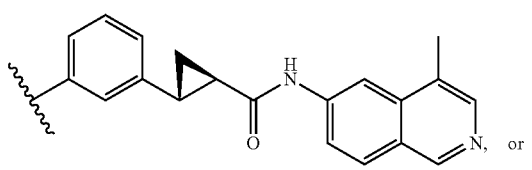
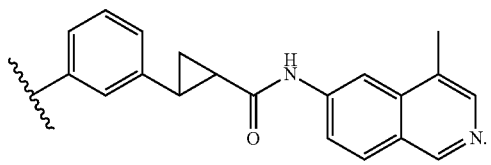
In some embodiments:
$R^{10}$ is
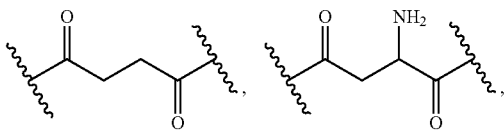
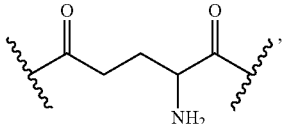
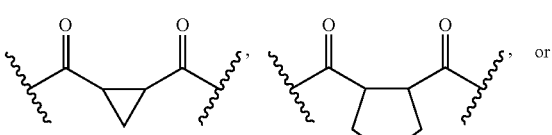
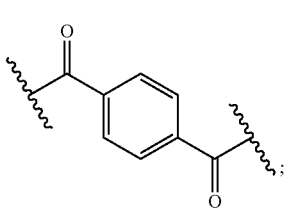
and
$R^{11}$ is
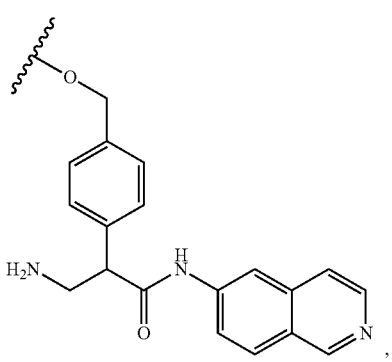
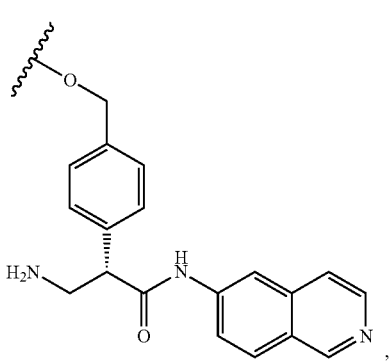

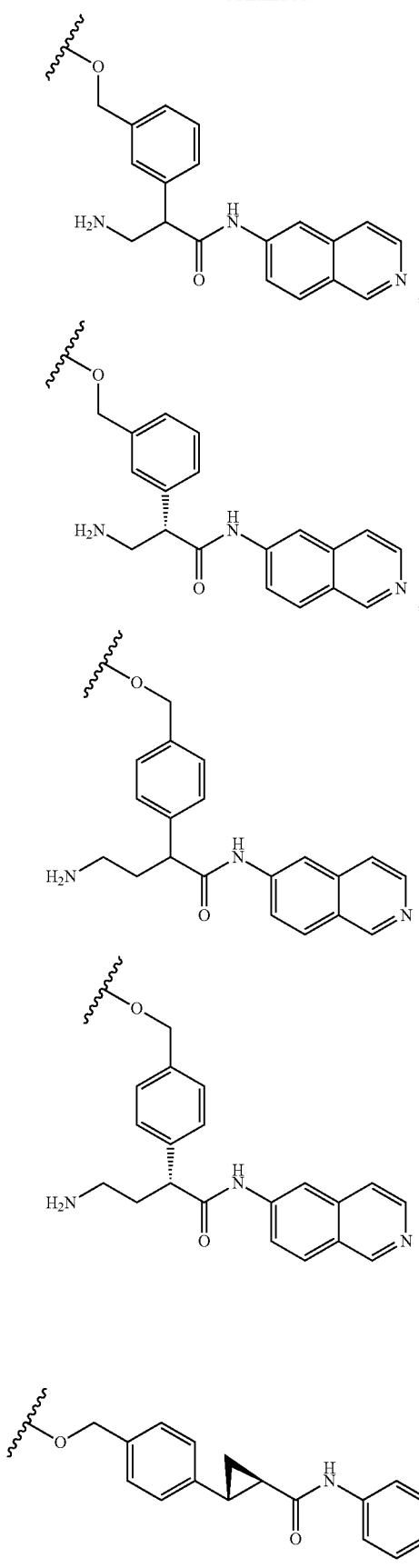

In some embodiments, the compound is a compound of Table 1, Table 2, Table 3, Table 4, Table 5, Table 6, Table 7, Table 8, or Table 9, or a pharmaceutically acceptable salt thereof.
TABLE 1
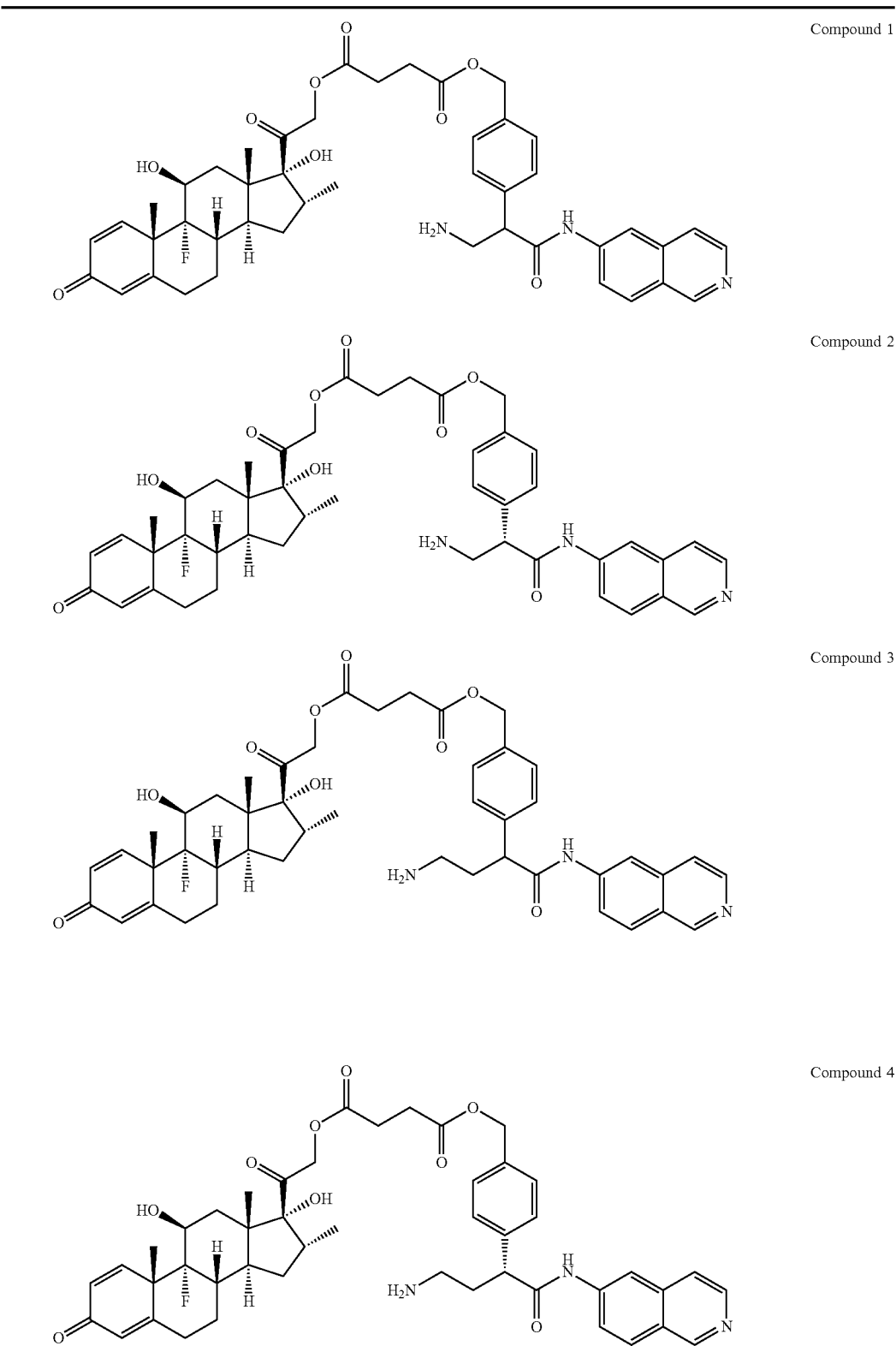

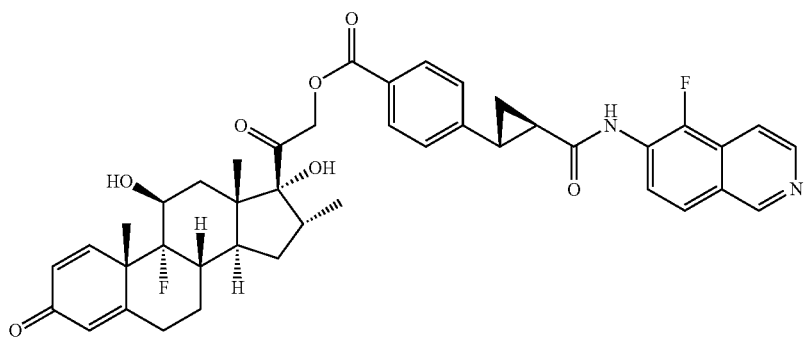
Compound 5
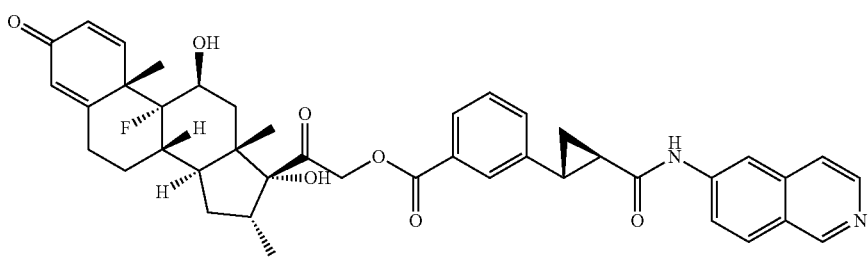
Compound 6
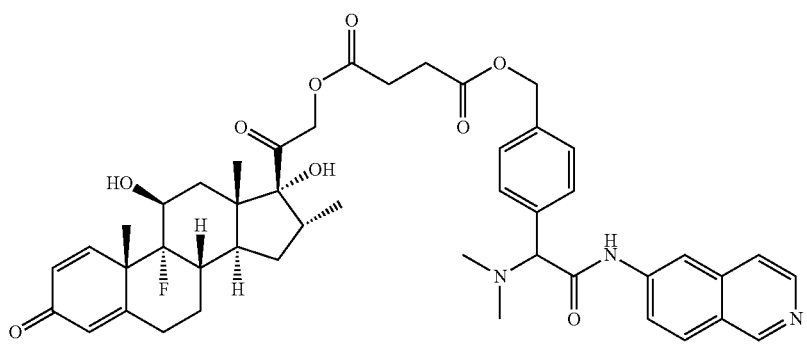
Compound 7
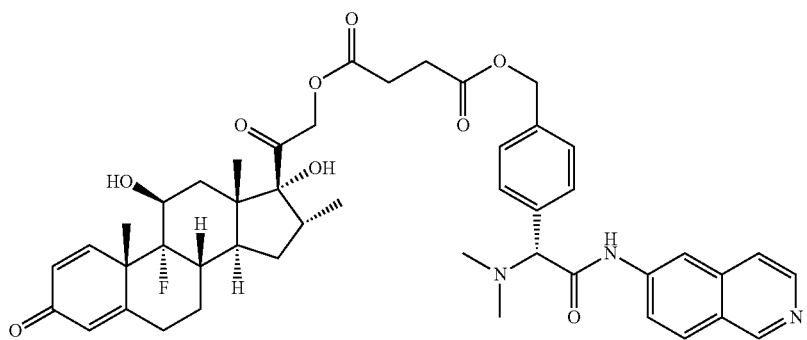
Compound 8

TABLE 1-continued
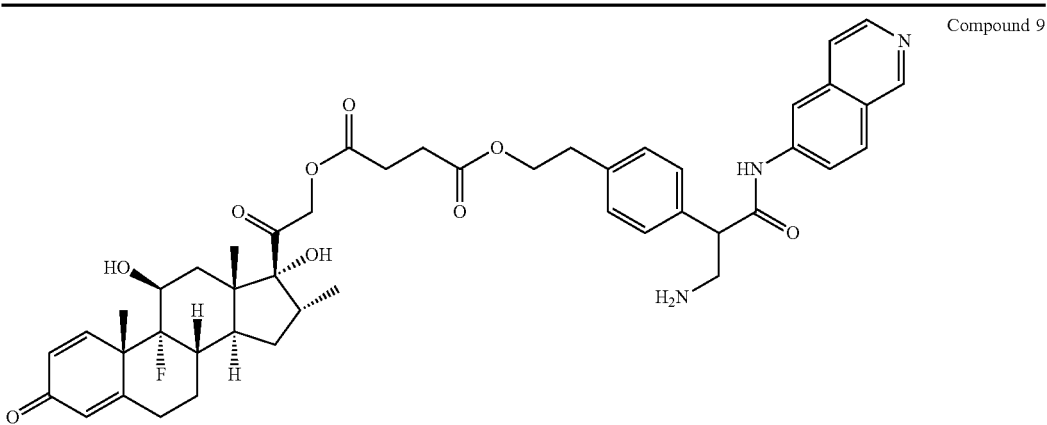
Compound 9
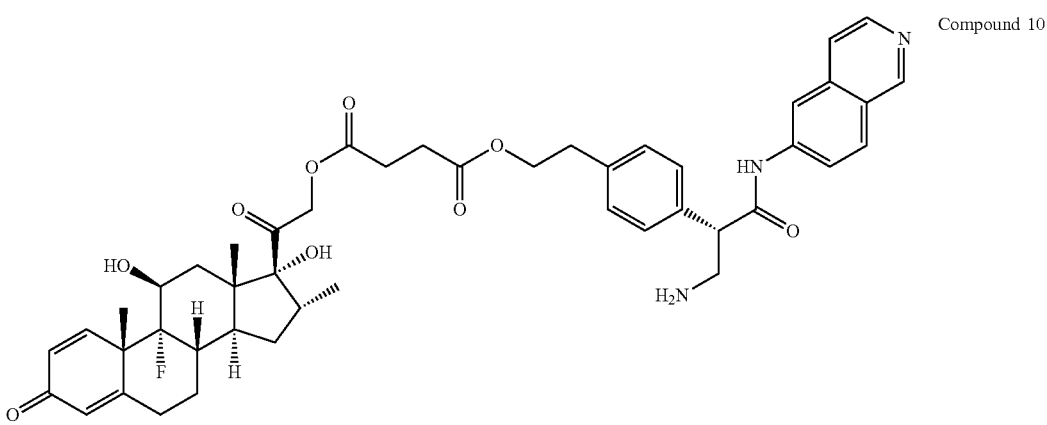
Compound 10
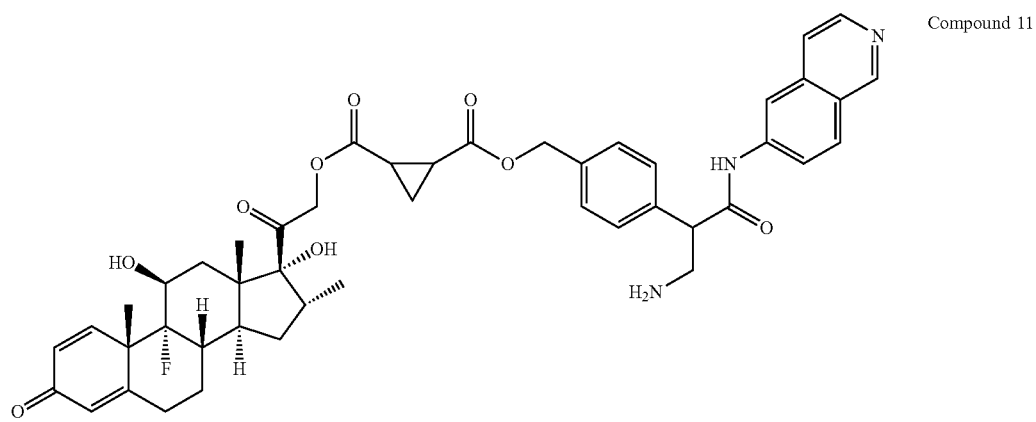
Compound 11

TABLE 1-continued
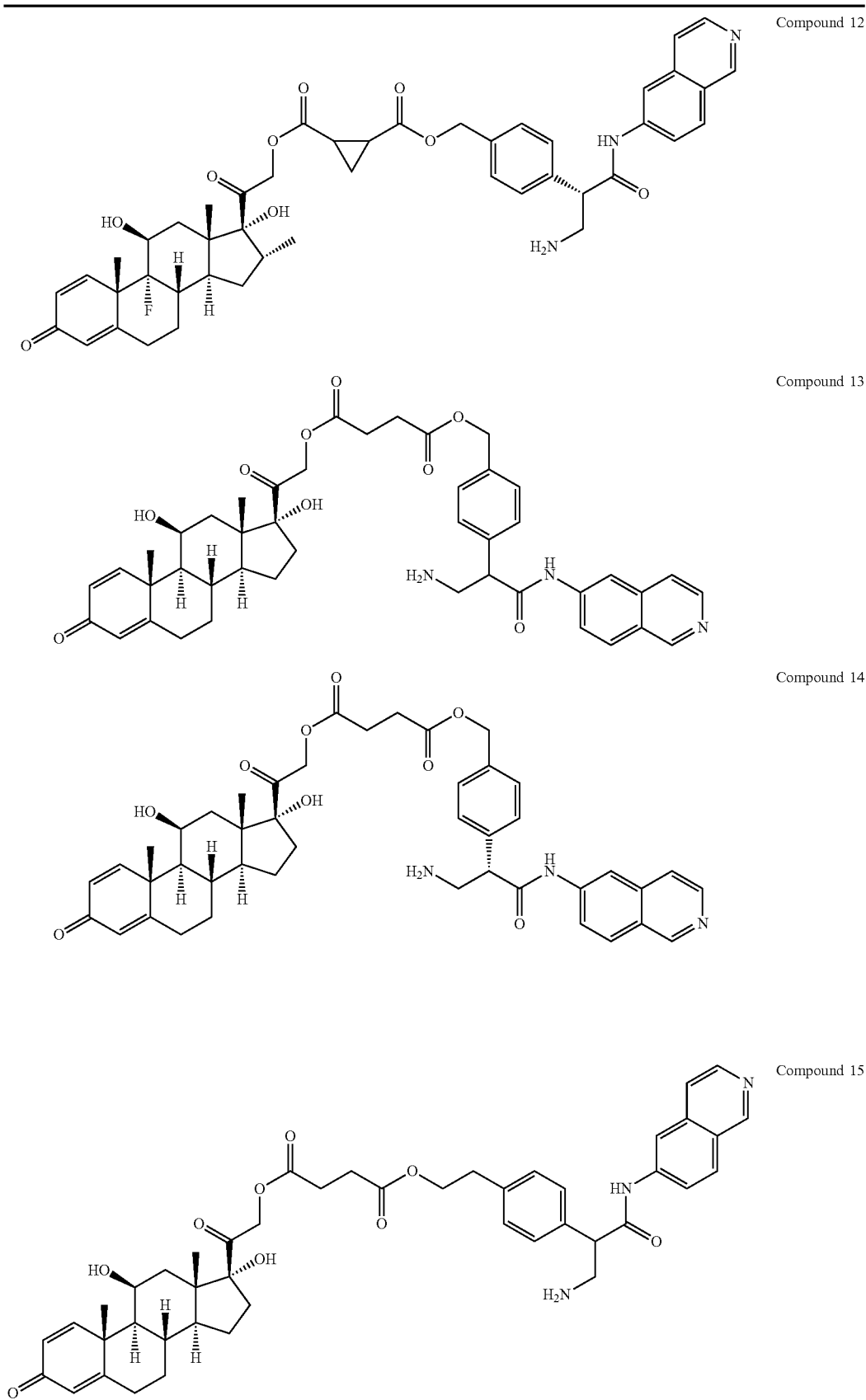
Compound 12
Compound 13
Compound 14
Compound 15

TABLE 1-continued
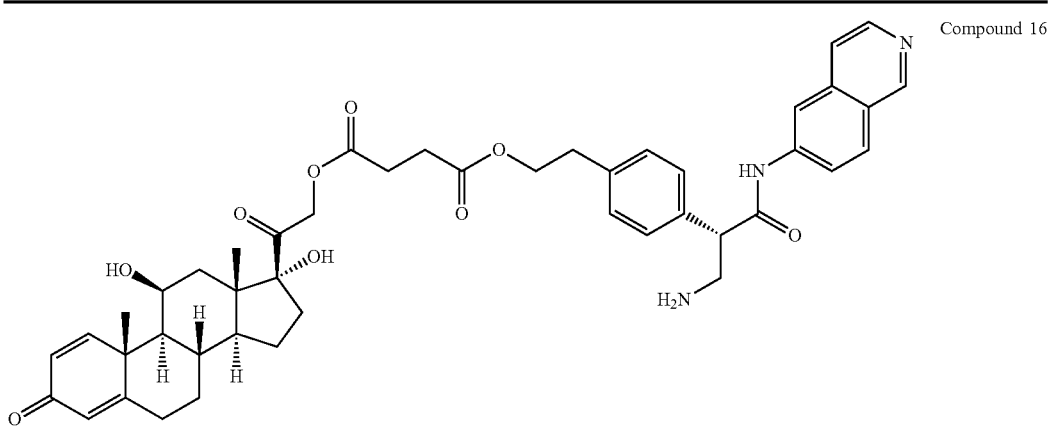
Compound 16
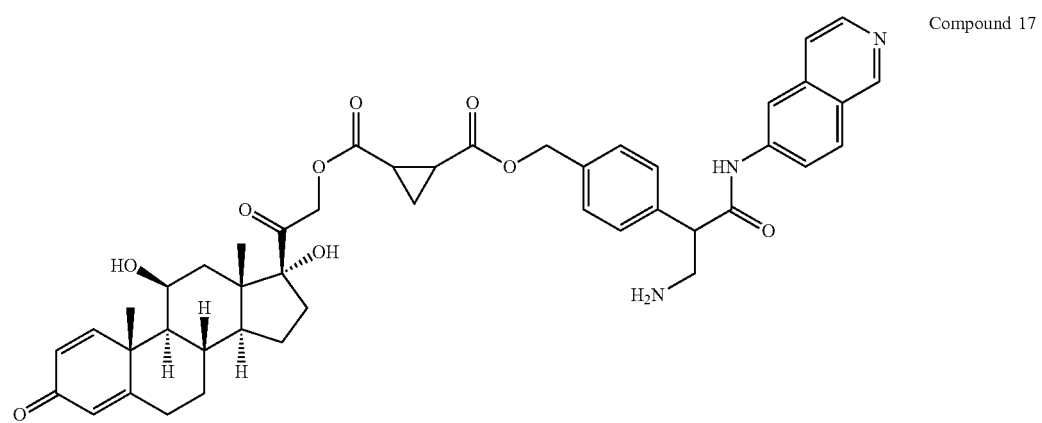
Compound 17
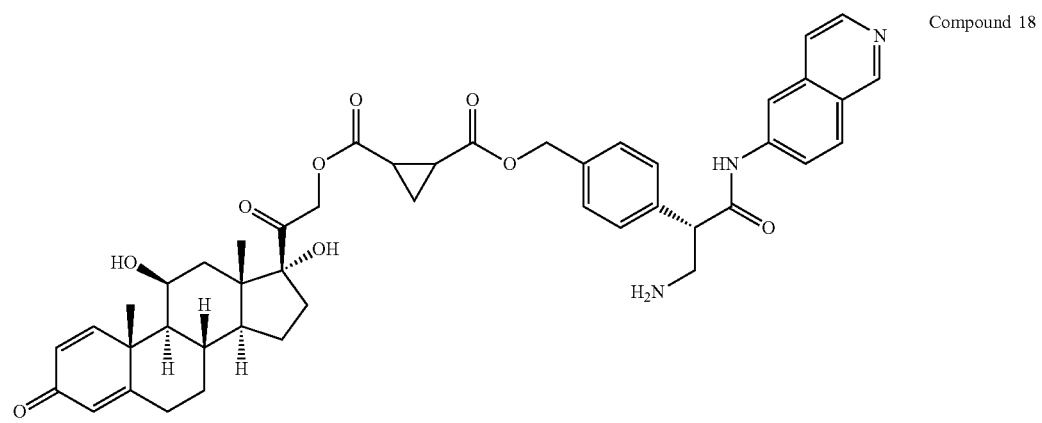
Compound 18

TABLE 1-continued
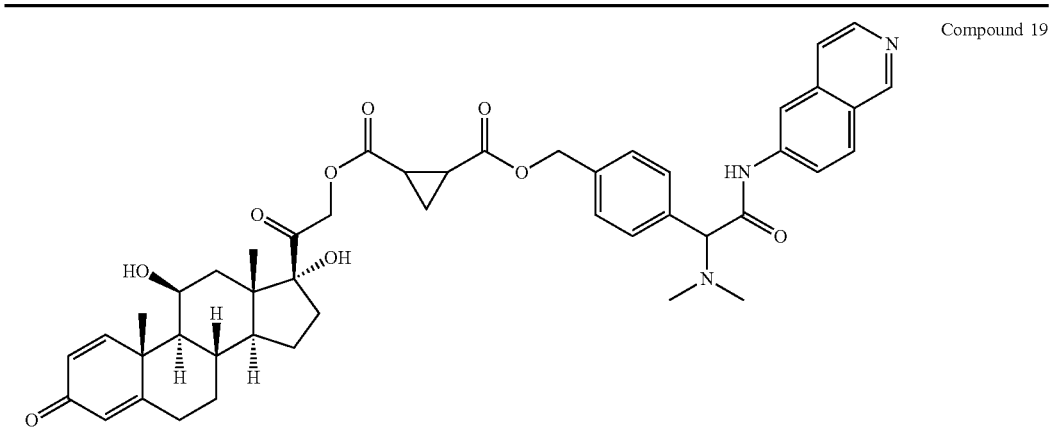
Compound 19
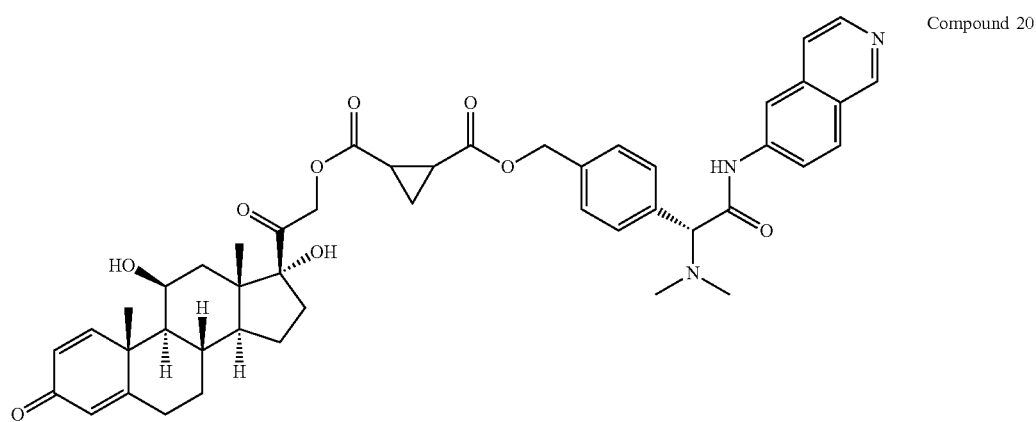
Compound 20
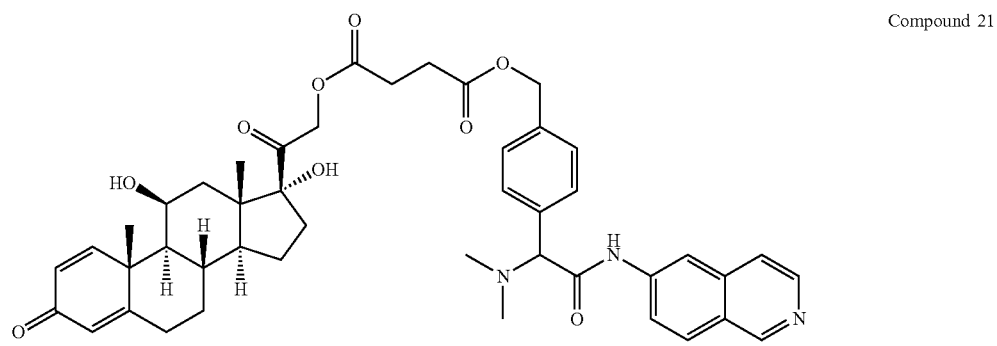
Compound 21
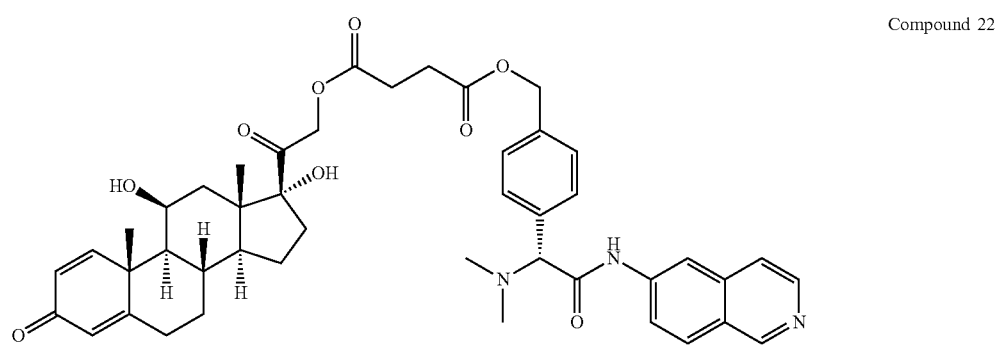
Compound 22

TABLE 1-continued
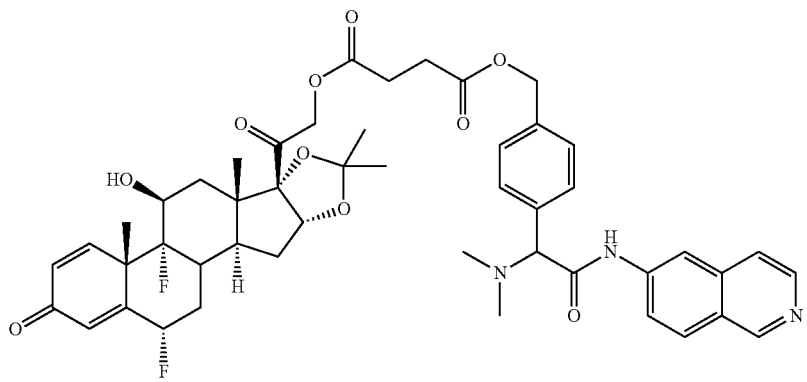
Compound 23
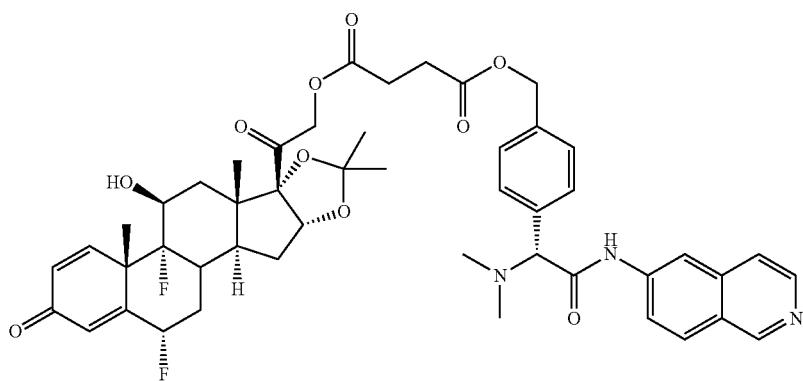
Compound 24
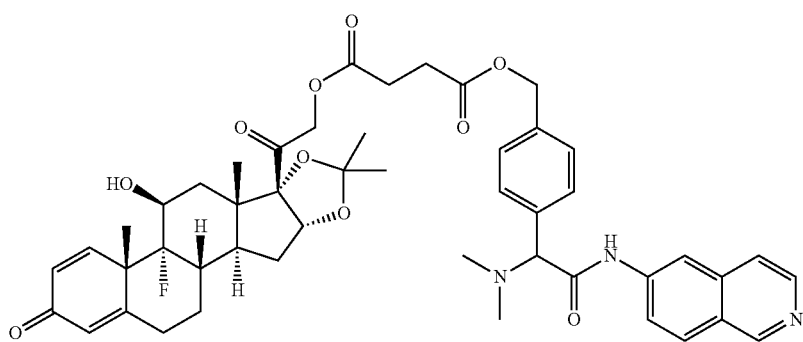
Compound 25
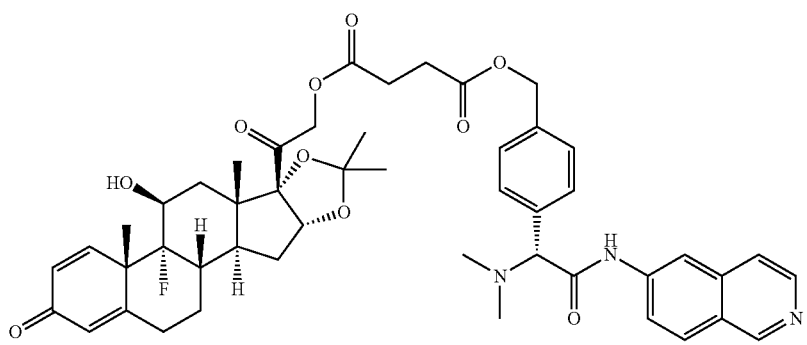
Compound 26

TABLE 1-continued

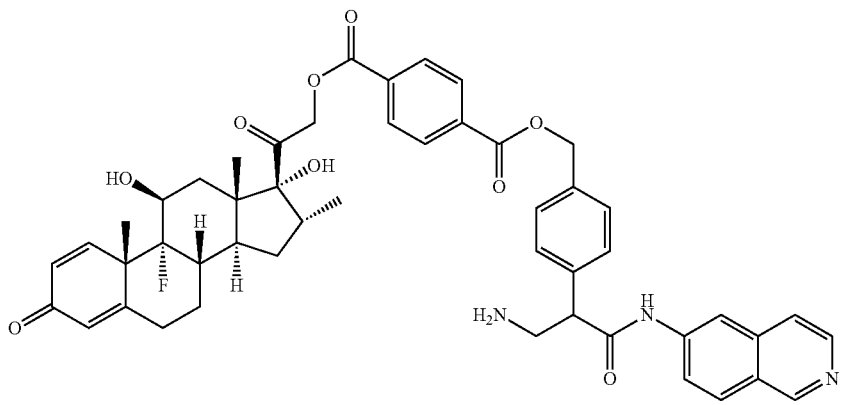

Compound 27

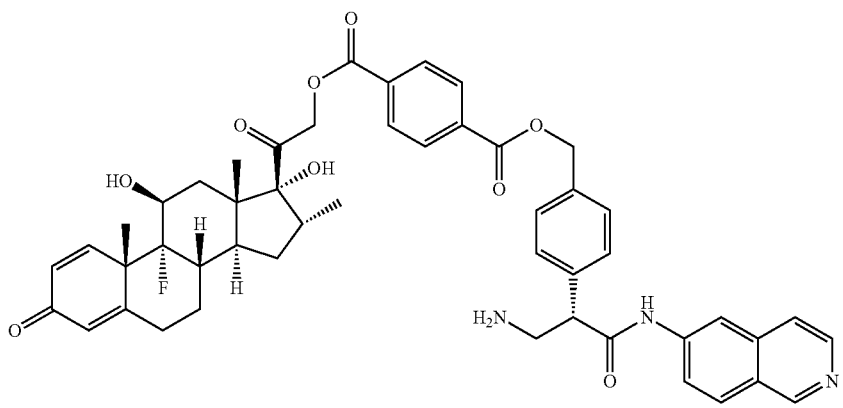

Compound 28

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

It will be appreciated that the description of the compounds provided herein should be construed in congruity with the laws and principals of chemical bonding. In some instances it may be necessary to remove a hydrogen atom in order to accommodate a substituent at any given location. Some compounds shown in the tables provided herein may not include hydrogens on hydroxyl groups or amine groups (i.e. primary or secondary amines); it is understood that hydrogen is present at these positions if not shown, just as a carbon may not always explicitly show every hydrogen attached thereto.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey and Sundberg, Advanced Organic Chemistry 4th Ed., Vols. A and B (Plenum 2000, 2001), and Greene and Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

Methods

Provided herein are methods of treating a disease in a subject in need thereof, comprising administering to the subject an effective amount of a compound provided herein.

Thus, in one aspect, provided herein is a method of treating an eye disease or disorder in a subject in need thereof, comprising administering to the subject an effective amount of a compound of Formulae I-X or a pharmaceutically acceptable salt thereof.

In some embodiments, provided herein is a method of treating an eye disease or disorder in a subject in need thereof, comprising administering to the subject an effective amount of a compound of Table 1, Table 2, Table 3, Table 4, Table 5, Table 6, Table 7, Table 8, Table 9, or a pharmaceutically acceptable salt thereof.

In some embodiments, the eye disease or disorder comprises glaucoma, a neurodegenerative eye disease or disorder, dry eye, ocular hypertension, or an ocular inflammatory disease or disorder.

Also provided herein are methods of reducing intraocular pressure in an eye of a subject in need thereof, comprising administering to the subject an effective amount of a compound provided herein.

Thus, in another aspect, provided herein is a method of reducing intraocular pressure in an eye of a subject in need thereof, comprising administering to the subject an effective amount of a compound of Formulae I-X or a pharmaceutically acceptable salt thereof.

In some embodiments, provided herein is a method of reducing intraocular pressure in an eye of a subject in need thereof, comprising administering to the subject an effective amount of a compound of Table 1, Table 2, Table 3, Table 4, Table 5, Table 6, Table 7, Table 8, Table 9, or a pharmaceutically acceptable salt thereof.

In some embodiments, the subject is suffering from glaucoma or ocular hypertension.

Also provided herein are methods of modulating kinase activity in a cell, comprising contacting the cell with an amount effective to modulate kinase activity of a compound provided herein.

Thus, in yet another aspect, provided herein is a method of modulating kinase activity in a cell, comprising contacting the cell with an amount effective to modulate kinase activity of a compound of Formulae I-X or a pharmaceutically acceptable salt thereof.

In some embodiments, provided herein is a method of modulating kinase activity in a cell, comprising contacting the cell with an amount effective to modulate kinase activity of a compound of Table 1, Table 2, Table 3, Table 4, Table 5, Table 6, Table 7, Table 8, Table 9, or a pharmaceutically acceptable salt thereof.

In another aspect, provided herein are methods of treating an ocular inflammatory disease or disorder in a subject having physiological intraocular pressure, comprising the steps of: a) measuring visual acuity of the subject; and b) administering to the subject an effective amount of a compound of Formulae I-X or a pharmaceutically acceptable salt thereof.

In some embodiments of these methods, the modulation of intraocular pressure is a reduction of intraocular pressure. In some embodiments, the modulation of intraocular pressure is an increase of intraocular pressure that remains within the range of physiological intraocular pressure. In some embodiments, the modulation of intraocular pressure is an increase of intraocular pressure greater than the range of physiological intraocular pressure, but the visual acuity of the subject is unchanged.

In another aspect, provided herein are methods of treating an ocular inflammatory disease or disorder in a subject having intraocular pressure greater than physiological intraocular pressure, comprising the steps of: (a) measuring visual acuity of the subject; and (b) administering to the subject an effective amount of a compound of Formulae I-X or a pharmaceutically acceptable salt thereof; wherein the administration of the effective amount of the compound modulates intraocular pressure.

In some embodiments of these methods, the modulation of intraocular pressure is a reduction of intraocular pressure. In some embodiments, the modulation of intraocular pressure is an increase in intraocular pressure that does not affect the measured visual acuity.

In another aspect, provided herein are methods of treating an ocular inflammatory disease or disorder in a subject having an intra ocular pressure that is greater than physiological intraocular pressure and is gradually increasing, comprising administering to the subject an effective amount of a compound of Formulae I-X or a pharmaceutically acceptable salt thereof, wherein the administration of the effective amount of the compound modulates intraocular pressure.

In some embodiments of these methods, the modulation of intraocular pressure is a decrease of the intraocular pressure. In some embodiments, the modulation of the intraocular pressure is a halt of the gradual increase in intraocular pressure. In some embodiments, the modulation of the intraocular pressure is a reduction in the gradual increase in intraocular pressure compared to the gradual increase of intraocular pressure prior to the administration of an effective amount of the compound. In some embodiments, the subject suffers from glaucoma.

In another aspect, provided herein are methods of preventing a deleterious increase in intraocular pressure in a subject in need thereof, comprising administering to the subject an effective amount of the compound of any of Formulae I-X or a pharmaceutically acceptable salt thereof.

In another aspect, provided herein are methods of modulating intraocular pressure in a subject in need thereof, comprising administering to the subject an effective amount of the compound of any of Formulae I-X or a pharmaceutically acceptable salt thereof, wherein the subject experiences a visual acuity loss of not more than three letters.

In another aspect, provided herein are methods of treating ocular hypertension in a subject in need thereof, comprising administering to the subject an effective amount of the compound of any of Formulae I-X or a pharmaceutically acceptable salt thereof.

In another aspect, provided herein are methods of preventing ocular hypertension in a subject in need thereof, comprising administering to the subject an effective amount of the compound of any of Formulae I-X or a pharmaceutically acceptable salt thereof.

In another aspect, provided herein are methods of reducing the progression of ocular hypertension in a subject in need thereof, comprising administering to the subject an effective amount of the compound of any of Formulae I-X or a pharmaceutically acceptable salt thereof.

In some embodiments of these methods, the subject experiences a slower rate of progression of ocular hypertension upon administration of the compound as compared to the rate of progression of ocular hypertension in the subject: a) without administration of the compound; or b) upon administration of a steroid as an ocular therapy.

In another aspect, provided herein are methods of reducing the progression of increased intraocular pressure in a subject in need thereof, comprising administering to the subject an effective amount of the compound of Formulae I-X or a pharmaceutically acceptable salt thereof.

In some embodiments of these methods, the subject experiences a slower rate of progression of intraocular pressure upon administration of the compound as compared to the rate of progression of intraocular pressure in the subject: a) without administration of the compound; or b) upon administration of a steroid as an ocular therapy.

In some embodiments of these methods, the steroid is a glucocorticoid.

In another aspect, provided herein are methods of inducing transrepression of at least one proinflammatory transcription factor in a subject in need thereof, comprising administering to the subject an effective amount of the compound of any of Formulae I-X or a pharmaceutically acceptable salt thereof.

In another aspect, provided herein are methods of reducing transactivation of at least one glucocorticoid response element in a subject in need thereof, comprising administering to the subject an effective amount of the compound of Formulae I-X or a pharmaceutically acceptable salt thereof.

In another aspect, provided herein are methods of inducing transrepression of at least one proinflammatory transcription factor and reducing transactivation of at least one glucocorticoid response element in a subject in need thereof, comprising administering to the subject an effective amount of the compound of Formulae I-X or a pharmaceutically acceptable salt thereof.

In another aspect, provided herein are methods of reducing at least one negative side-effect of a steroid as an ocular therapy in a subject in need thereof, comprising administering to the subject an effective amount of the compound of Formulae I-X or a pharmaceutically acceptable salt thereof.

In another aspect, provided herein are methods of maintaining intraocular pressure at or below about 21 mmHg in a subject in need thereof, comprising administering to the subject an effective amount of the compound of Formulae I-X or a pharmaceutically acceptable salt thereof.

In some embodiments of these methods, the compound of Formulae I-X or a pharmaceutically acceptable salt thereof is a compound of Table 1, Table 2, Table 3, Table 4, Table 5, Table 6, Table 7, Table 8, Table 9, or a pharmaceutically acceptable salt thereof.

In some embodiments of these methods, the cell is in a subject.

In some embodiments of these methods, the subject is a human.

In some embodiments of these methods, the administration is topical administration. In some embodiments, the topical administration is topical administration to an eye, or both eyes, of the subject.

In some embodiments, the topical administration is topical administration to an eyelid, or both eyelids, of the subject.

In some embodiments of these methods, the administration is ocular administration.

In some embodiments of these methods, the administration is systemic administration.

Administration/Dosage/Formulations

In another aspect, provided herein are compositions comprising a compound provided herein.

In another aspect, provided herein are pharmaceutical compositions comprising a compound provided herein and a pharmaceutically acceptable carrier.

Actual dosage levels of an active ingredient in the pharmaceutical compositions provided herein may be varied so as to obtain an amount of the active ingredient that is effective to achieve a desired therapeutic response for a particular subject, composition, or mode of administration, without being toxic to the subject.

In some embodiments, it is especially advantageous to formulate the compound in dosage unit form for ease of administration and uniformity of dosage. Dosage unit form as used herein refers to physically discrete units suited as unitary dosages for the subject to be treated; each unit containing a predetermined quantity of therapeutic compound calculated to produce the desired therapeutic effect in association with the required pharmaceutical vehicle. The dosage unit forms of the present disclosure are dictated by and directly dependent on (a) the unique characteristics of the therapeutic compound and the particular therapeutic effect to be achieved, and (b) the limitations inherent in the art of compounding/formulating such a therapeutic compound for the treatment of the diseases referred to herein in a subject in need thereof.

In one embodiment, the compounds or compositions provided herein are formulated using one or more pharmaceutically acceptable excipients or carriers. In one embodiment, the pharmaceutical compositions provided herein comprise a therapeutically effective amount of a compound provided herein and a pharmaceutically acceptable carrier.

In one embodiment, the present disclosure provides packaged pharmaceutical compositions comprising a container holding at least one therapeutically effective amount of a compound provided herein, and instructions for using the compound to treat one or more symptoms of a disease referred to herein in a subject in need thereof.

Routes of administration of any of the compositions provided herein include oral, nasal, rectal, intravaginal, parenteral, buccal, sublingual, topical, or ocular. The compounds for use as provided herein may be formulated for administration by any suitable route, such as for ocular, oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for ocular or intravesical administration and the like. It should be understood that the formulations and compositions that would be useful as provided herein are not limited to the particular formulations and compositions that are described herein.

Those skilled in the art will recognize, or be able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in reaction conditions, including but not limited to reaction times, reaction size or volume, and experimental reagents, such as solvents, catalysts, pressures, atmospheric conditions, e.g., nitrogen atmosphere, and reducing or oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

The following examples further illustrate aspects of the present disclosure. However, they are in no way a limitation of the teachings or present disclosure as set forth herein.

EXAMPLES

The present disclosure is now described with reference to the following Examples. These Examples are provided for the purpose of illustration only, and the present disclosure is not limited to these Examples, but rather encompasses all variations that are evident as a result of the teachings provided herein.

Example 1. Synthesis of 4-(3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate dihydrochloride 4-(3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate dihydrochloride (E5 2HCl) was prepared according to the synthetic scheme shown in FIG. 1.

Preparation of 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid (E2)

To a solution of dexamethasone in anhydrous pyridine was added DMAP and succinic anhydride. The reaction mixture was stirred overnight under $N_2$ at room temperature. The mixture was diluted with DI water then poured into EtOAc and HCl (1N). The organic layer was dried over $Na_2SO_4$, filtered and concentrated to give 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid with no further purification. (E2, 90%)

Preparation of 4-(3-((tert-butoxycarbonyl)amino)-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate (E4)

To a solution of 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid (E2) in anhydrous pyridine was added EDC, DMAP and tert-butyl (2-(4-(hydroxymethyl)phenyl)-3-(isoquinolin-6-ylamino)-3-oxopropyl)carbamate (E3) and the solution was stirred under $N_2$ at room temperature overnight. The reaction was poured into EtOAc/NaHCO$_3$ (sat) and extracted with EtOAc, dried over Na$_2$SO$_4$, filtered and concentrated. Column chromatography 0-5% MeOH/CH$_2$Cl$_2$ gave pure 4-(3-((tert-butoxycarbonyl)amino)-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate (E4, 64%).

Preparation of 4-(3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate dihydrochloride (E5 2HCl)

To a solution of 4-(3-((tert-butoxycarbonyl)amino)-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate (E4) in CH$_2$Cl$_2$ was added 4M HCl solution in dioxane. The reaction was stirred at room temperature for 3 hours then the precipitate was filtered and washed with CH$_2$Cl$_2$ to isolate pure 4-(3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) succinate dihydrochloride (E5 2HCl, 95%).

Using commercially available compounds and largely the procedures set forth in E2-E5 and substituting the appropriate starting materials, E2-E42 (Table 2) were made and E43-E62 (Table 3) are likewise synthesized.

TABLE 2

| Example number | Structure | Molecular Weight (g/mol) |
|---|---|---|
| 2 | 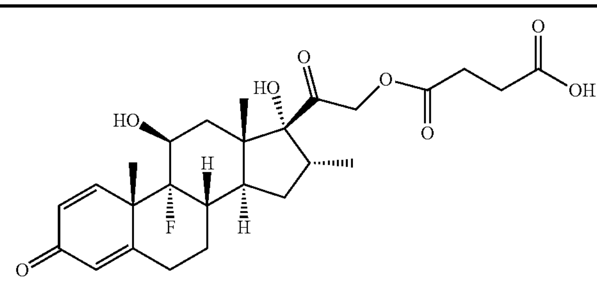 | 492.54 |

TABLE 2-continued

| Example number | Structure | Molecular Weight (g/mol) |
|---|---|---|
| 4 | 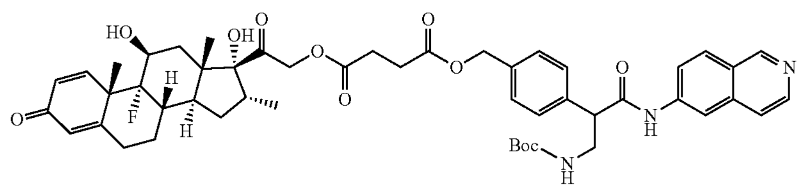 | 896.02 |
| 5 | 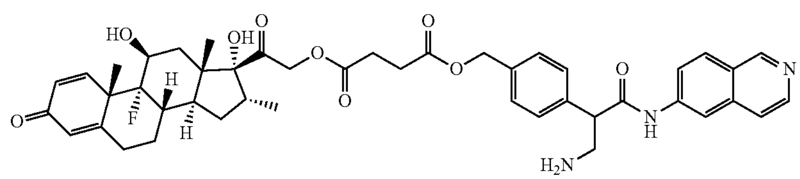 | 795.91 |
| 6 | 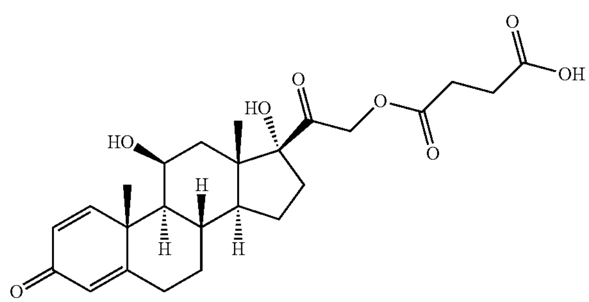 | 460.42 |
| 7 | 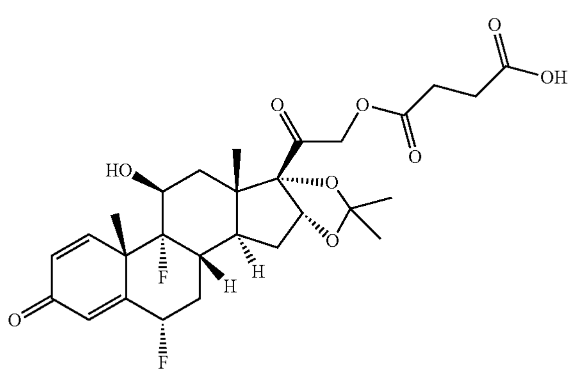 | 552.57 |
| 8 | 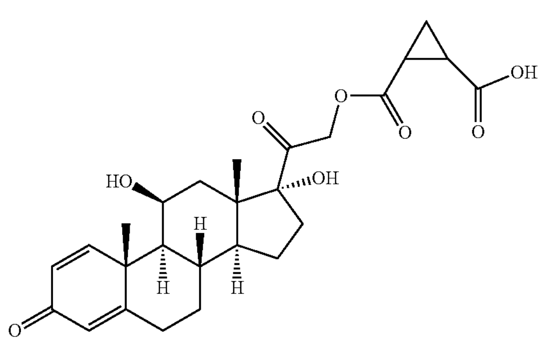 | 472.53 |

TABLE 2-continued

| Example number | Structure | Molecular Weight (g/mol) |
|---|---|---|
| 9 | 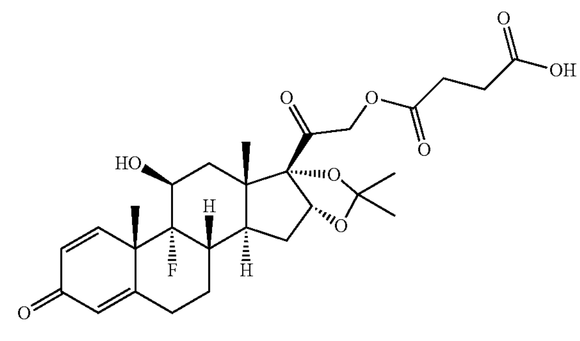 | 534.58 |
| 10 | 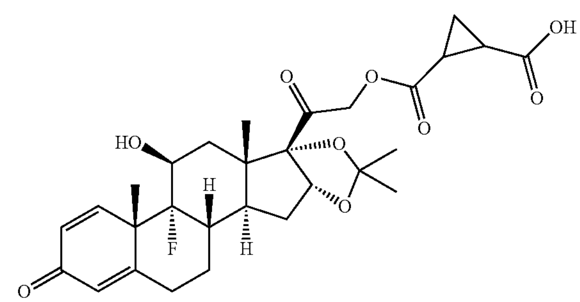 | 546.59 |
| 11 | 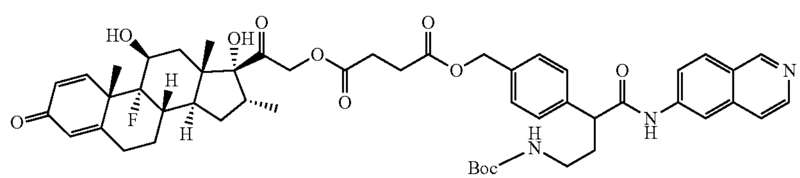 | 910.05 |
| 12 | 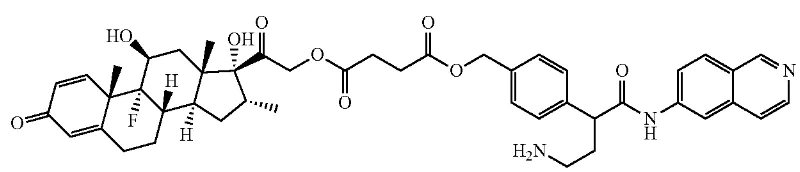 | 809.93 |
| 13 | 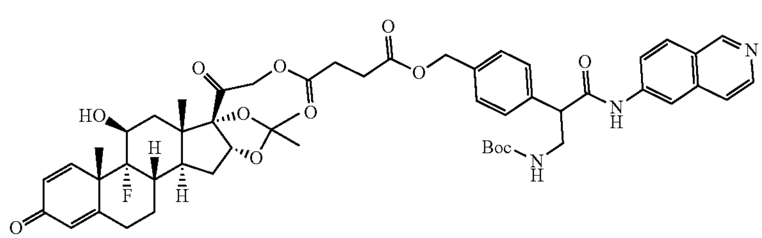 | 938.06 |
| 14 | 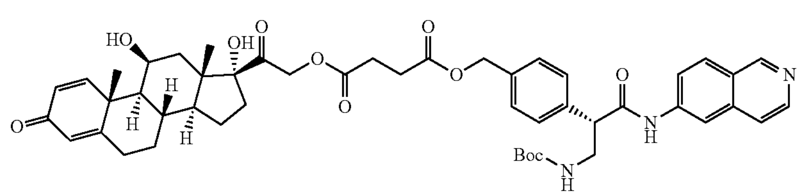 | 864.01 |

TABLE 2-continued

| Example number | Structure | Molecular Weight (g/mol) |
|---|---|---|
| 15 | 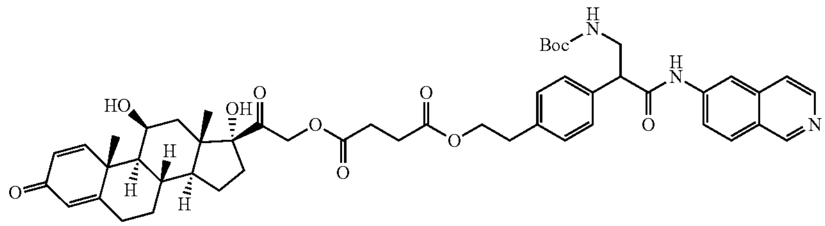 | 878.03 |
| 16 | 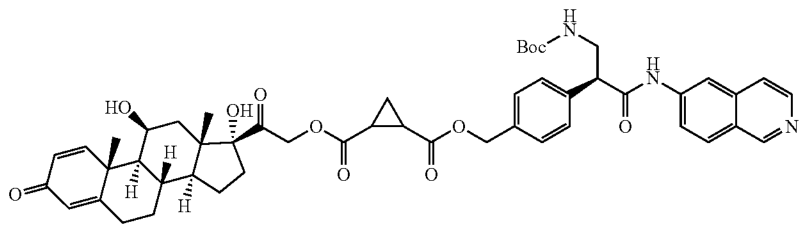 | 876.02 |
| 17 | 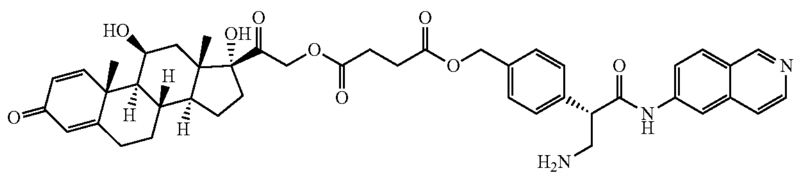 | 763.89 |
| 18 | 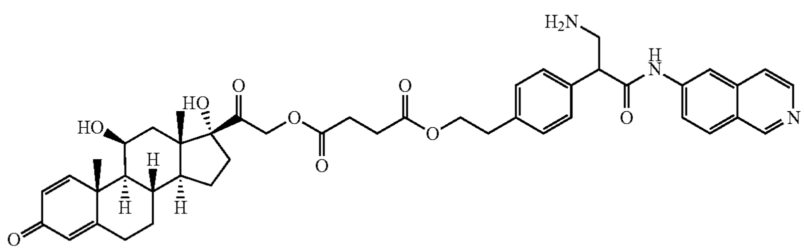 | 777.92 |
| 19 | 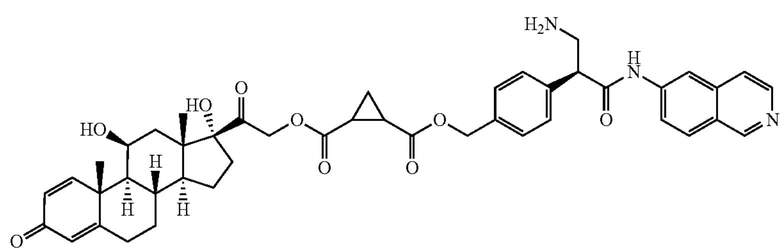 | 775.90 |
| 20 | 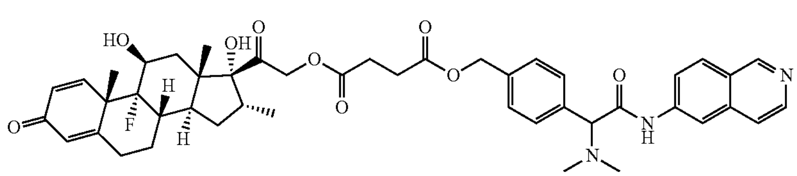 | 809.93 |
| 21 | 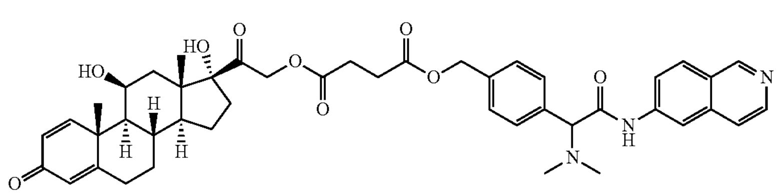 | 777.92 |

TABLE 2-continued

| Example number | Structure | Molecular Weight (g/mol) |
|---|---|---|
| 22 | 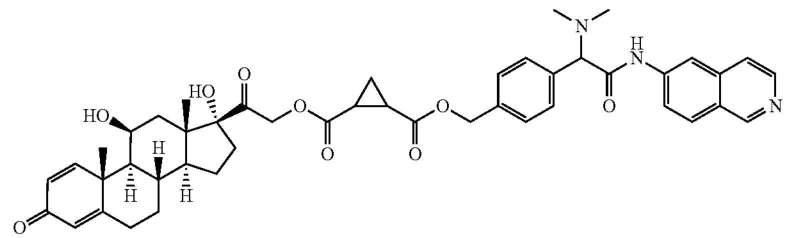 | 789.93 |
| 23 | 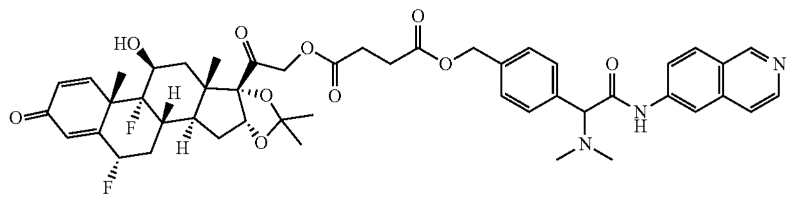 | 869.96 |
| 24 | 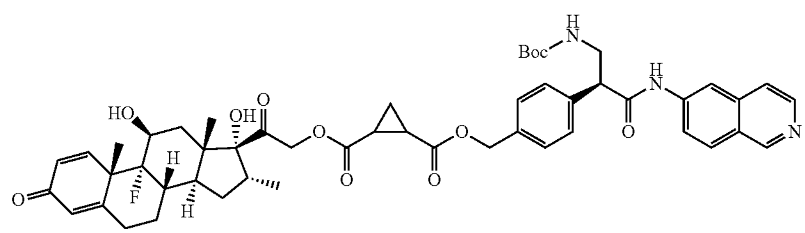 | 908.03 |
| 25 | 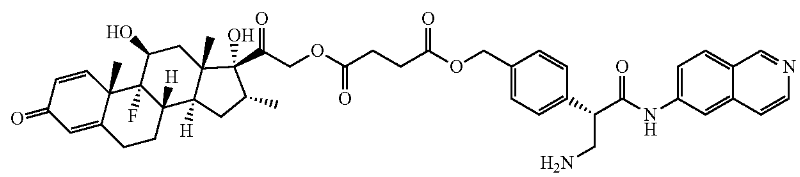 | 795.91 |
| 26 | 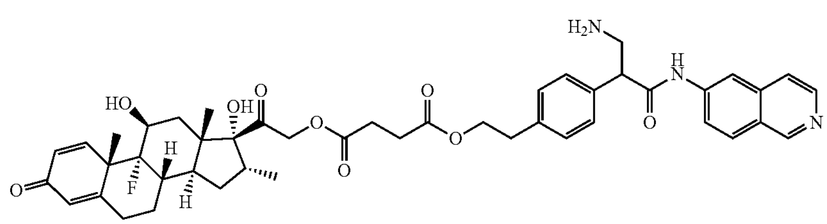 | 809.93 |
| 27 | 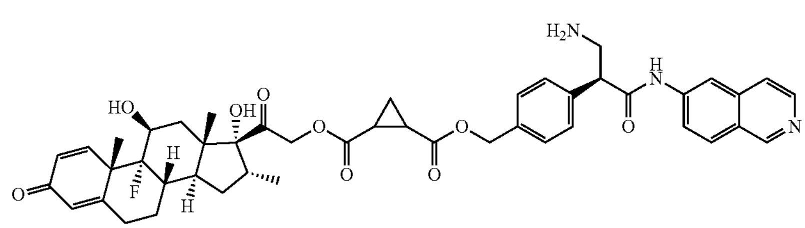 | 807.92 |
| 28 | 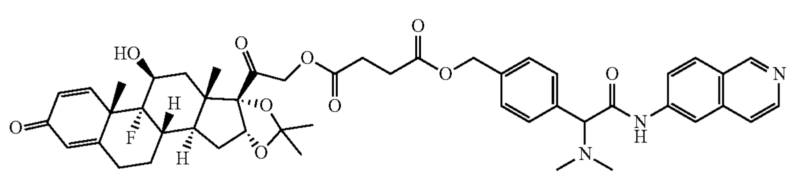 | 851.97 |

TABLE 2-continued

| Example number | Structure | Molecular Weight (g/mol) |
|---|---|---|
| 29 | 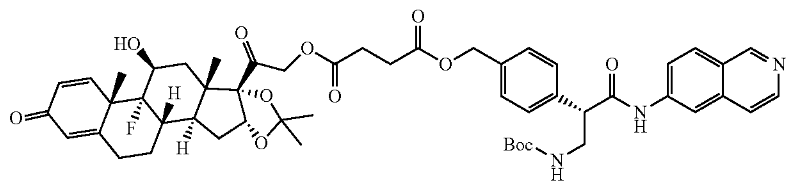 | 938.06 |
| 30 | 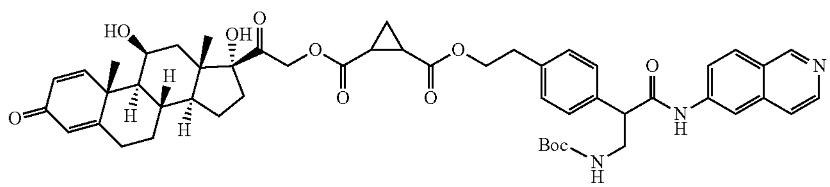 | 890.04 |
| 31 | 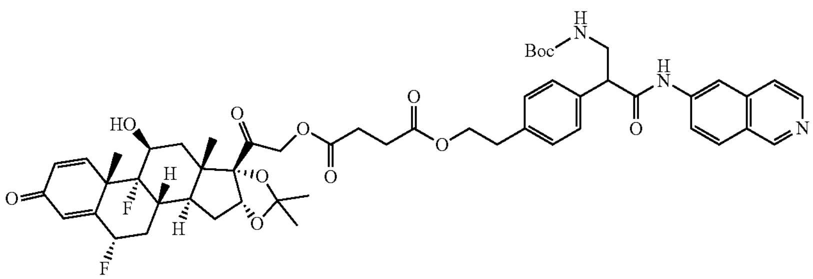 | 970.08 |
| 32 | 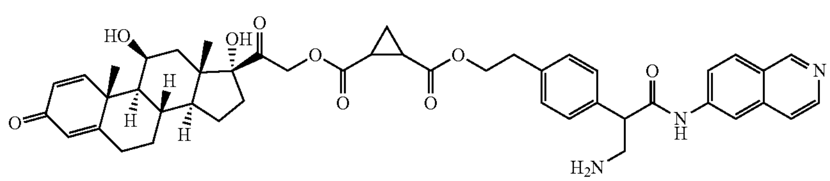 | 789.93 |
| 33 | 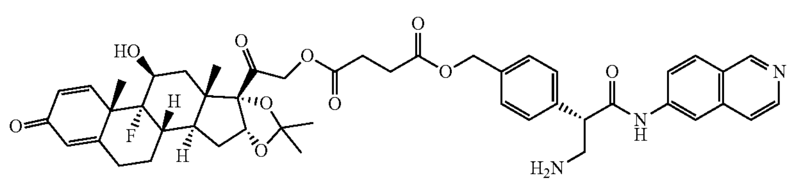 | 837.94 |
| 34 | 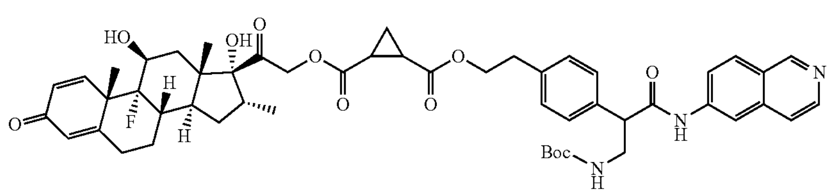 | 922.06 |
| 35 | 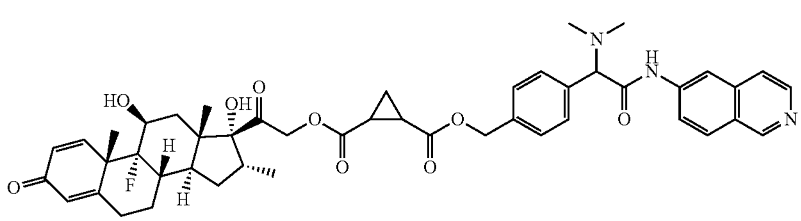 | 821.94 |

TABLE 2-continued

| Example number | Structure | Molecular Weight (g/mol) |
| --- | --- | --- |
| 36 | 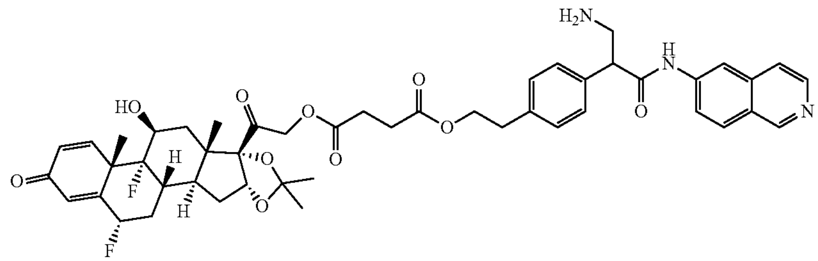 | 869.96 |
| 37 | 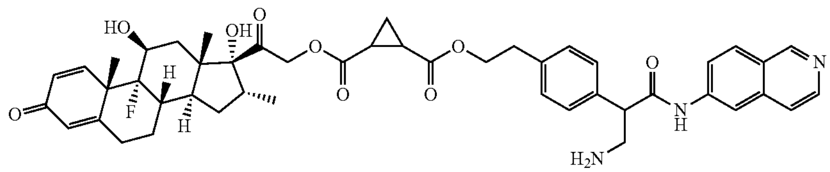 | 821.94 |
| 38 | 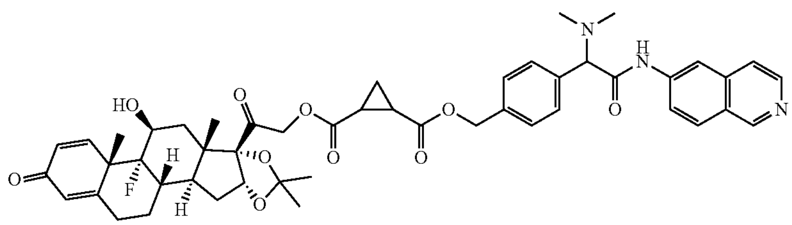 | 863.98 |
| 39 | 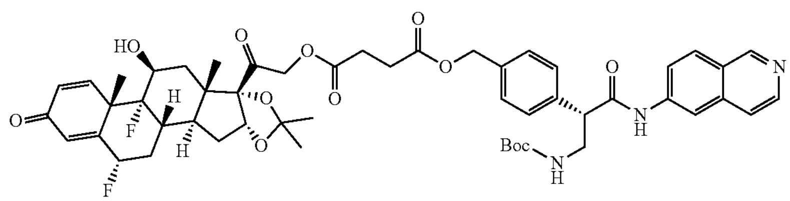 | 956.05 |
| 40 | 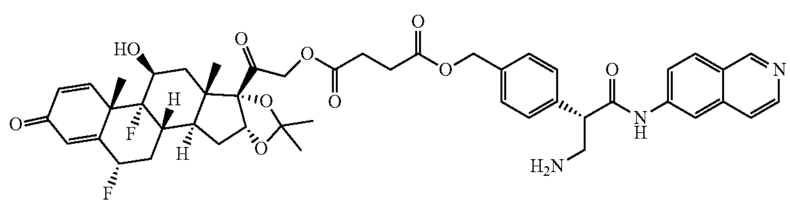 | 855.93 |
| 41 | 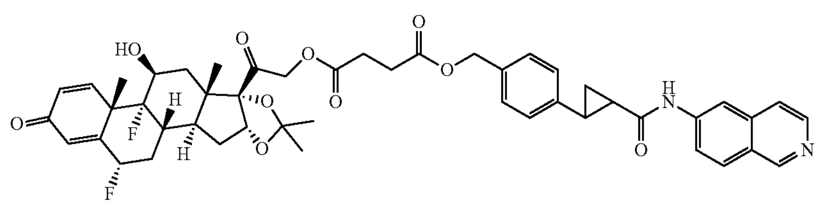 | 852.93 |
| 42 | 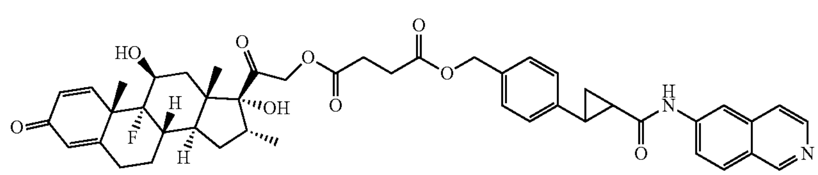 | 792.90 |

TABLE 3
| Example | Structure |
|---|---|
| 43 | 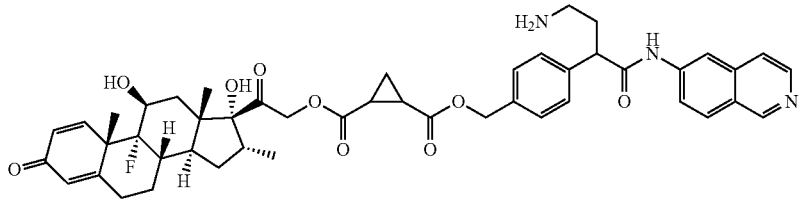 |
| 44 | 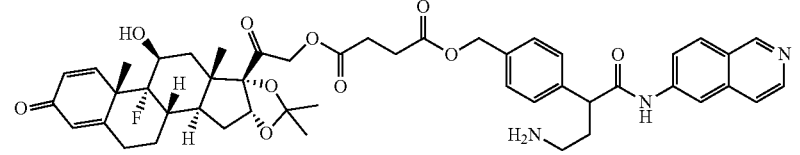 |
| 45 | 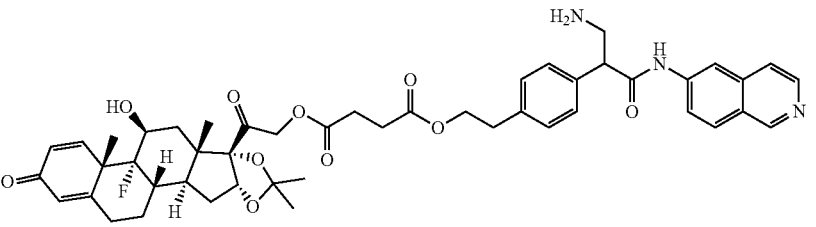 |
| 46 | 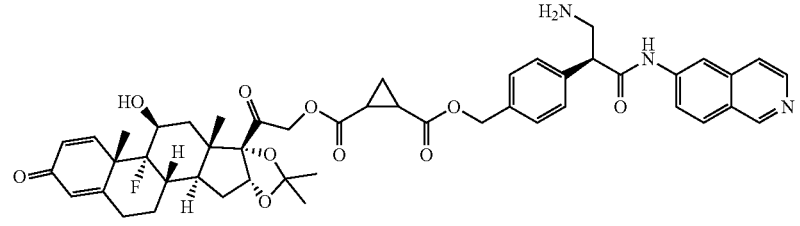 |
| 47 | 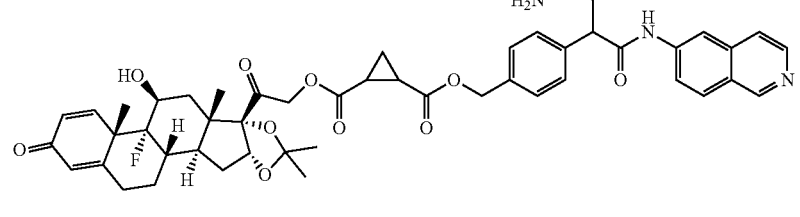 |
| 48 | 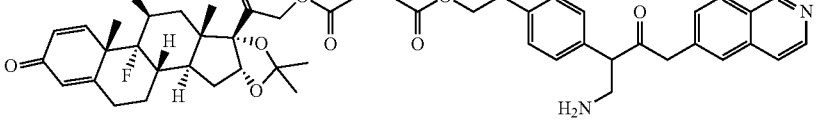 |
| 49 | 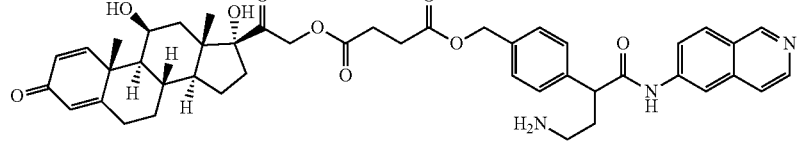 |

TABLE 3-continued
| Example | Structure |
|---|---|
| 50 | 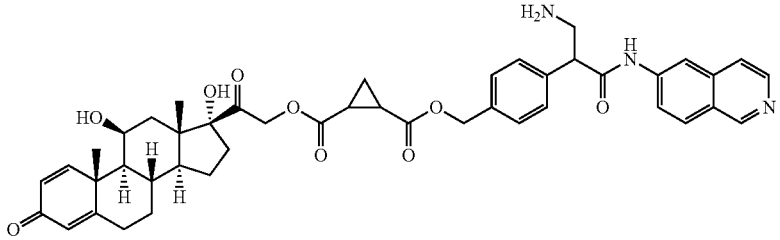 |
| 51 | 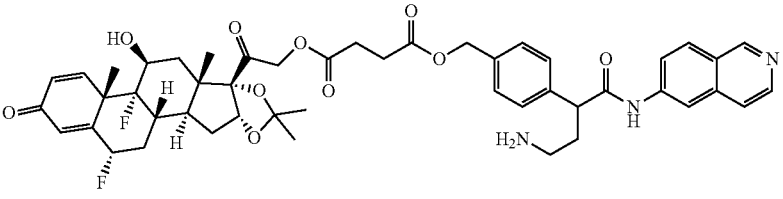 |
| 52 | 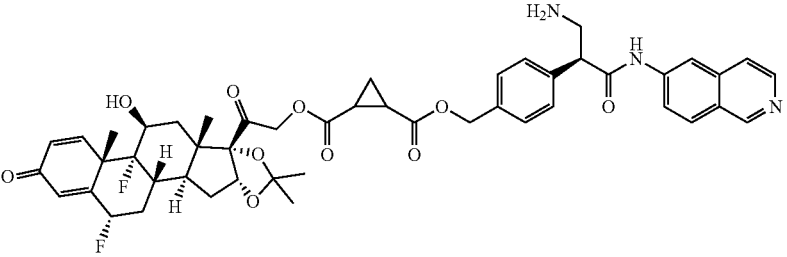 |
| 53 | 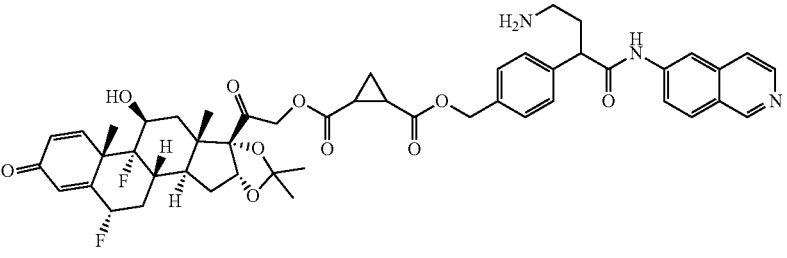 |
| 54 | 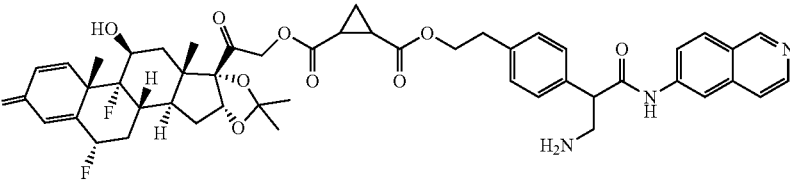 |
| 55 | 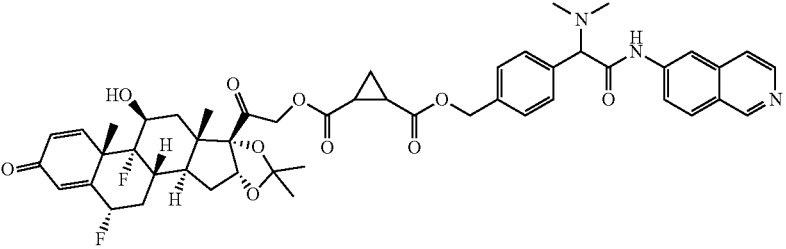 |

TABLE 3-continued
| Example | Structure |
|---|---|
| 56 | 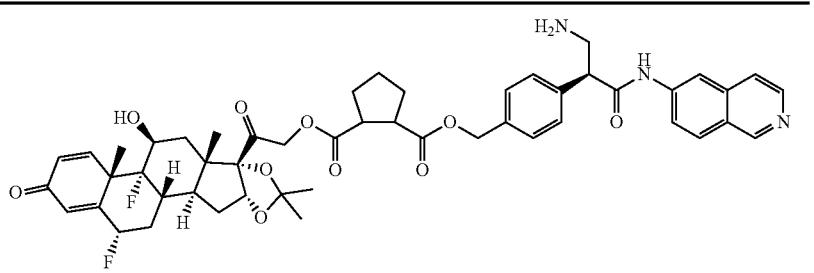 |
| 57 | 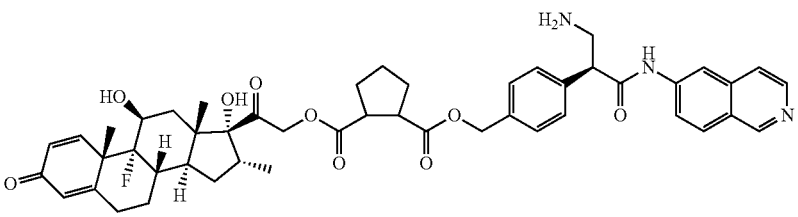 |
| 58 | 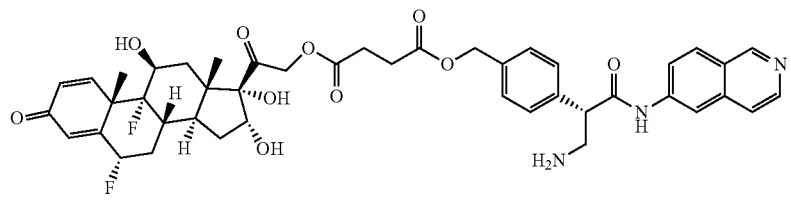 |
| 59 | 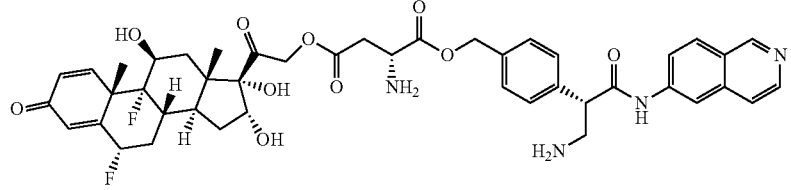 |
| 60 | 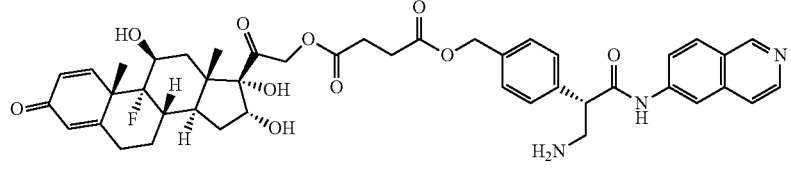 |
| 61 | 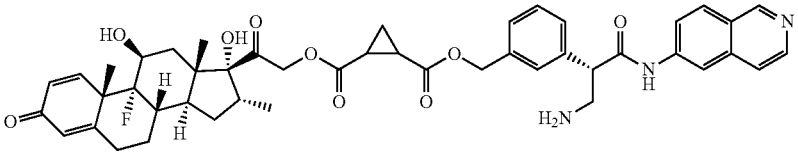 |
| 62 | 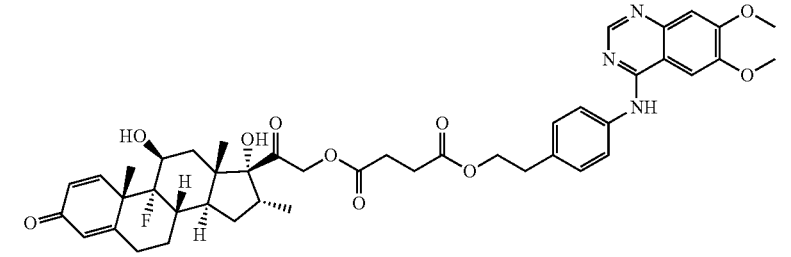 |

TABLE 3-continued

| Example | Structure |
|---|---|
| 95 | 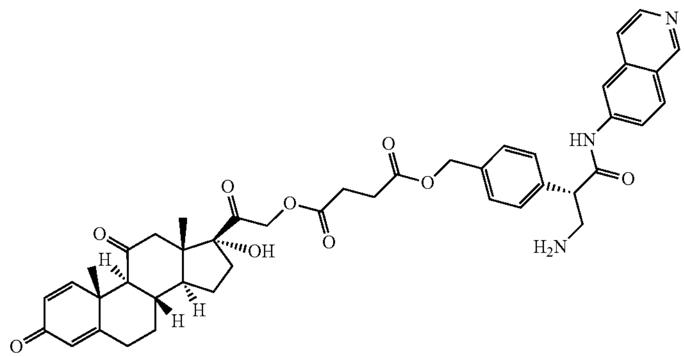 [SMILES: C[C@]12C=CC(=O)C=C1CC[C@@H]1[C@@H]2C(=O)C[C@@]2(C)[C@H]1CC[C@]2(O)C(=O)COC(=O)CCC(=O)OCc1ccc([C@@H](CN)C(=O)Nc2ccc3cnccc3c2)cc1] |
| 96 | 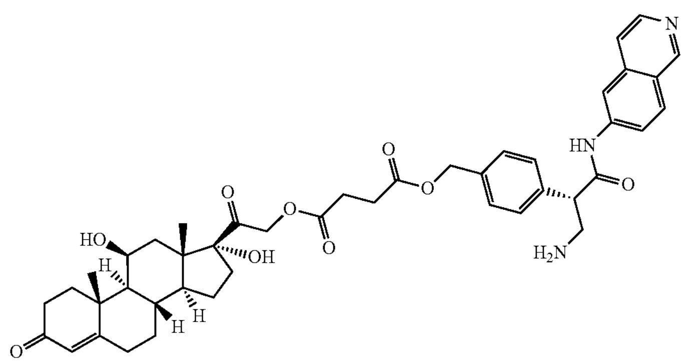 [SMILES: C[C@]12CCC(=O)C=C1CC[C@@H]1[C@@H]2[C@@H](O)C[C@@]2(C)[C@H]1CC[C@]2(O)C(=O)COC(=O)CCC(=O)OCc1ccc([C@@H](CN)C(=O)Nc2ccc3cnccc3c2)cc1] |
| 97 | 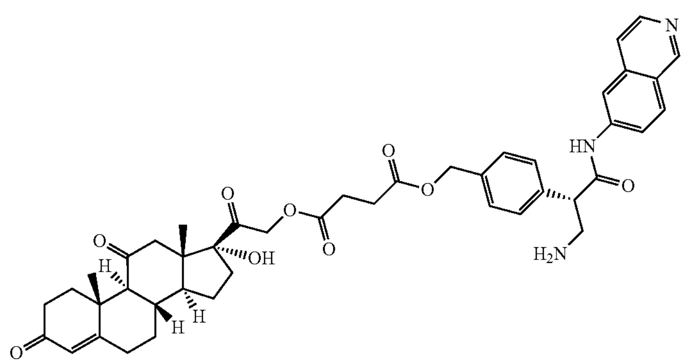 [SMILES: C[C@]12CCC(=O)C=C1CC[C@@H]1[C@@H]2C(=O)C[C@@]2(C)[C@H]1CC[C@]2(O)C(=O)COC(=O)CCC(=O)OCc1ccc([C@@H](CN)C(=O)Nc2ccc3cnccc3c2)cc1] |

Figure 2:
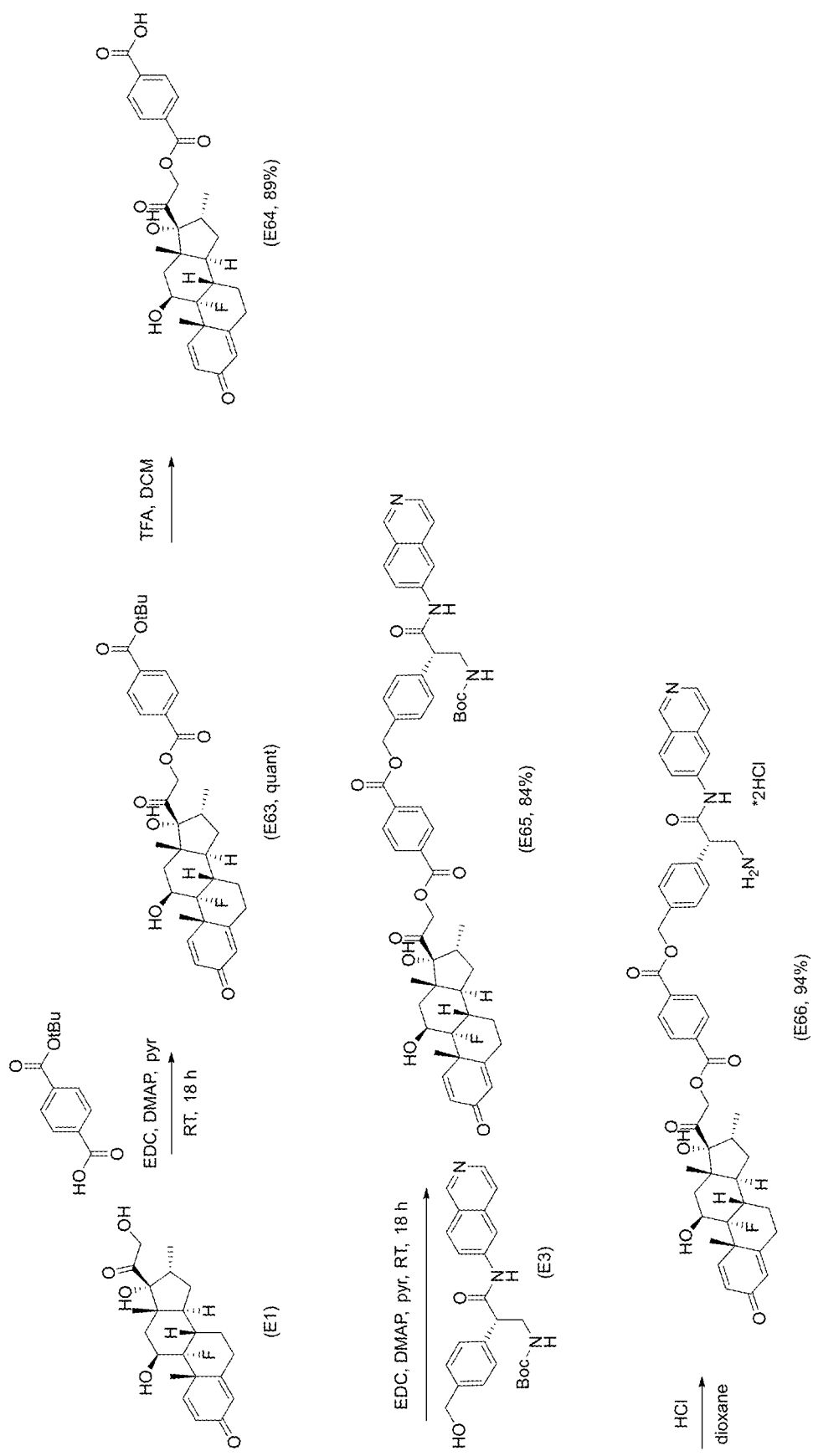
FIG. 2 shows a synthetic scheme for the synthesis of 4-((S)-3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate dihydrochloride (E66 2HCl).

Example 2. Synthesis of 4-((S)-3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate dihydrochloride 4-((S)-3-amino-1-(isoquinolin-6-ylamino)-1-oxopropan-2-yl)benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate dihydrochloride (E66 2HCl) was prepared according to the synthetic scheme shown in FIG. 2.

Preparation of tert-butyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E63)

To a solution of dexamethasone (E1) in anhydrous pyridine was added EDC, DMAP and 4-(tert-butoxycarbonyl)benzoic acid and the solution was stirred under $N_2$ at room temperature overnight. The reaction was poured into EtOAc/NaHCO$_3$ (sat) and extracted with EtOAc, dried over Na$_2$SO$_4$, filtered and concentrated. Column chromatography 0-3% MeOH/CH$_2$Cl$_2$ gave pure tert-butyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E63, quantitative yield).

Preparation of 4-((2-((8S,9R,10S,11S,13S,14S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy) carbonyl) benzoic acid (E64)

To a solution of tert-butyl (2-((8S,9R,10S,11S,13S,14S, 16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E63) in CH$_2$Cl$_2$ was added trifluoroacetic acid and the solution was stirred at room temperature overnight. The reaction mixture was poured over DI water and extracted with EtOAc to give pure 4-((2-((8S,9R,10S,11S,13S,14S, 16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)carbonyl) benzoic acid (E64, 89%).

Preparation of 4-((S)-3-((tert-butoxycarbonyl) amino)-1-(isoquinolin-6-ylamino)-1-oxopropan-2-yl) benzyl (2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E65)

To a solution of 4-((2-((8S,9R,10S,11S,13S,14S,16R, 17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)carbonyl)benzoic acid (E64) in anhydrous pyridine was added EDC, DMAP and tert-butyl (S)-(2-(4-(hydroxymethyl)phenyl)-3-(isoquinolin-6-ylamino)-3-oxopropyl)carbamate (E3) acid and the solution was stirred under N$_2$ at room temperature overnight. The reaction was poured into EtOAc/NaHCO$_3$ (sat) and extracted with EtOAc, dried over Na$_2$SO$_4$, filtered and concentrated. Column chromatography 0-5% MeOH/ CH$_2$Cl$_2$ gave pure 4-((S)-3-((tert-butoxycarbonyl)amino)-1-(isoquinolin-6-ylamino)-1-oxopropan-2-yl)benzyl (2-((8S, 9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E65, 84%).

Preparation of 4-((S)-3-amino-1-(isoquinolin-6-ylamino)-1-oxopropan-2-yl)benzyl (2-((8S,9R,10S, 11S,13S,14S,16R,17R)-9-fluoro-11,17-dihydroxy-10,13,16-trimethyl-3-oxo-6,7,8,9,10,11,12,13,14,15, 16,17-dodecahydro-3H-cyclopenta[a]phenanthren-17-yl)-2-oxoethyl) terephthalate dihydrochloride (E66 2HCl)

To a solution of 4-((S)-3-((tert-butoxycarbonyl)amino)-1-(isoquinolin-6-ylamino)-1-oxopropan-2-yl)benzyl (2-((8S, 9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) terephthalate (E65) in CH$_2$Cl$_2$ was added 4M HCl solution in dioxane. The reaction was stirred at room temperature for 4 hours then the precipitate was filtered and washed with CH$_2$Cl$_2$ to isolate pure 4-((S)-3-amino-1-(isoquinolin-6-ylamino)-1-oxopropan-2-yl)benzyl (2-((8S,9R, 10S,11S,13S,14S,16R,17R)-9-fluoro-11,17-dihydroxy-10, 13,16-trimethyl-3-oxo-6,7,8,9,10,11,12,13,14,15,16,17-dodecahydro-3H-cyclopenta[a]phenanthren-17-yl)-2-oxoethyl) terephthalate dihydrochloride (E66 2HCl, 94%).

Using commercially available compounds and largely the procedures set forth in E2-E5 and substituting the appropriate starting materials, E63-E66 (Table 4) were made and E67-E78 (Table 5) are likewise synthesized.

TABLE 4

| Example | Structure |
| --- | --- |
| 63 | 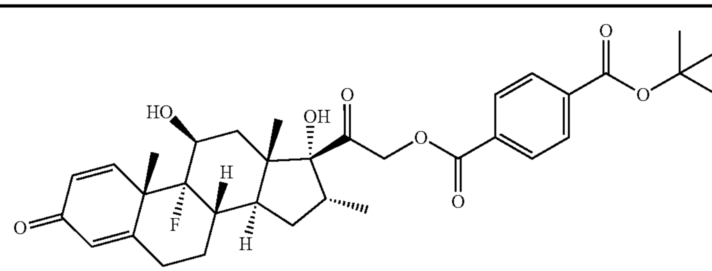 |
| 64 | 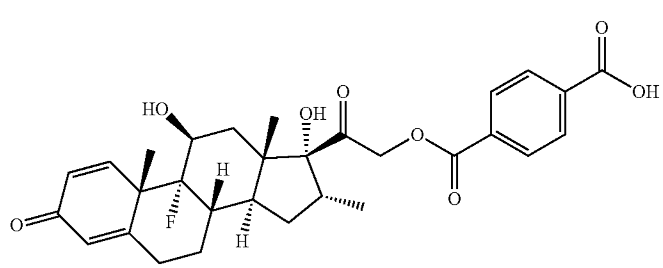 |

TABLE 4-continued

| Example | Structure |
|---------|-----------|
| 65 | 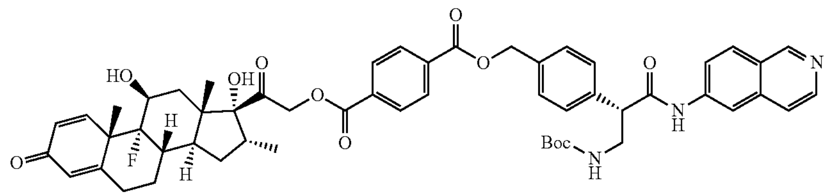 |
| 66 | 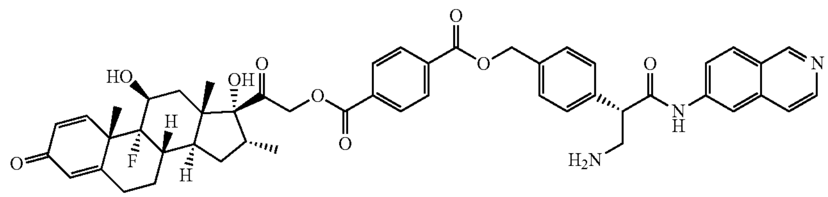 |

TABLE 5

| Example | Structure |
|---------|-----------|
| 67 | 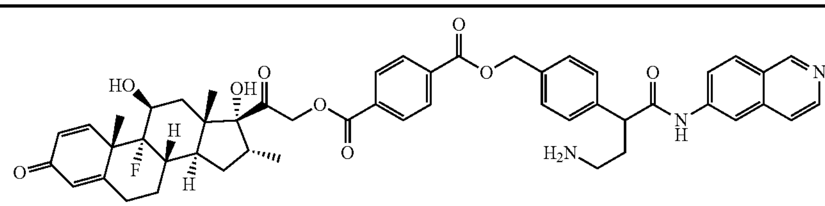 |
| 68 | 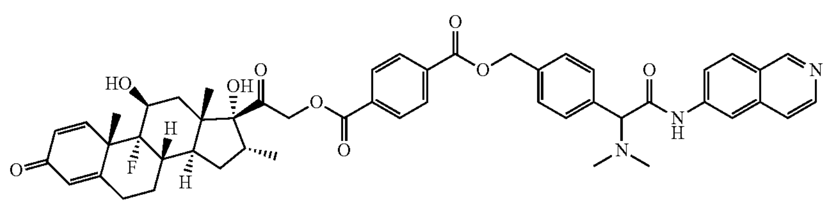 |
| 69 | 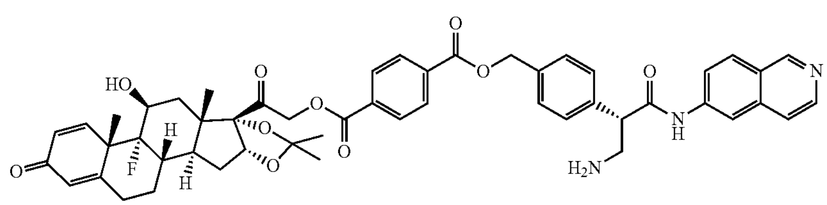 |
| 70 | 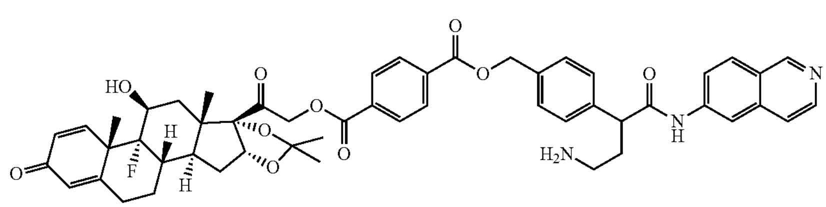 |
| 71 | 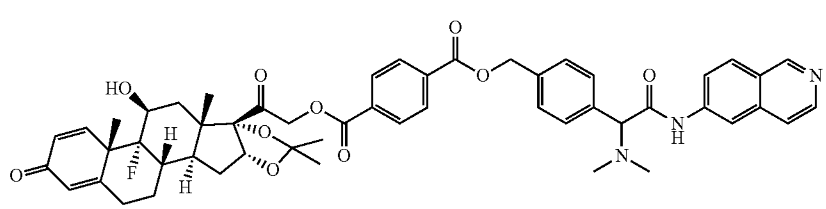 |

| Example | Structure |
|---|---|
| 72 | 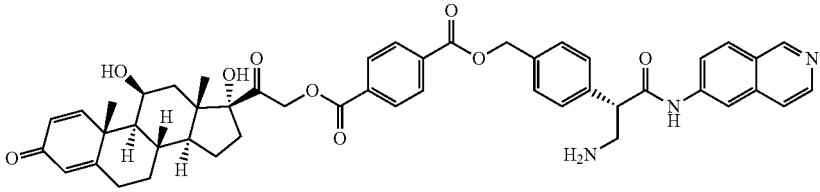 |
| 73 | 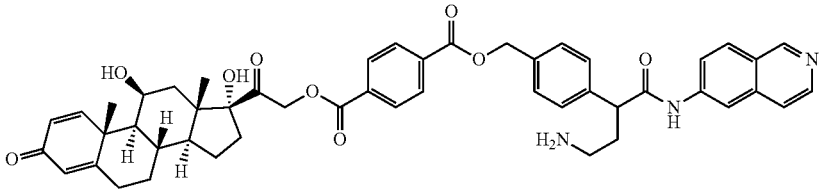 |
| 74 | 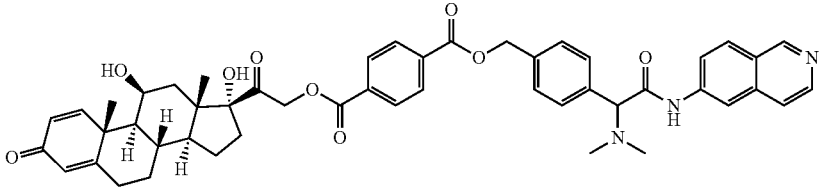 |
| 75 | 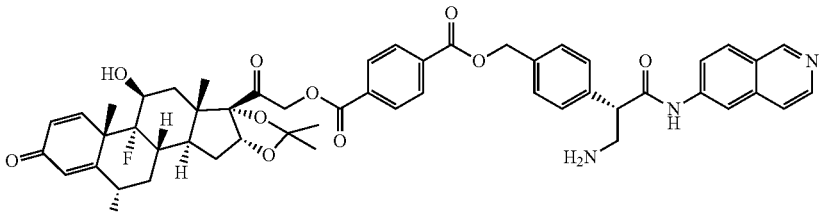 |
| 76 | 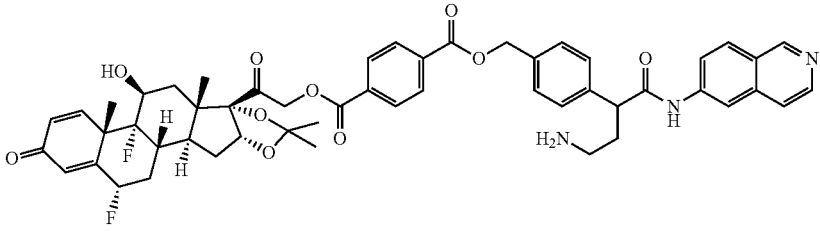 |
| 77 | 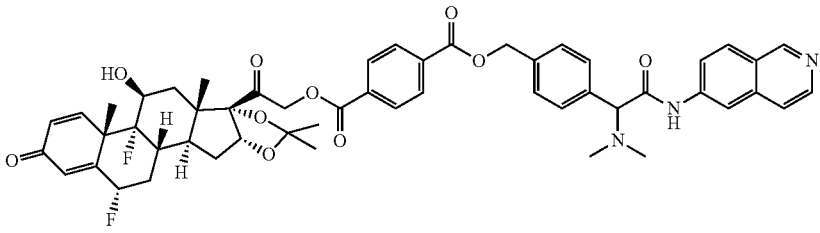 |
| 78 | 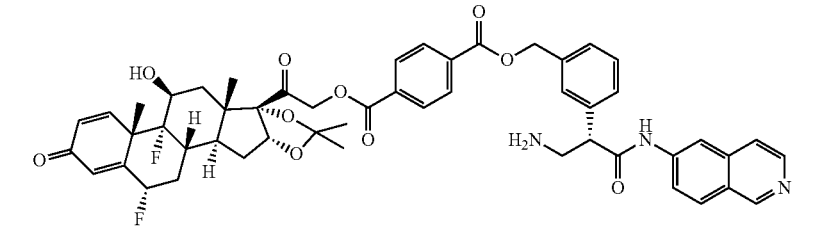 |

Figure 3:
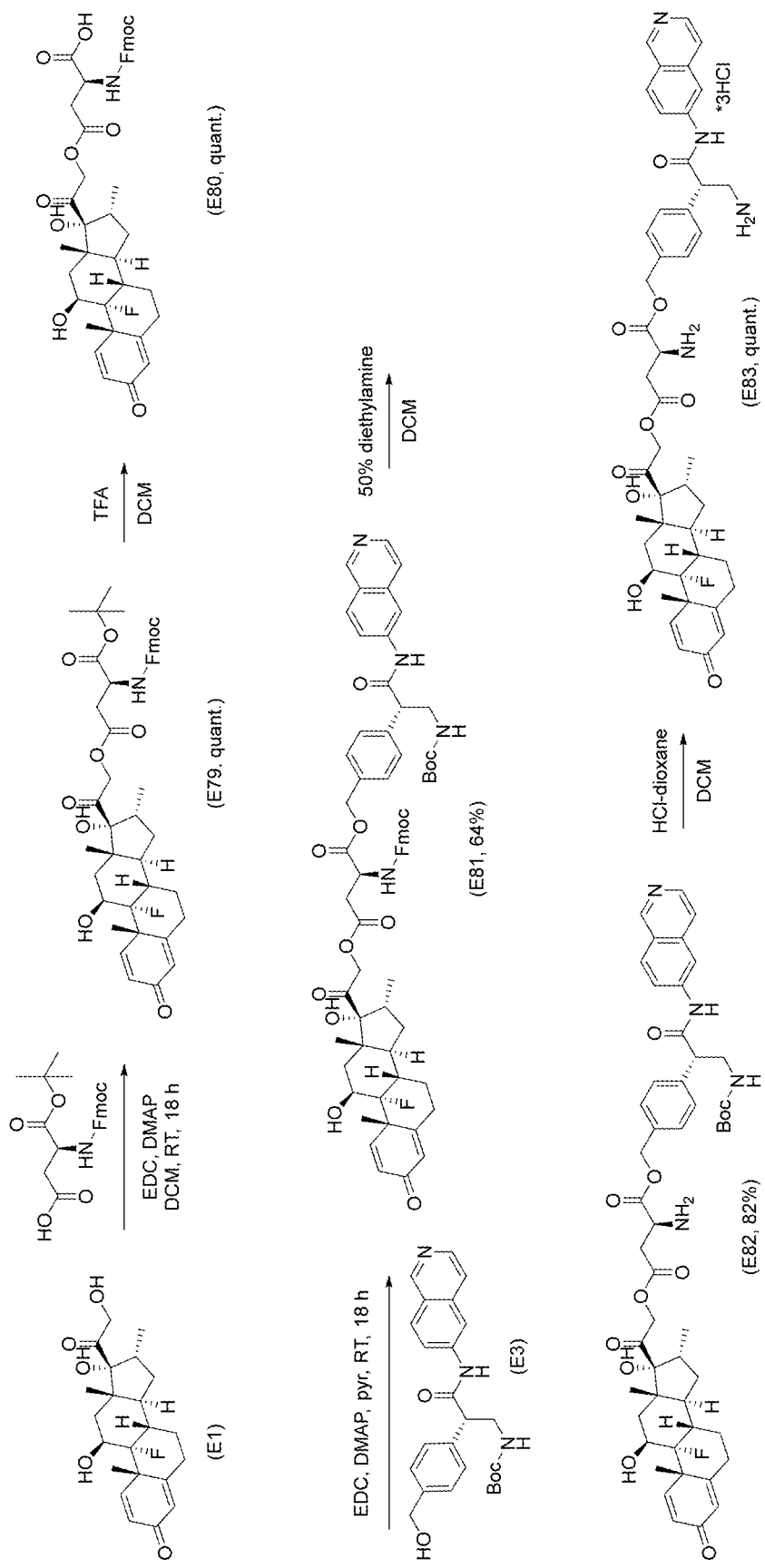
FIG. 3 shows a synthetic scheme for the synthesis of 1-(4-((S)-3-amino-1-(isoquinolin-6-ylamino)-1-oxopropan-2-yl)benzyl) 4-(2-((8S,9R,10S,11S,13S,14S,16S,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate trihydrochloride (E83 3HCl).

Example 3. Synthesis of 1-(4-((S)-3-amino-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate trihydrochloride 1-(4-((S)-3-amino-1-(isoquinolin-6-ylamino)-1-oxopropan-2-yl)benzyl) 4-(2-((8S,9R,10S,11S,3S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate trihydrochloride (E83 3HCl) was prepared according to the synthetic scheme shown in FIG. 3.

Preparation of 1-(tert-butyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl)methoxy)carbonyl)-L-aspartate (E79)

To a solution of dexamethasone (E1) in anhydrous $CH_2Cl_2$ was added EDC, DMAP and (S)-3-((((9H-fluoren-9-yl)methoxy)carbonyl)amino)-4-(tert-butoxy)-4-oxobutanoic acid and the solution was stirred under $N_2$ at room temperature overnight. The reaction was poured into EtOAc/NaHCO$_3$ (sat) and extracted with EtOAc, dried over $Na_2SO_4$, filtered and concentrated. Column chromatography 0-5% MeOH/CH$_2$Cl$_2$ gave pure 1-(tert-butyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl)methoxy)carbonyl)-L-aspartate (E79, quantitative yield).

Preparation of (S)-2-((((9H-fluoren-9-yl) methoxy)carbonyl)amino)-4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid (E80)

To a solution of 1-(tert-butyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl) methoxy)carbonyl)-L-aspartate (E79) in CH$_2$Cl$_2$ was added trifluoroacetic acid and the solution was stirred at room temperature overnight. The reaction mixture was poured over DI water and extracted with EtOAc to give pure (S)-2-((((9H-fluoren-9-yl)methoxy)carbonyl)amino)-4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid (E80, quantitative yield).

Preparation of 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl) methoxy)carbonyl)-L-aspartate (E81)

To a solution of (S)-2-((((9H-fluoren-9-yl)methoxy)carbonyl)amino)-4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethoxy)-4-oxobutanoic acid (E80) in anhydrous pyridine was added EDC, DMAP and tert-butyl (S)-(2-(4-(hydroxymethyl)phenyl)-3-(isoquinolin-6-ylamino)-3-oxopropyl)carbamate (E3) acid and the solution was stirred under $N_2$ at room temperature overnight. The reaction was poured into EtOAc/NaHCO$_3$ (sat) and extracted with EtOAc, dried over $Na_2SO_4$, filtered and concentrated. Column chromatography 0-5% MeOH/CH$_2$Cl$_2$ gave pure 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl)methoxy)carbonyl)-L-aspartate (E81, 64%).

Preparation of 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate (E82)

To a solution of 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) (((9H-fluoren-9-yl)methoxy)carbonyl)-L-aspartate (E81) in CH$_2$Cl$_2$ was added a solution of diethylamine in CH$_2$Cl$_2$ and the solution was stirred at room temperature for 5 hours. The reaction was poured into EtOAc/NaHCO$_3$ (sat) and extracted with EtOAc, dried over Na$_2$SO$_4$, filtered and concentrated. Column chromatography 0-5% MeOH/CH$_2$Cl$_2$ gave pure 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate (E82, 82%).

Preparation of 1-(4-((S)-3-amino-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate (E83)

To a solution of 1-(4-((S)-3-((tert-butoxycarbonyl)amino)-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate (E82) in CH$_2$Cl$_2$ was added 4M HCl solution in dioxane. The reaction was stirred at room temperature for 2 hours then the precipitate was filtered and washed with CH$_2$Cl$_2$ to isolate pure 1-(4-((S)-3-amino-1-(isoquinolin-6-ylamino)-1-oxopropan-2-yl)benzyl) 4-(2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl) L-aspartate trihydrochloride (E83 3HCl, quantitative yield).

Using commercially available compounds and largely the procedures set forth in E2-E5 and substituting the appropriate starting materials, E79-E86 (Table 6) were made and E87-E89 (Table 7) are likewise synthesized.

TABLE 6
| Example | Structure |
|---|---|
| 79 | 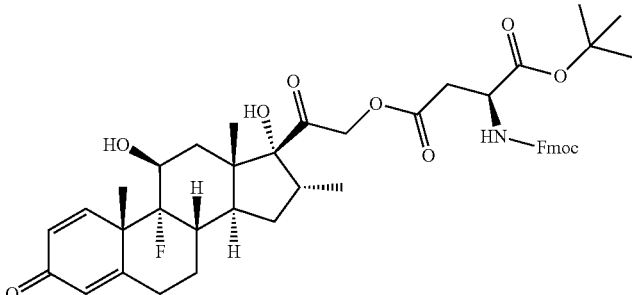 |
| 80 | 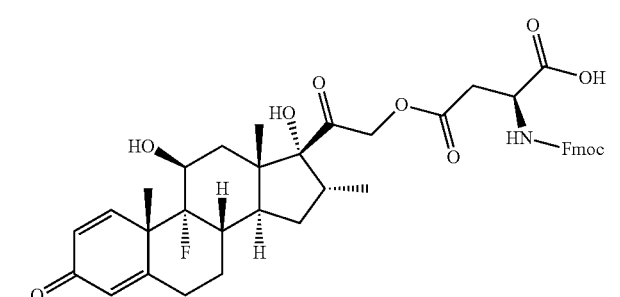 |
| 81 | 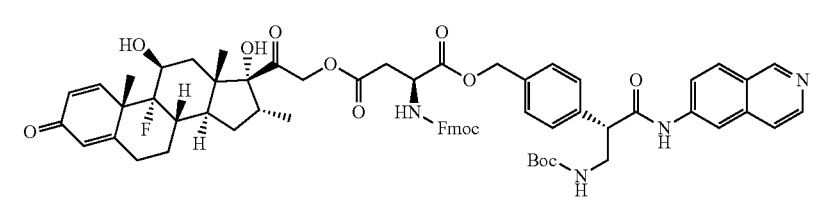 |
| 82 | 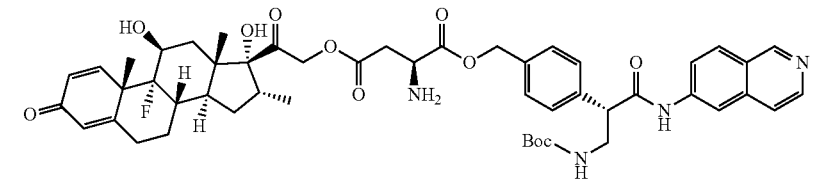 |
| 83 | 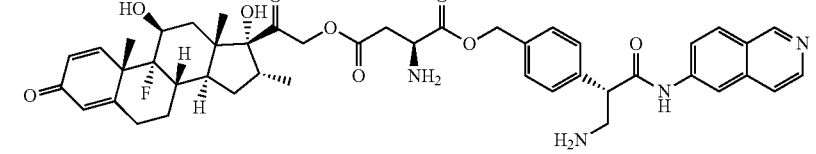 |
| 84 | 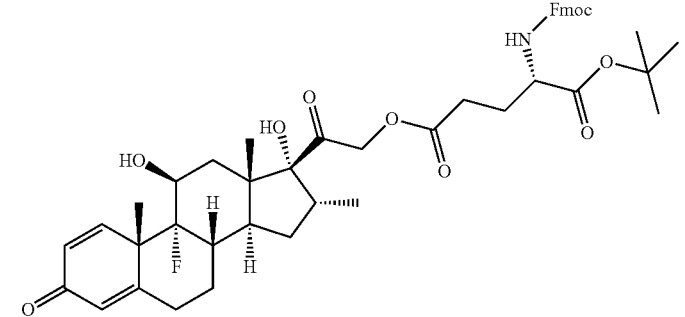 |

TABLE 6-continued

| Example | Structure |
|---------|-----------|
| 85 | 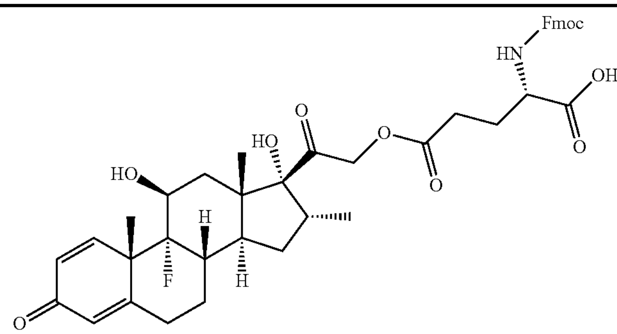 |
| 86 | 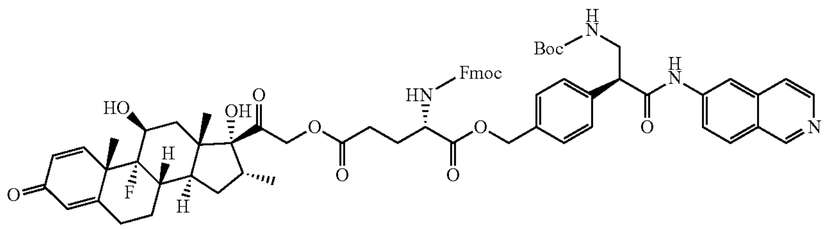 |

TABLE 7

| Example | Structure |
|---------|-----------|
| 87 | 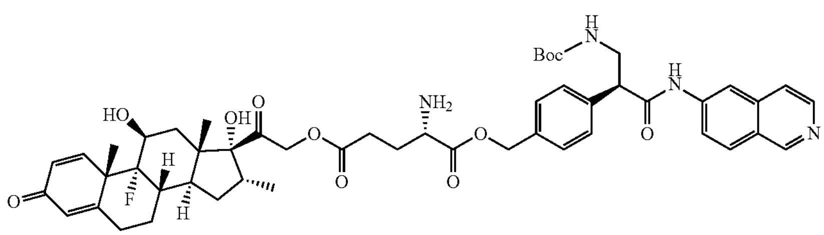 |
| 88 | 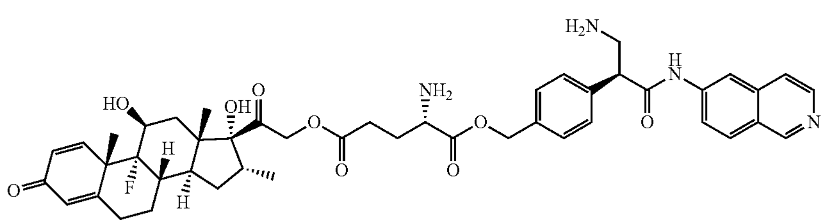 |
| 89 | 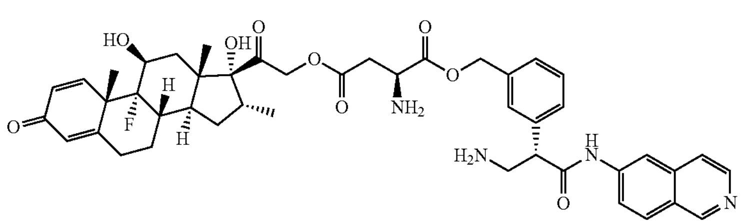 |

Figure 4:
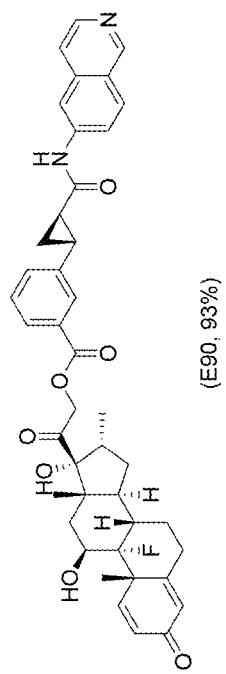
FIG. 4 shows a synthetic scheme for the synthesis of 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 3-((1R,2R)-2-(isoquinolin-6-ylcarbamoyl)cyclopropyl)benzoate (E90).
Figure 4:
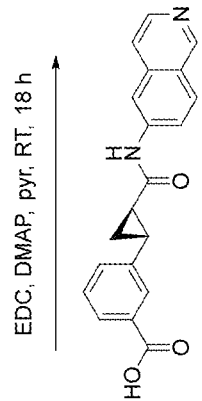
Figure 4:
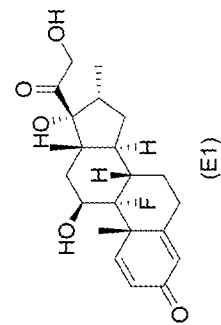

Example 4. Synthesis of 2-((8S,9R,10S,11S,13S, 14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 3-((1R,2R)-2-(isoquinolin-6-ylcarbamoyl)cyclopropyl)benzoate 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 3-((1R,2R)-2-(isoquinolin-6-ylcarbamoyl)cyclopropyl)benzoate (E90) was prepared according to the synthetic scheme shown in FIG. 4.

To a solution of dexamethasone (E1) in anhydrous pyridine was added EDC, DMAP and 3-((1R,2R)-2-(isoquinolin-6-ylcarbamoyl) cyclopropyl)benzoic acid and the solution was stirred under $N_2$ at room temperature overnight. The reaction was poured into EtOAc/NaHCO$_3$ (sat) and extracted with EtOAc, dried over Na$_2$SO$_4$, filtered and concentrated. Column chromatography 0-5% MeOH/CH$_2$Cl$_2$ gave pure 2-((8S,9R,10S,11S,13S,14S,16R,17R)-9-fluoro-11,17-dihydroxy-10,13,16-trimethyl-3-oxo-6,7,8,9,10,11,12,13,14,15,16,17-dodecahydro-3H-cyclopenta[a]phenanthren-17-yl)-2-oxoethyl 3-((1R,2R)-2-(isoquinolin-6-ylcarbamoyl)cyclopropyl)benzoate (E90, 93%).

Using commercially available compounds and largely the procedures set forth in E2-E5 and substituting the appropriate starting materials, E90-E91 (Table 8) were made and E92-E94 (Table 9) are likewise synthesized.

TABLE 8

| Example | Structure |
| --- | --- |
| 90 | 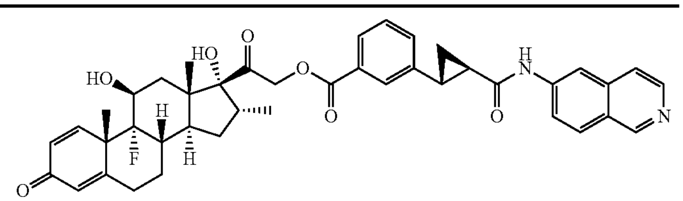 |
| 91 | 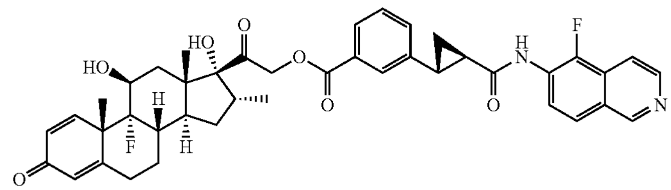 |

TABLE 9

| Example | Structure |
| --- | --- |
| 92 | 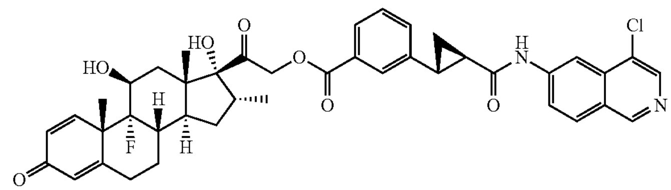 |
| 93 | 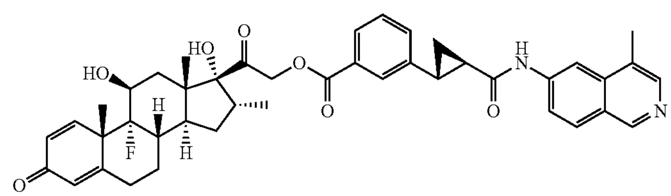 |
| 94 | 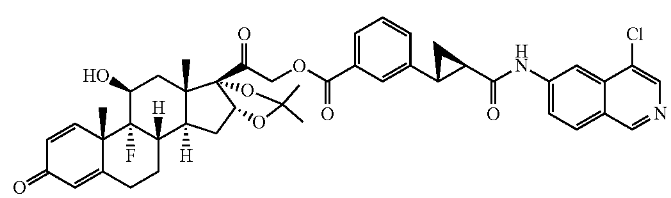 |

Example 5. In Vitro Comparison of the Effect of Corticosteroids, a ROCK Kinase and Compounds of the Invention on the Inhibition of ROCK-1 Kinase, ROCK-2 Kinase, and TNF-α

The TNFα assay quantifies secreted TNFα from RAW264.7 immortalized murine macrophages as an indicator of inflammation. The cells were concurrently treated with LPS (as an inducer of inflammation) and a titration of test molecules or control compounds for 4 hrs. After the incubation period, the media was harvested and assayed via an ELISA assay. ODs of experimental samples are fit to those of a standard curve to extrapolate the TNFα concentration. $IC_{50}$ values were calculated by fitting a curve to experimental values with the controls as the top and bottom limits of the curve. Selected compounds provided herein were subjected to this assay. Results are summarized in Table 10.

TABLE 10

TNFα secretion assay $IC_{50}$ results.

| Example | Structure: Steroid-linker-AR | MW | $IC_{50}$ |
|---|---|---|---|
| Example 4 | | 896.02 | 230 nM |
| Example 11 | | 910.05 | 429 nM |
| Example 12 | | 809.93 | 90.5 nM |
| Example 14 | | 864.01 | 620.5 nM |
| Example 91 | | 724.80 | 102.5 nM |
| Example 90 | | 706.81 | 300 nM |

TABLE 10-continued

TNFα secretion assay IC$_{50}$ results.

| Example | Structure: Steroid-linker-AR | MW | IC$_{50}$ |
|---|---|---|---|
| Example 20 | | 809.93 | 144 nM |
| Example 21 | | 777.92 | 1650 nM |
| Example 23 | | 869.96 | 4.5 nM |
| Example 26 | | 809.93 | 227 nM |
| Example 28 | | 851.97 | 15.5 nM |
| Example 29 | | 938.06 | 71 nM |

TABLE 10-continued

TNFα secretion assay IC$_{50}$ results.

| Example | Structure: Steroid-linker-AR | MW | IC$_{50}$ |
|---|---|---|---|
| Example 31 | 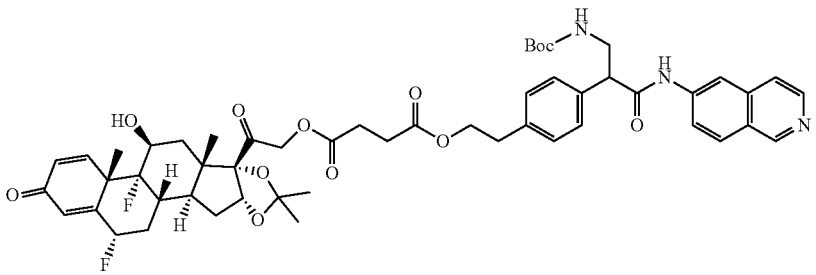 | 970.08 | 5465 nM |
| Example 37 | 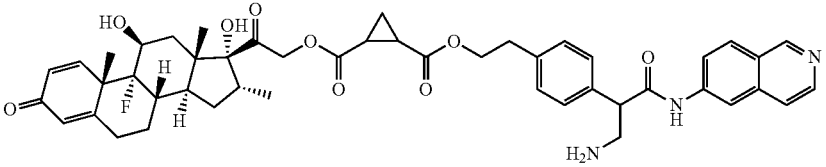 | 821.94 | 3100 nM |

Example 6. In Vitro Kinase Activity

Inhibition of various kinases was assayed. Results are summarized in Table 11.

TABLE 10

Kinase assay IC$_{50}$ (nM) results.

| Example | Salt | ROCK2 | ROCK1 | PKA | JAK1 | JAK2 | JAK3 | TYK2 | IKKb |
|---|---|---|---|---|---|---|---|---|---|
| Example 40 | HCl | 13 | 19 | 71 | 50000 | 38320 | 17730 | 50000 | 32886 |
| Example 25 | HCl | 17 | 25 | 138 | 50000 | 40871 | 21390 | 50000 | 38496 |
| Example 83 | HCl | 9 | 11 | 29 | 34675 | 22021 | 7729 | 50000 | 19151 |
| Example 66 | HCl | 26 | 36 | 117 | 50000 | 36241 | 43246 | 50000 | 50000 |
| Example 33 | HCl | 14 | 21 | 81 | 50000 | 42354 | 30082 | 50000 | 40091 |
| Example 27 | HCl | 13 | 29 | 317 | 50000 | 41673 | 11632 | 50000 | 46807 |
| Example 19 | HCl | 27 | 58 | 332 | 9574 | 13799 | 2573 | 50000 | 50000 |

| Example | Salt | PKCh | PKCd | PKCe | AKT1 | PTM | HTM | TOX | NFkB |
|---|---|---|---|---|---|---|---|---|---|
| Example 40 | HCl | 190 | 152 | 244 | 523 | 217 | 11 | 100000 | 28 |
| Example 25 | HCl | 173 | 225 | 1578 | 955 | 295 | 4.5 | 100000 | 39 |
| Example 83 | HCl | 51 | 56 | 154 | 95 | 43 | 25 | 100000 | 55 |
| Example 66 | HCl | 282 | 357 | 3614 | 1358 | 358 | 15 | 100000 | 55 |
| Example 33 | HCl | 145 | 142 | 1575 | 1243 | 75 | 4.0 | 55246 | 103 |
| Example 27 | HCl | 331 | 509 | 3455 | 2641 | 145 | 6 | 100000 | 1788 |
| Example 19 | HCl | 436 | 589 | 4163 | 2540 | 706 | — | — | 10000 |

Example 7. Myeloperoxidase (MPO) Activity

Figure 5:
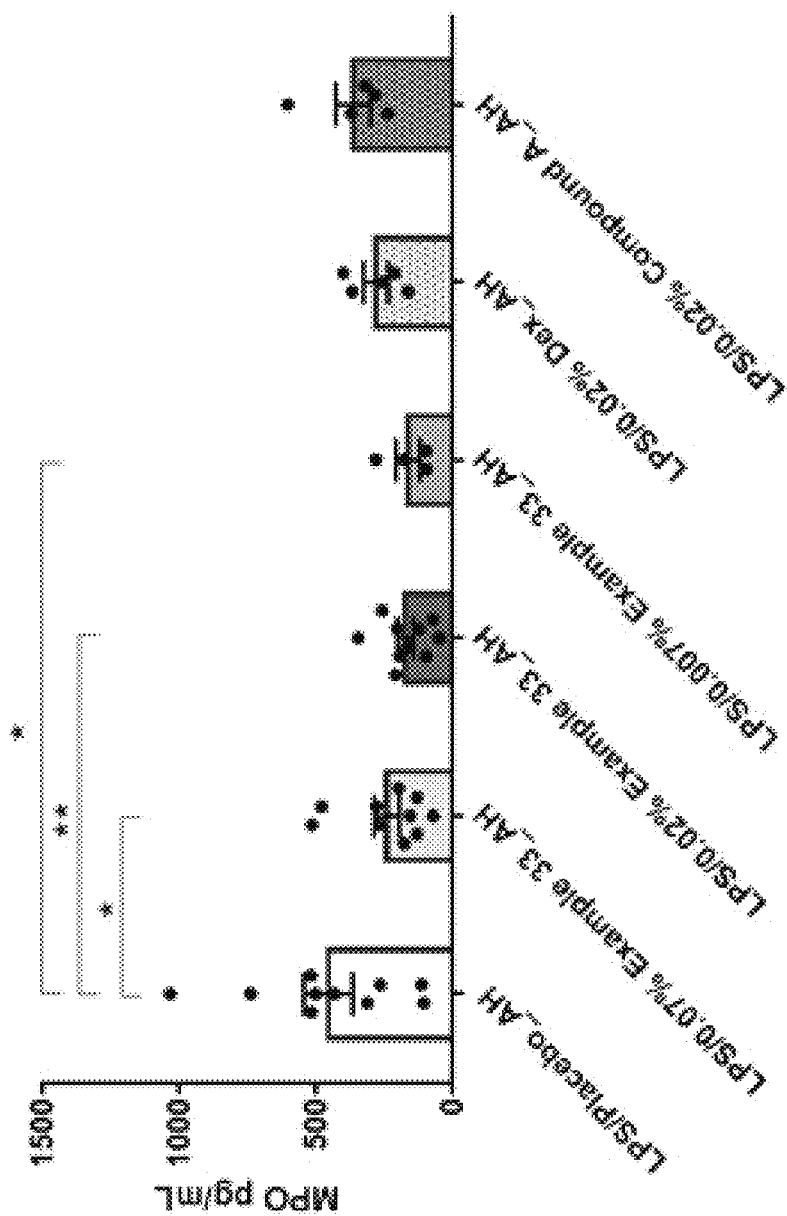
FIG. 5 shows the inhibiting effect of an isoquinoline-steroid conjugate described herein (Example 33) on myeloperoxidase activity in aqueous humor as compared to dexamethasone alone and (S)-3-amino-2-(4-(hydroxymethyl)phenyl)-N-(isoquinolin-6-yl)propanamide alone (Compound A).
Figure 6:
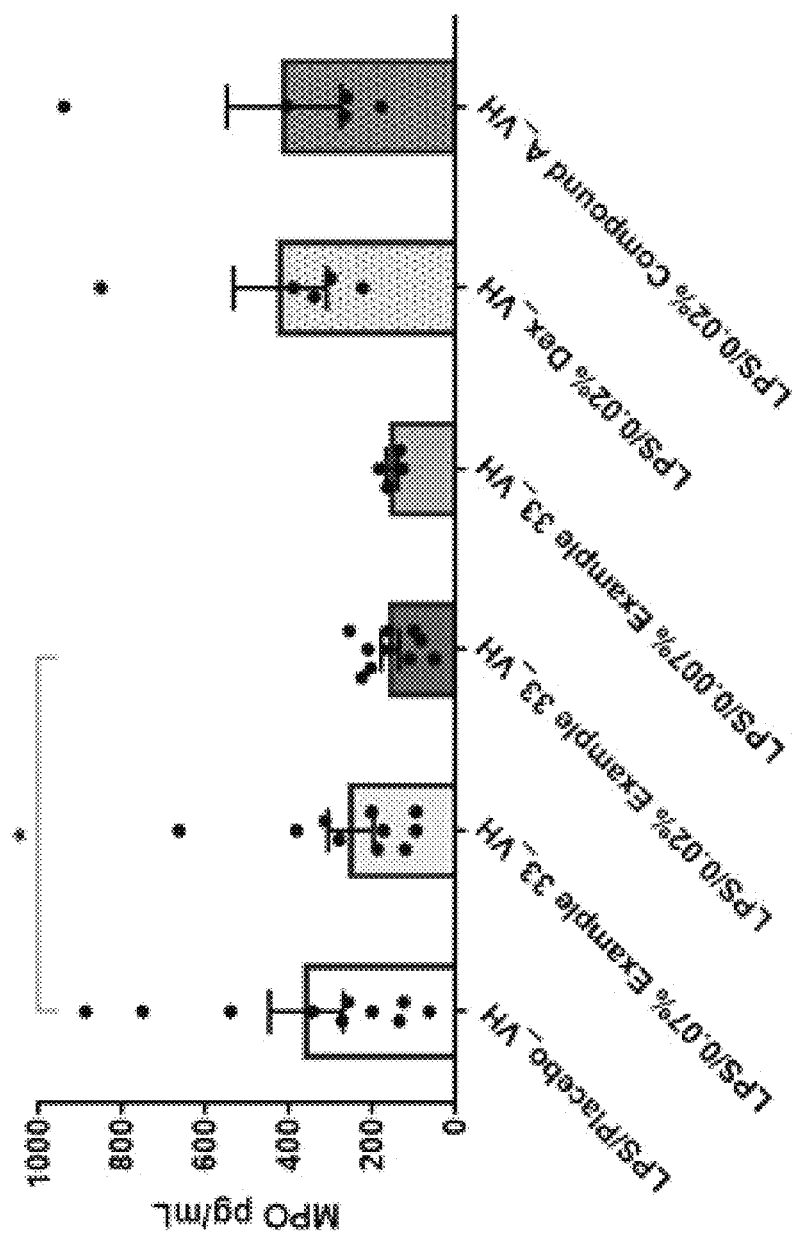
FIG. 6 shows the inhibiting effect of an isoquinoline-steroid conjugate described herein (Example 33) on myeloperoxidase activity in vitreous humor as compared to dexamethasone alone and (S)-3-amino-2-(4-(hydroxymethyl)phenyl)-N-(isoquinolin-6-yl)propanamide alone (Compound A).

Adult C57Bl6 male mice were injected with 2 ng of lipopolysaccharide (LPS) intravitreally. The mice were then dosed with vehicle, compounds or control treatments (0.07% w/w, 0.02% w/w or 0.007% w/w) at times 0 and 6 hours post-injection. Aqueous humor (AH) and vitreous humor (VH) was collected 24 hours after injection of LPS and assayed for MPO activity by ELISA. Data is a compilation of two separate experiments. Statistical analysis was carried out on GraphPad prism using a multiple comparisons 1-way ANOVA with uncorrected Dunn's test. Results are shown in FIG. 5 (aqueous humor) and FIG. 6 (vitreous humor). In FIG. 5 and FIG. 6, Dex refers to dexamethasone, Compound A refers to (S)-3-amino-2-(4-(hydroxymethyl)phenyl)-N-(isoquinolin-6-yl)propanamide, * refers to $p<0.05$, and ** refers to $p<0.005$. MPO levels correspond to levels of neutrophil infiltration. In the context of non-infectious inflammatory events, neutrophils cause robust levels of damage to tissues. Lower levels of observed MPO in response to treatment suggests the therapy has an anti-inflammatory effect.

Where publications and patents are referred to throughout this disclosure, all U.S. patents cited herein are hereby incorporated by reference. All percentages, ratios, and proportions used herein are percent by weight unless otherwise specified.

Unless defined otherwise, all technical and scientific terms used herein generally have the same meaning as commonly understood by one of ordinary skill in the art to which this disclosure relates. Generally, the nomenclature and laboratory procedures used herein are those commonly employed by one of ordinary skill in the art.

What is claimed is:
1. A compound selected from:

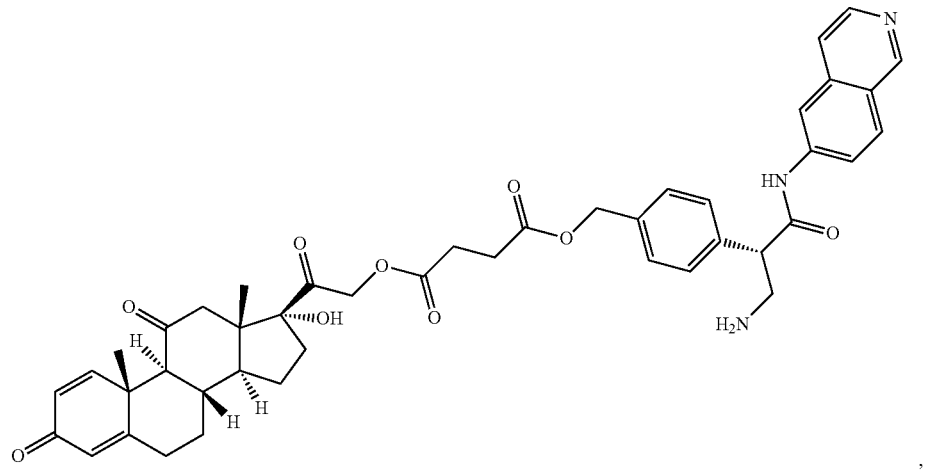

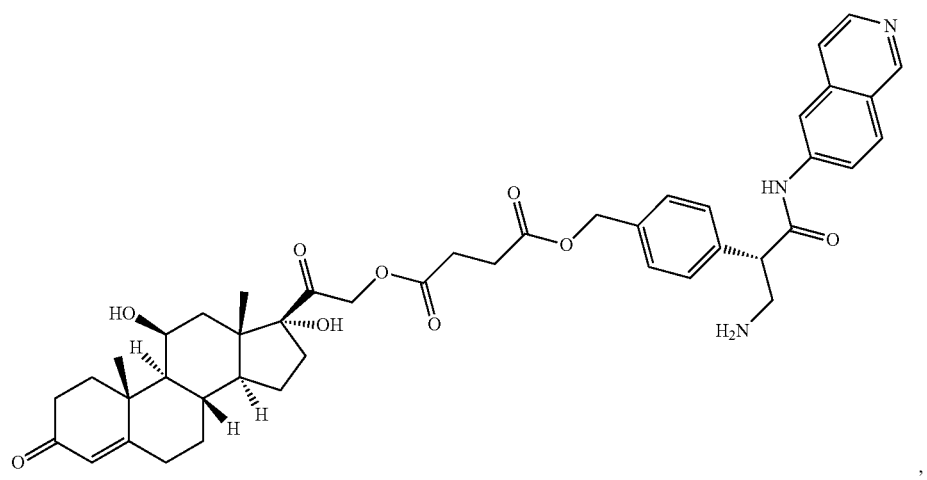

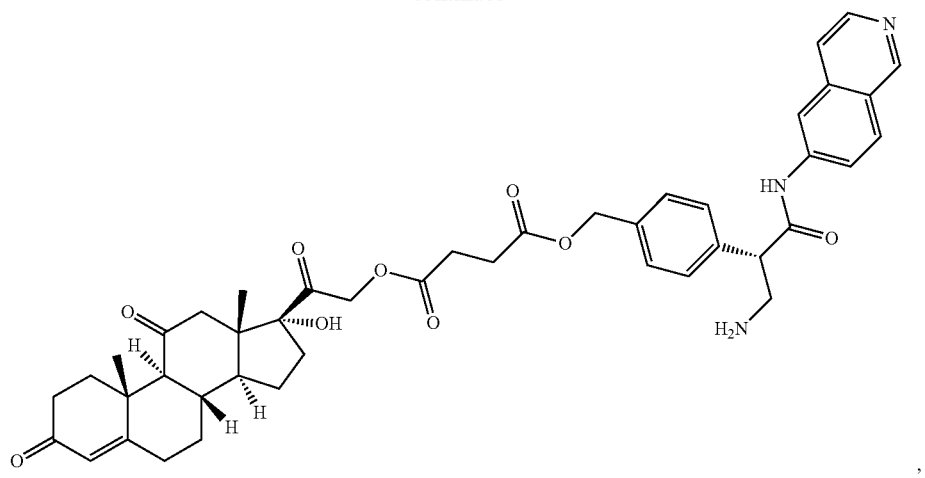
,
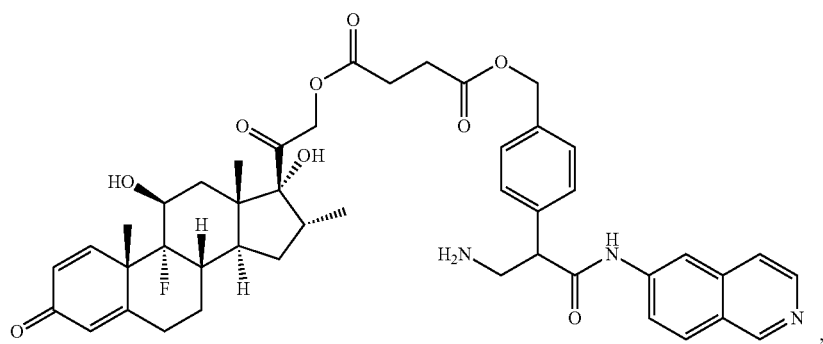
,
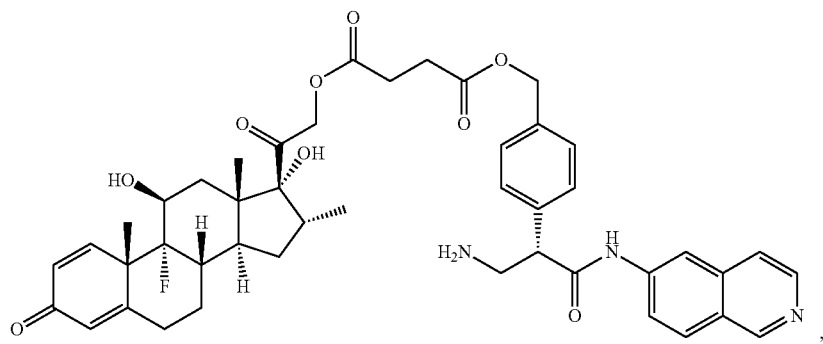
,
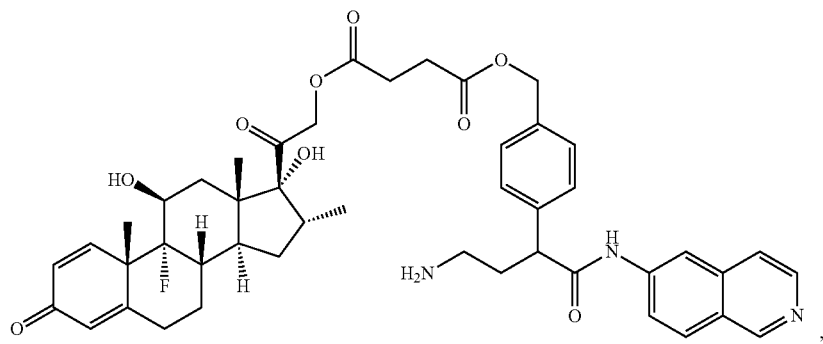
,

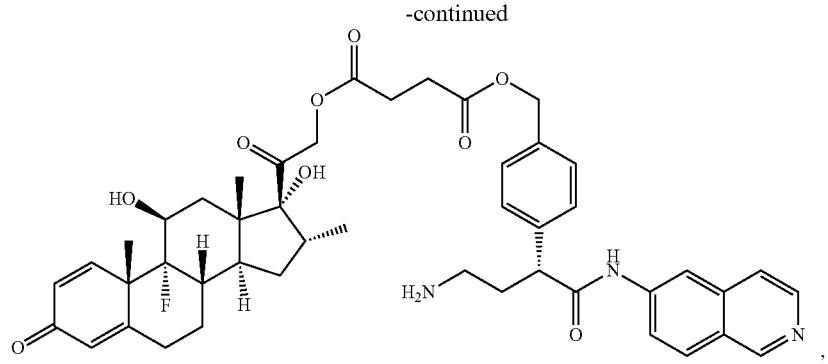
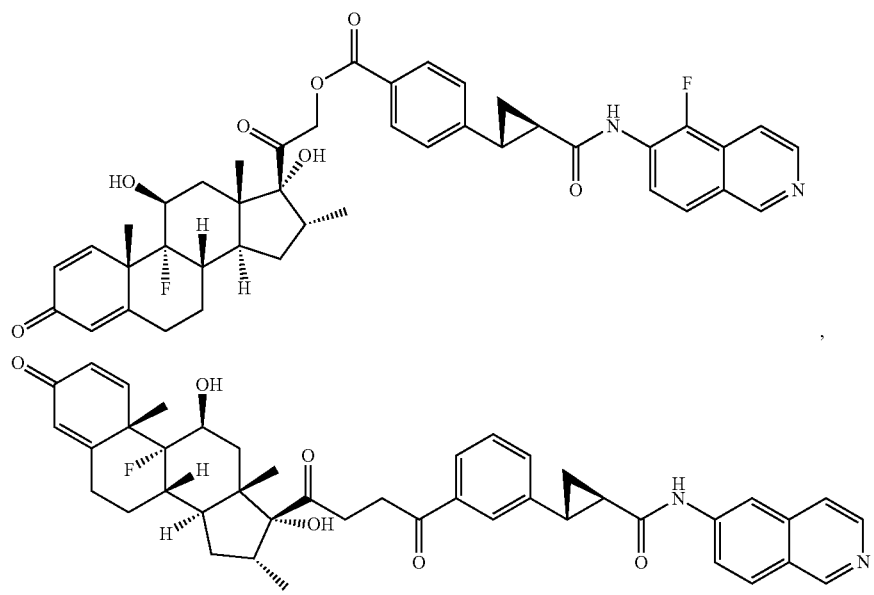
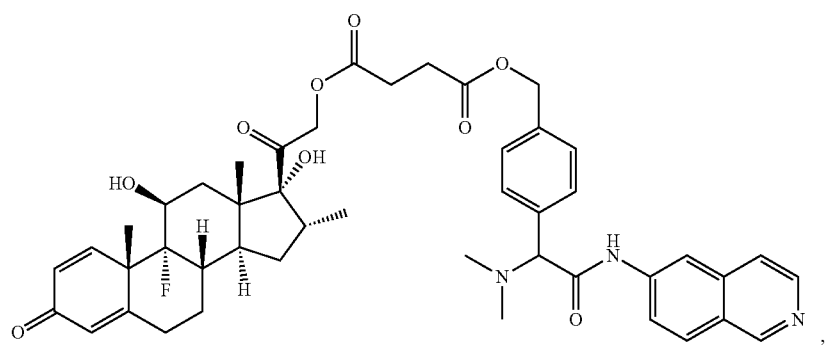
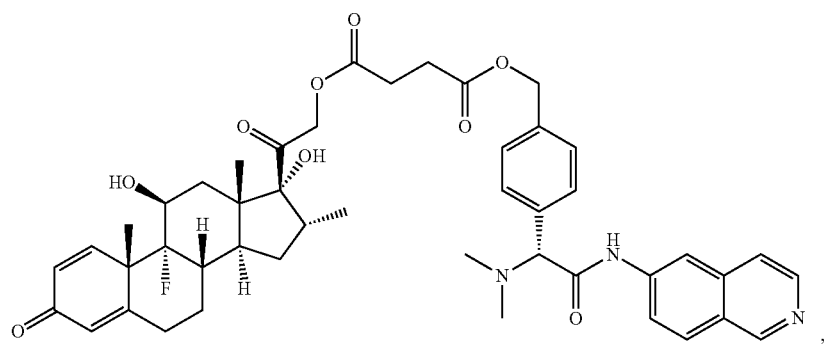

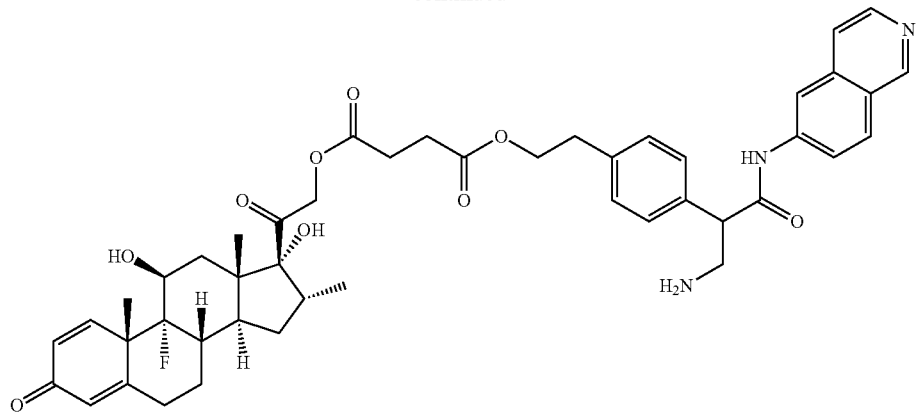
,
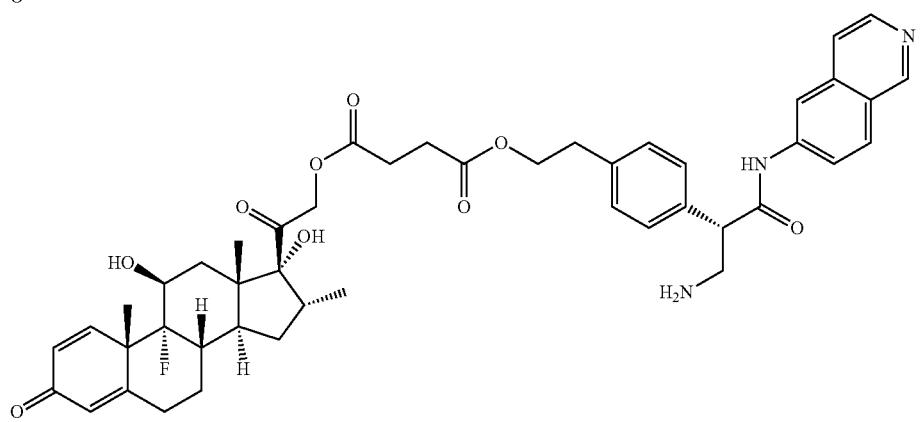
,
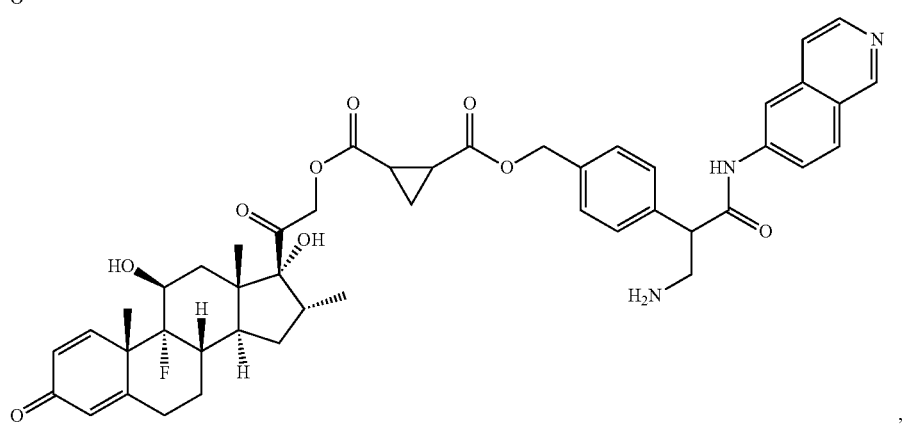
,
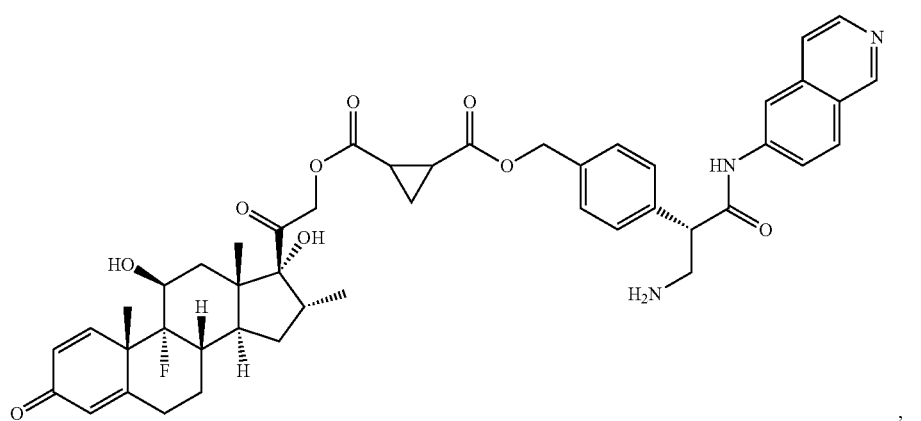
,

-continued
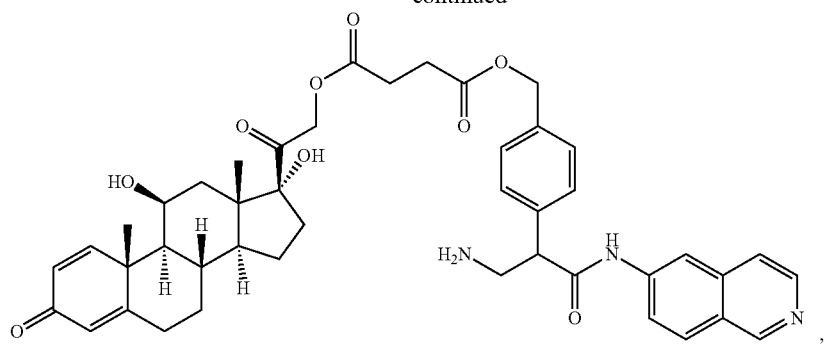
,
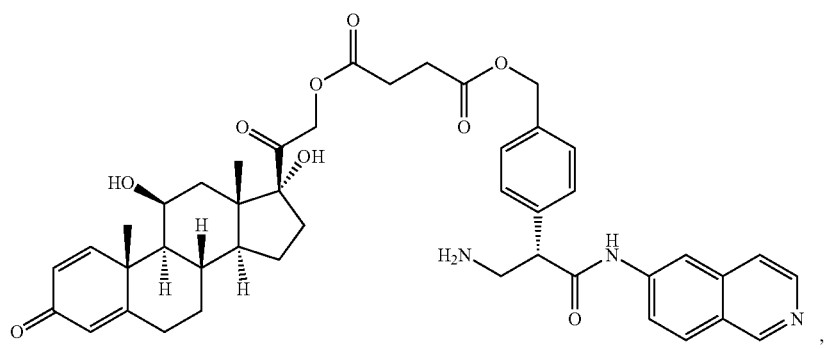
,
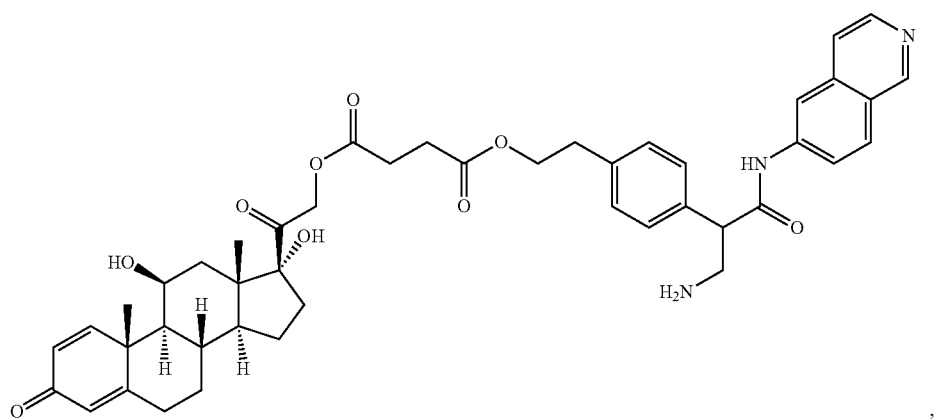
,
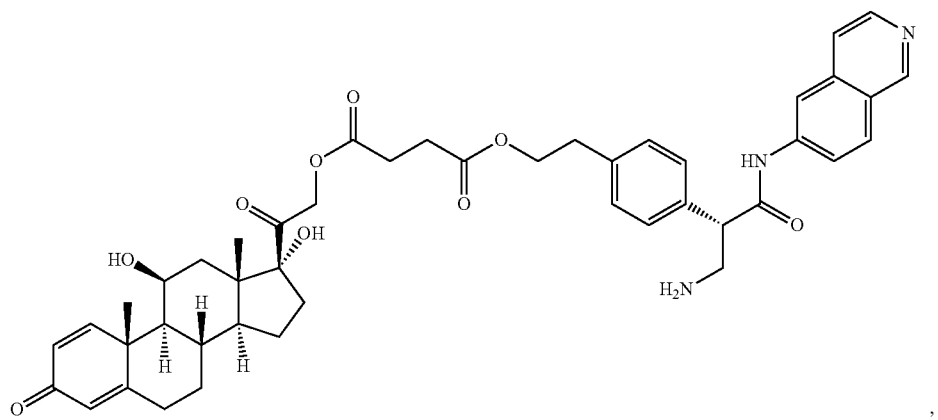
,

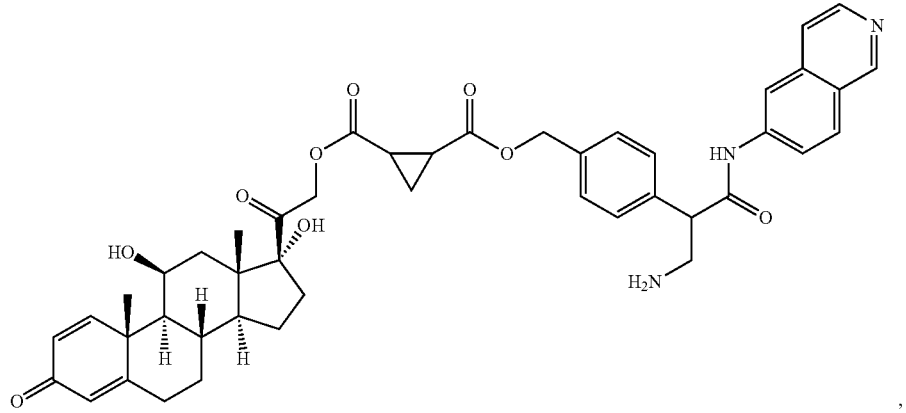
,
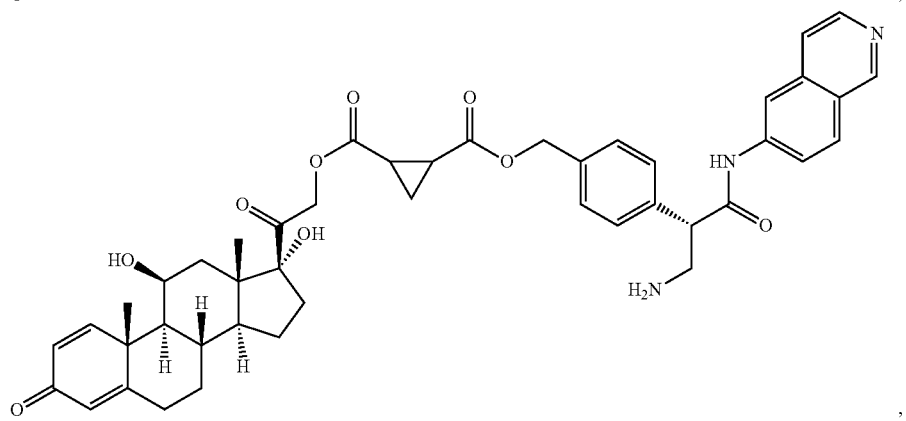
,
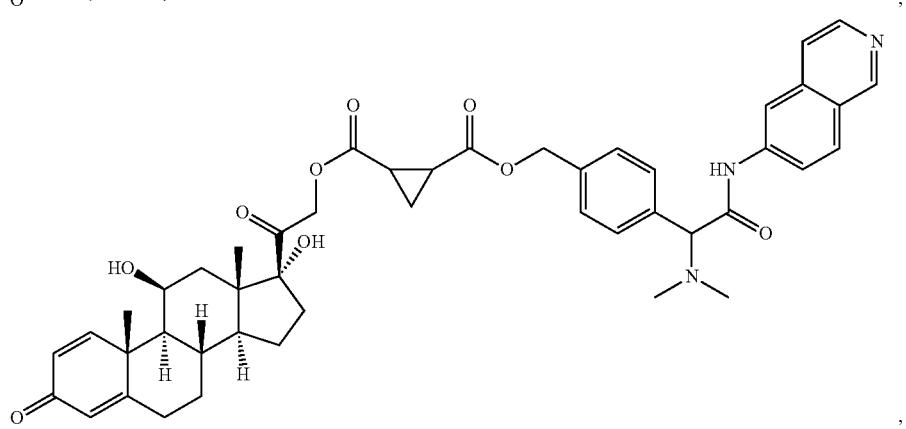
,
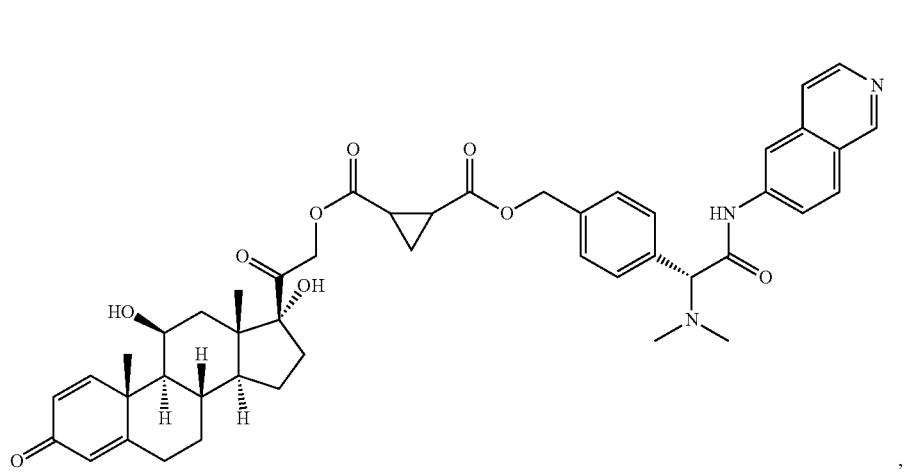
,

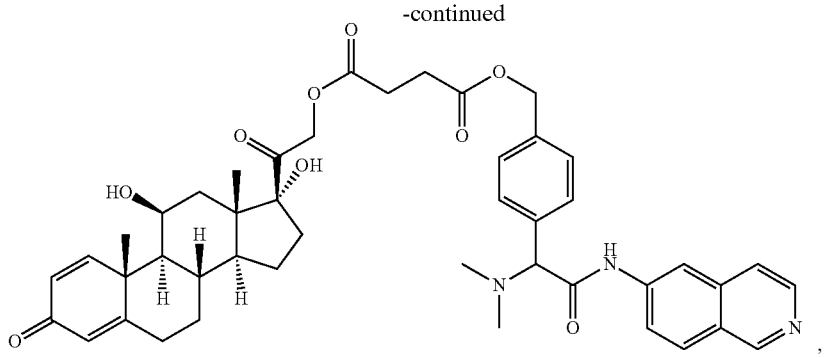
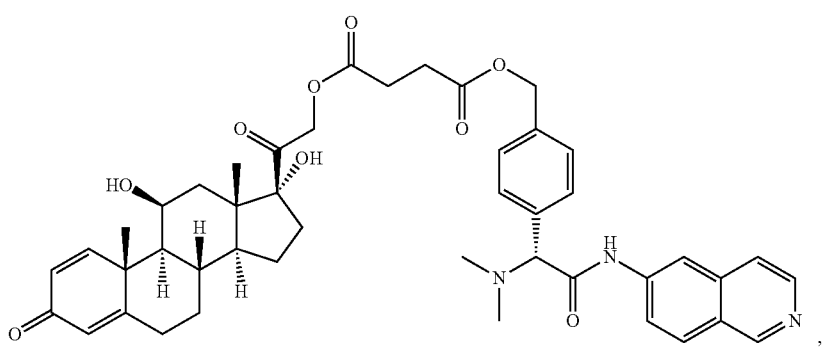
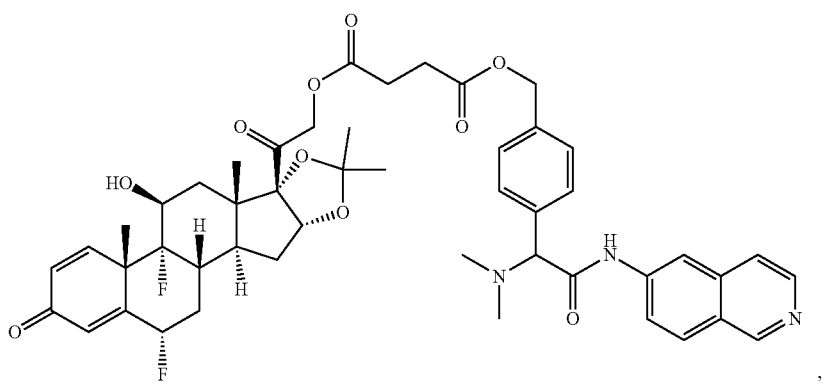
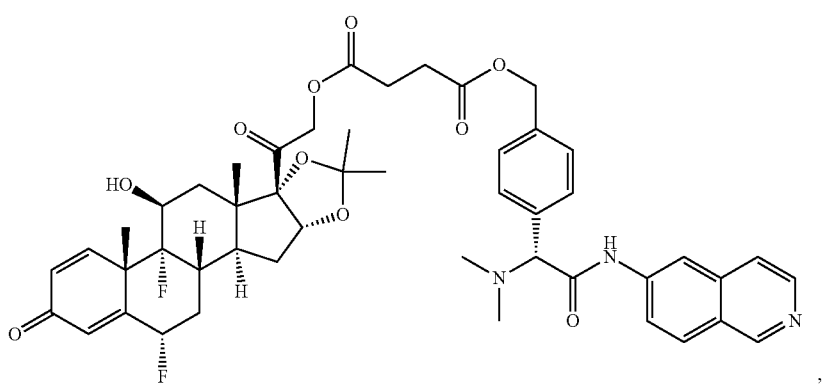

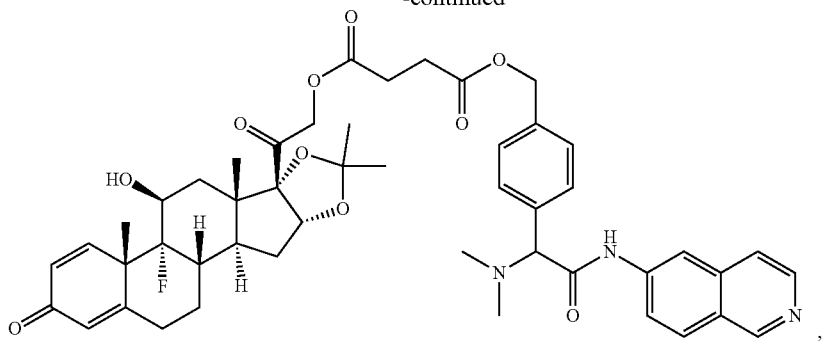
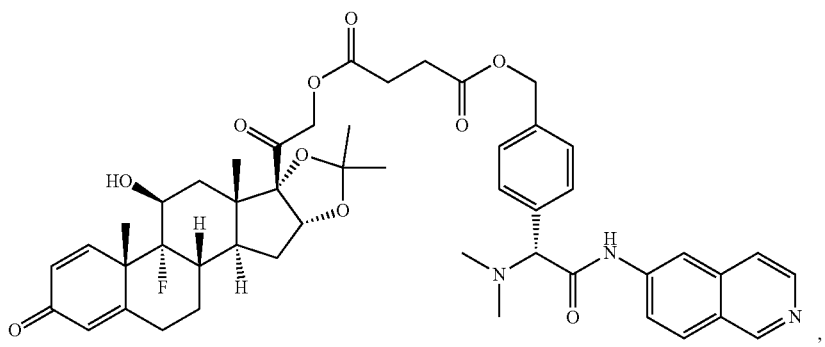
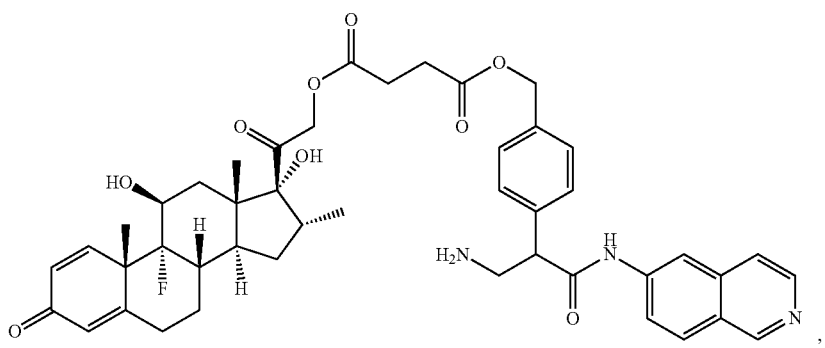
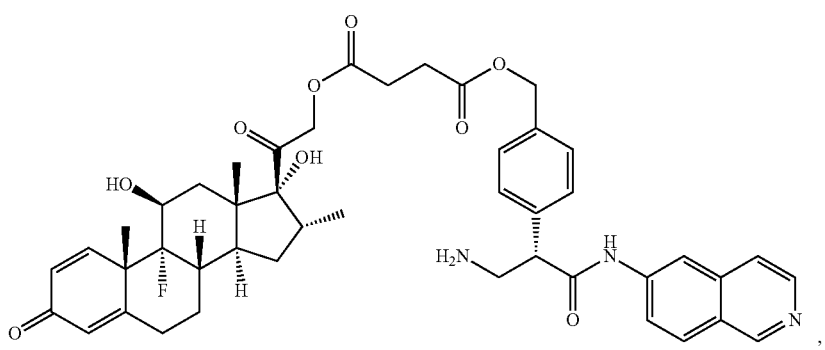
or a pharmaceutically acceptable salt thereof.

2. A compound having the formula:
$R^8-R^{10}-R^{11}$
or a pharmaceutically acceptable salt thereof, wherein $R^8$ is
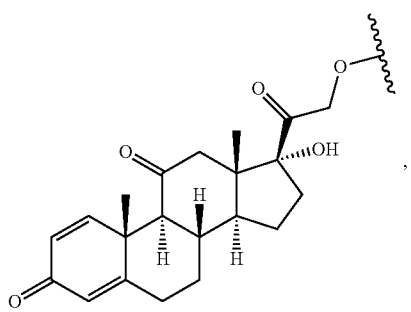,
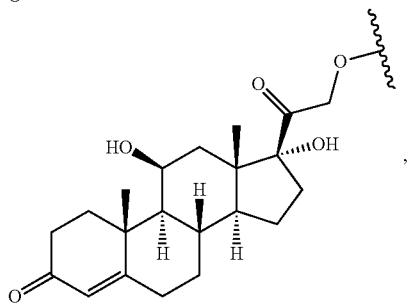,
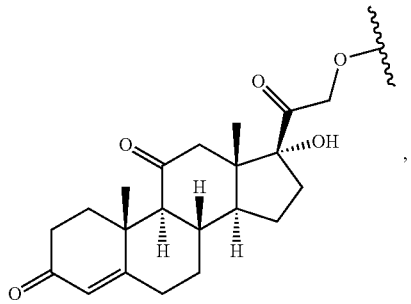,
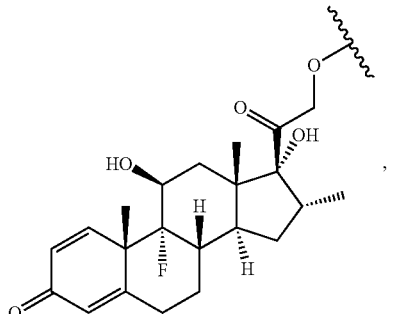,
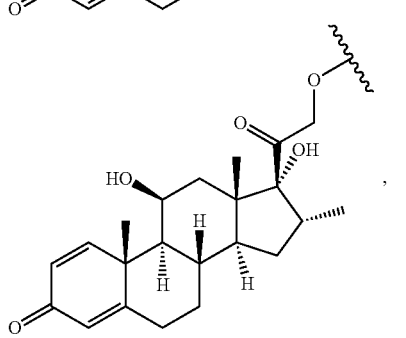,
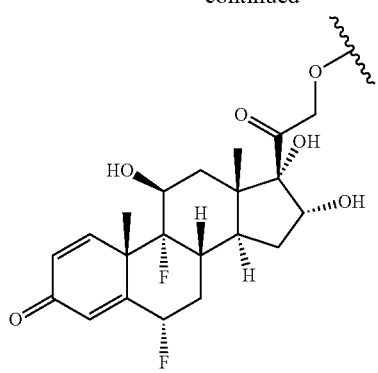,
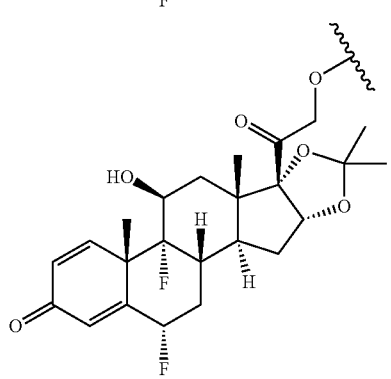,
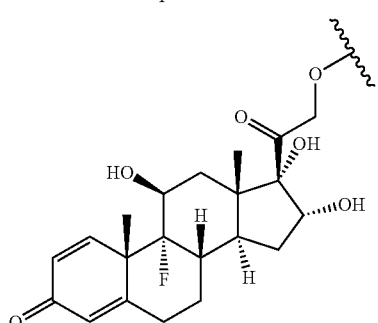, or
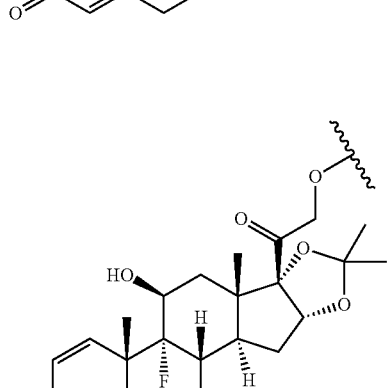;
$R^{10}$ is
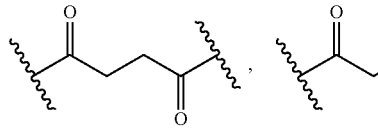, ,

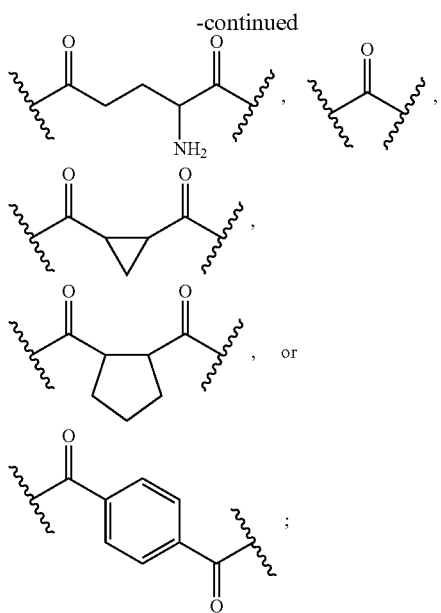
and R[11] is
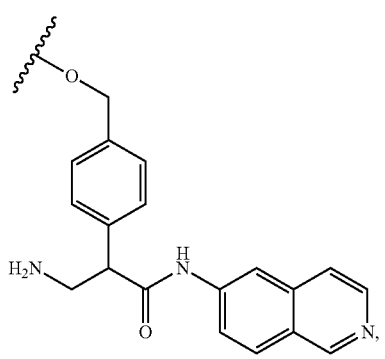
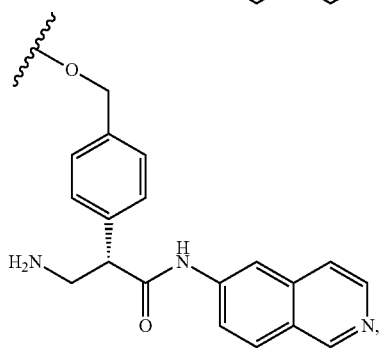
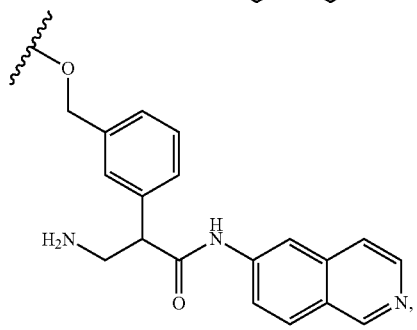
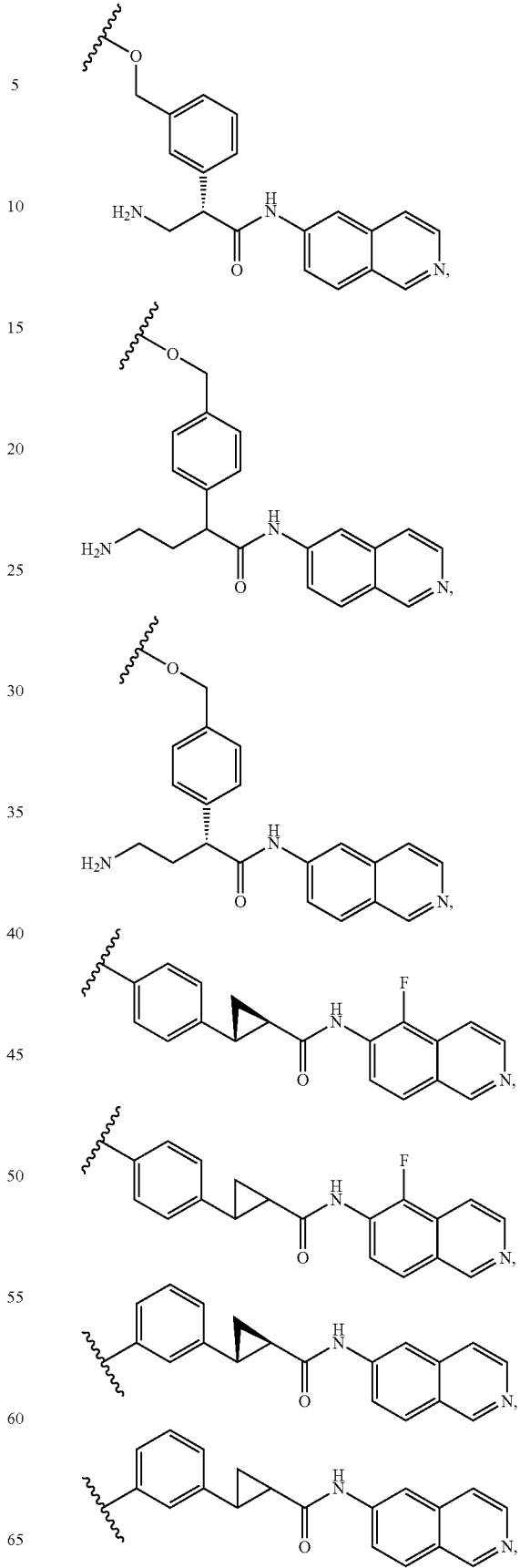

-continued
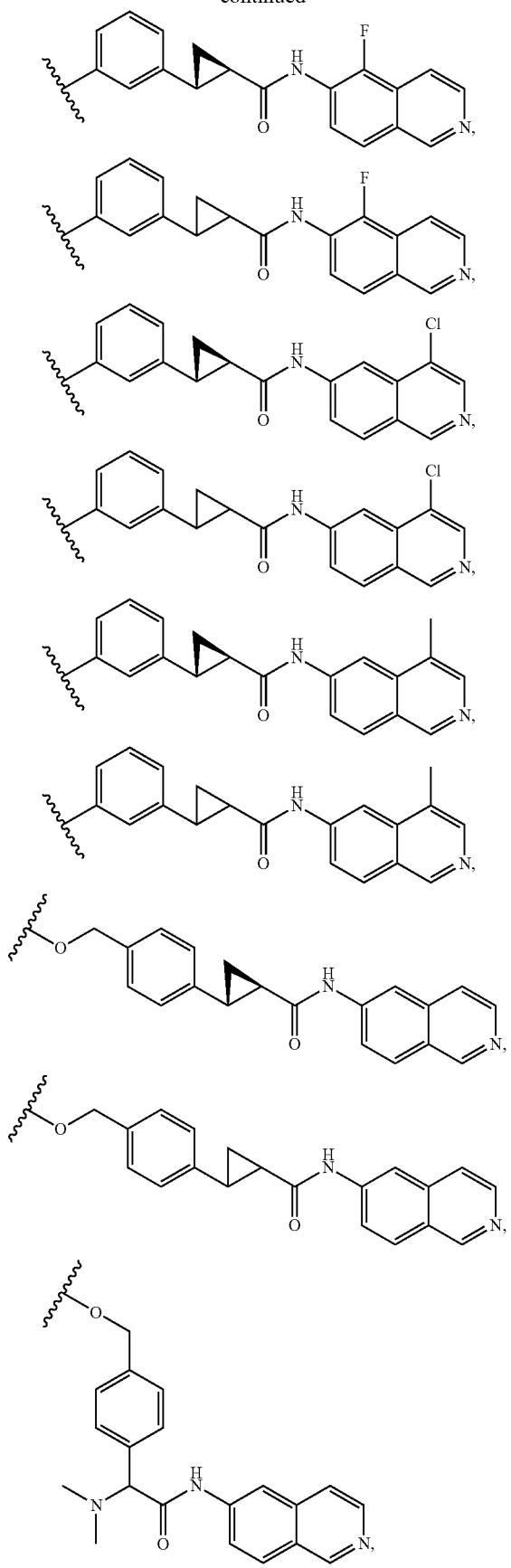
-continued
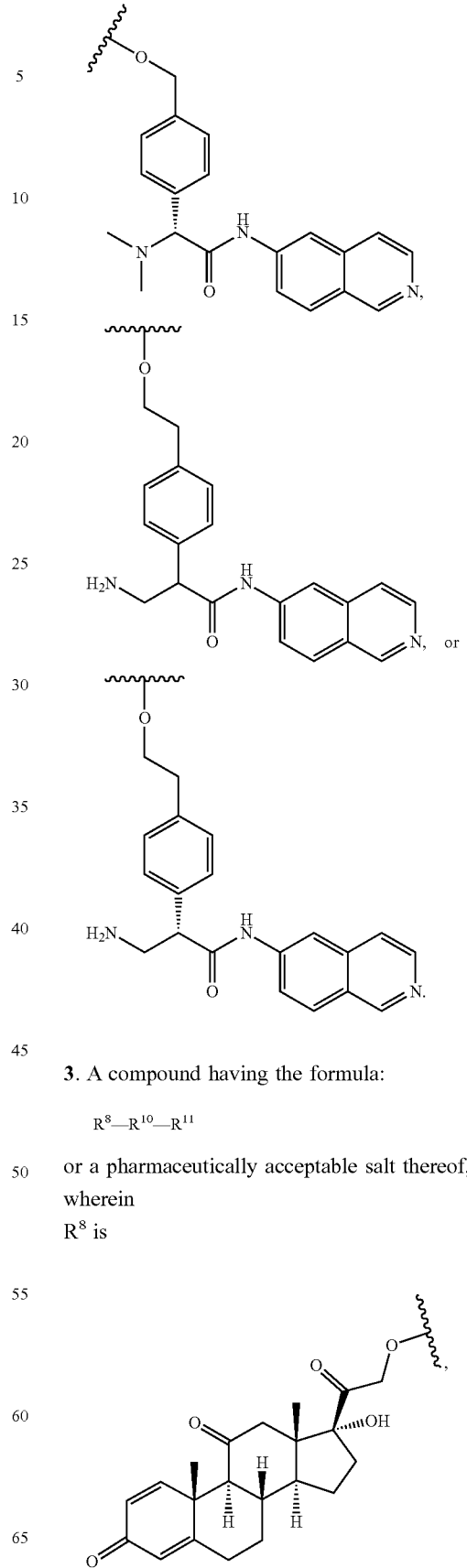
3. A compound having the formula:
$R^8-R^{10}-R^{11}$
or a pharmaceutically acceptable salt thereof, wherein
$R^8$ is
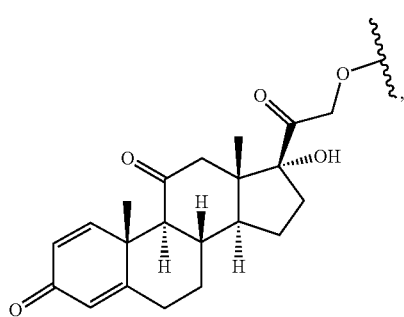

133
-continued
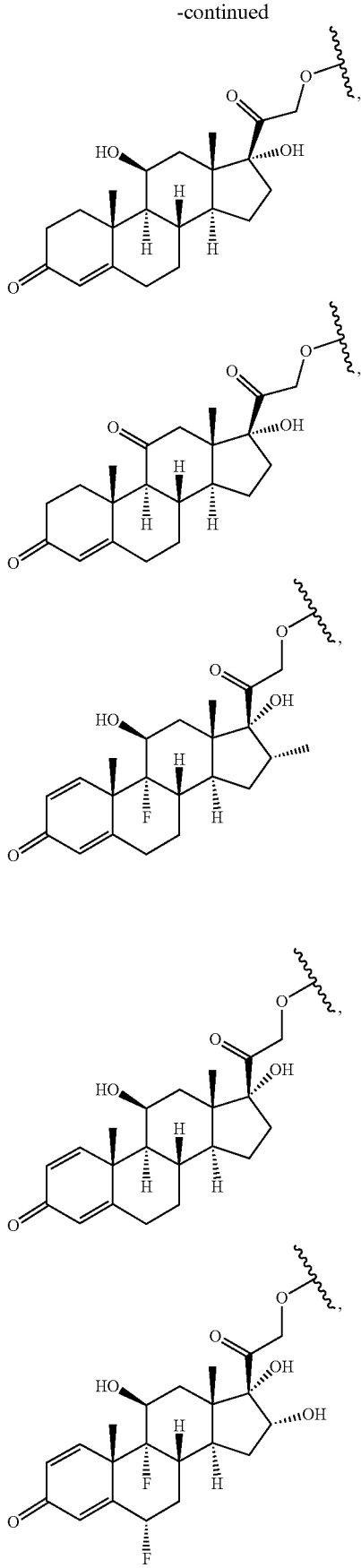
134
-continued
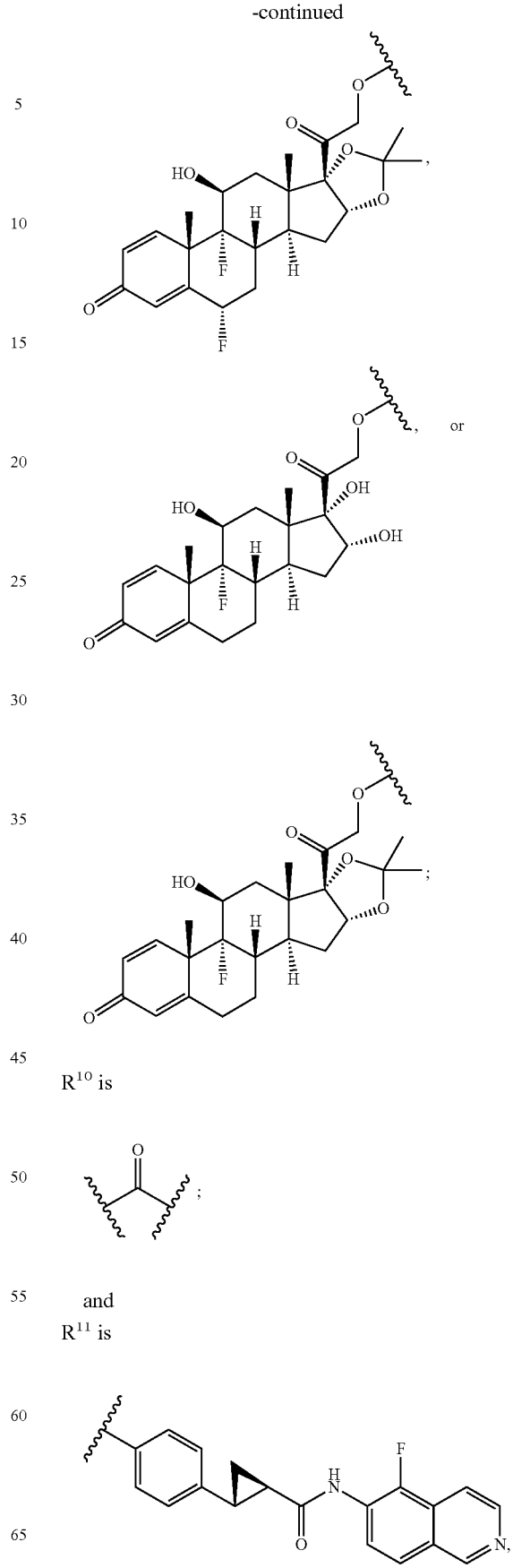
R[10] is
and
R[11] is

-continued
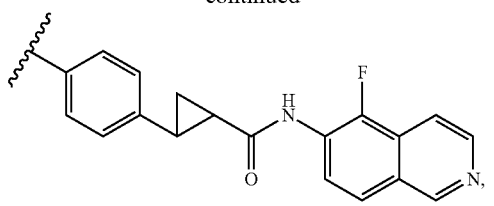
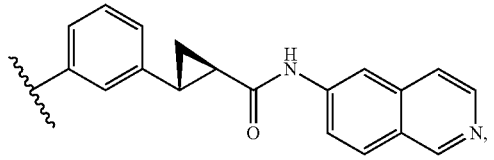
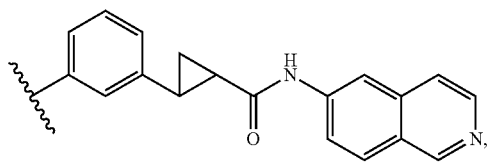
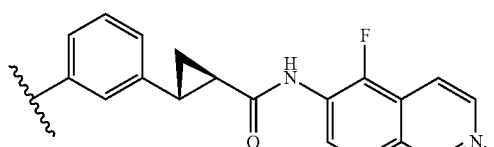
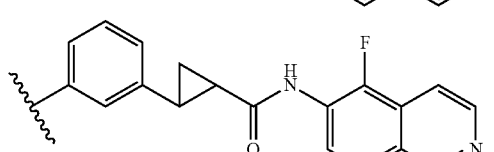
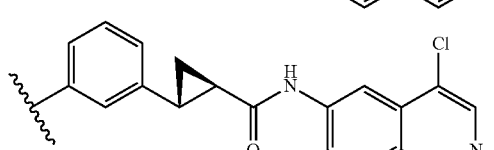
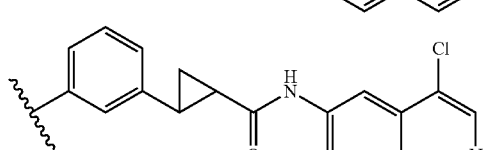
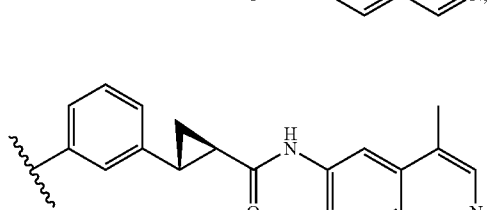
or
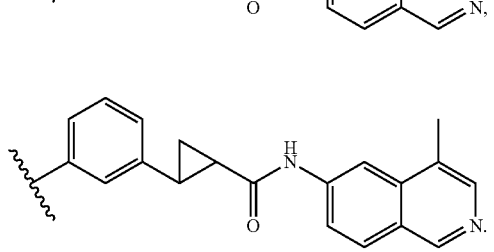
4. A compound having the formula:
$$R^8-R^{10}-R^{11}$$
or a pharmaceutically acceptable salt thereof, wherein
$R^8$ is
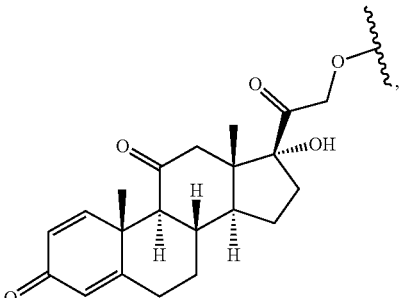
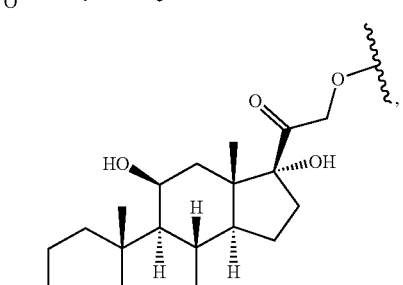
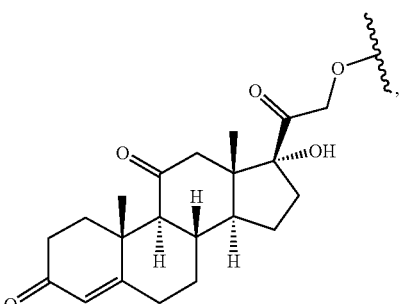
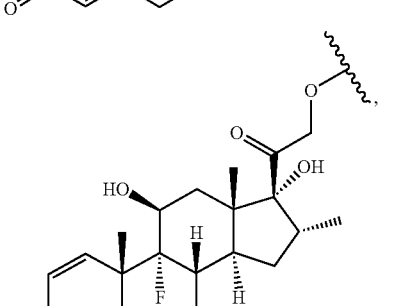
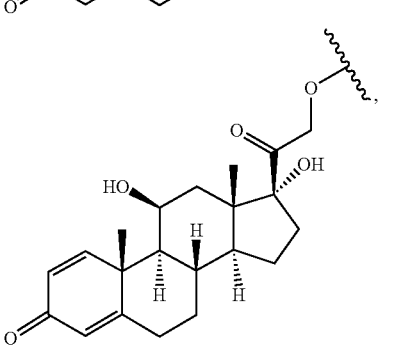

-continued
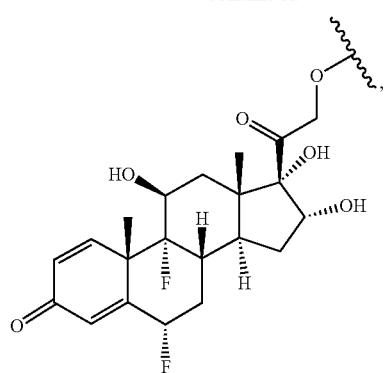
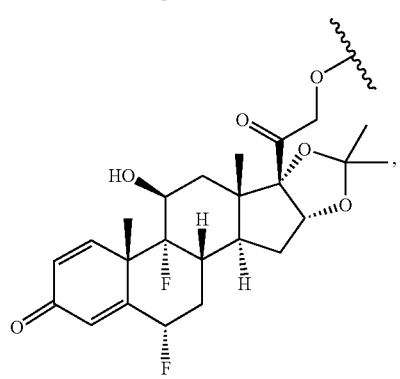
or
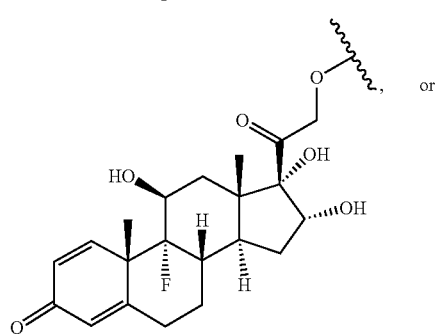
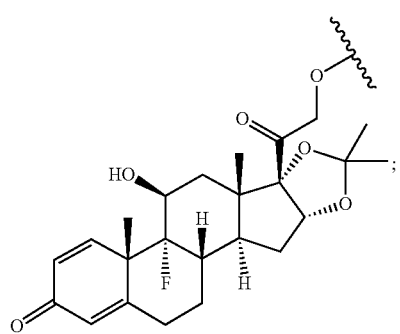
$R^{10}$ is
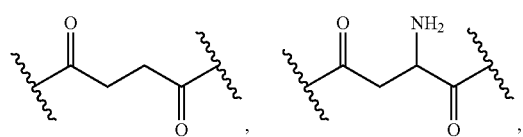
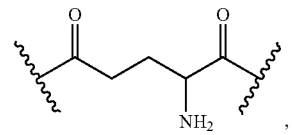
,
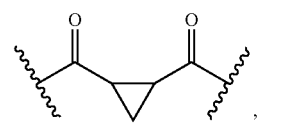
,
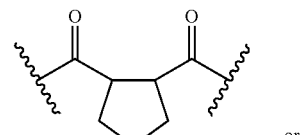
, or
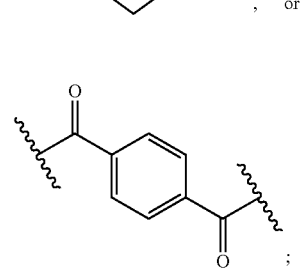
;
and
$R^{11}$ is
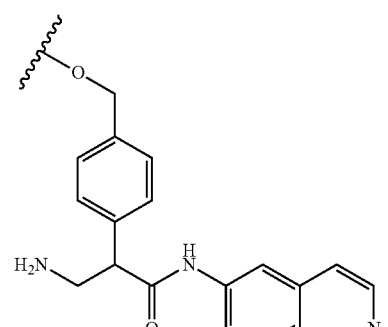
,
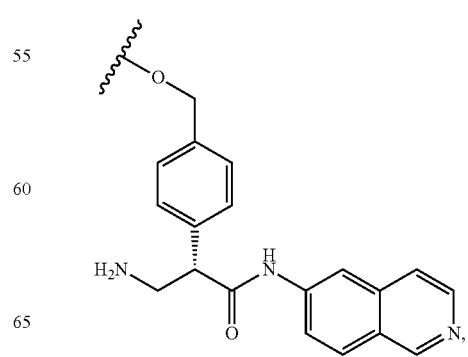
,

139 -continued
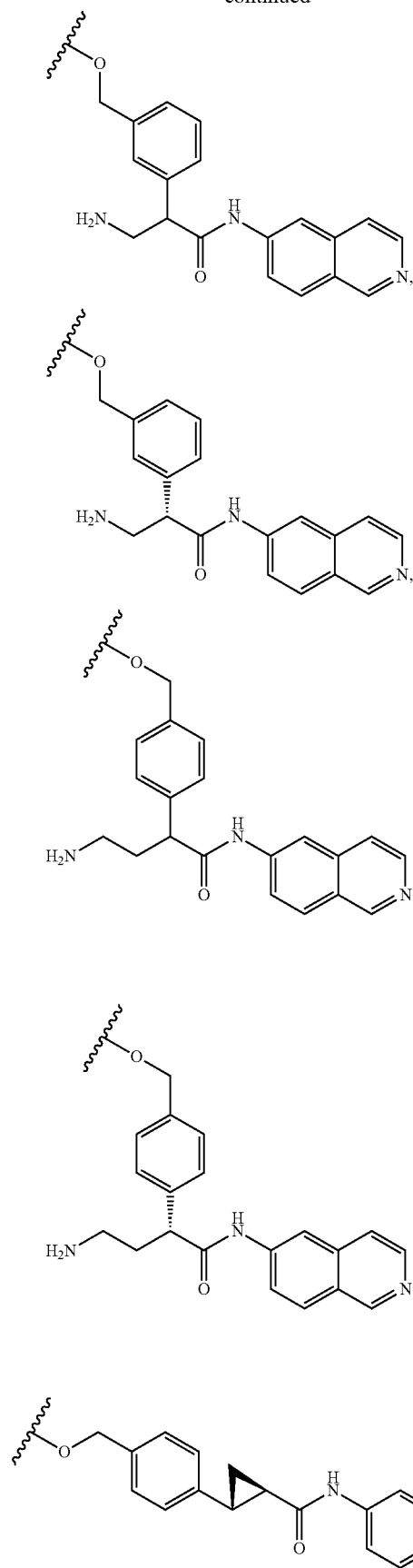
140 -continued
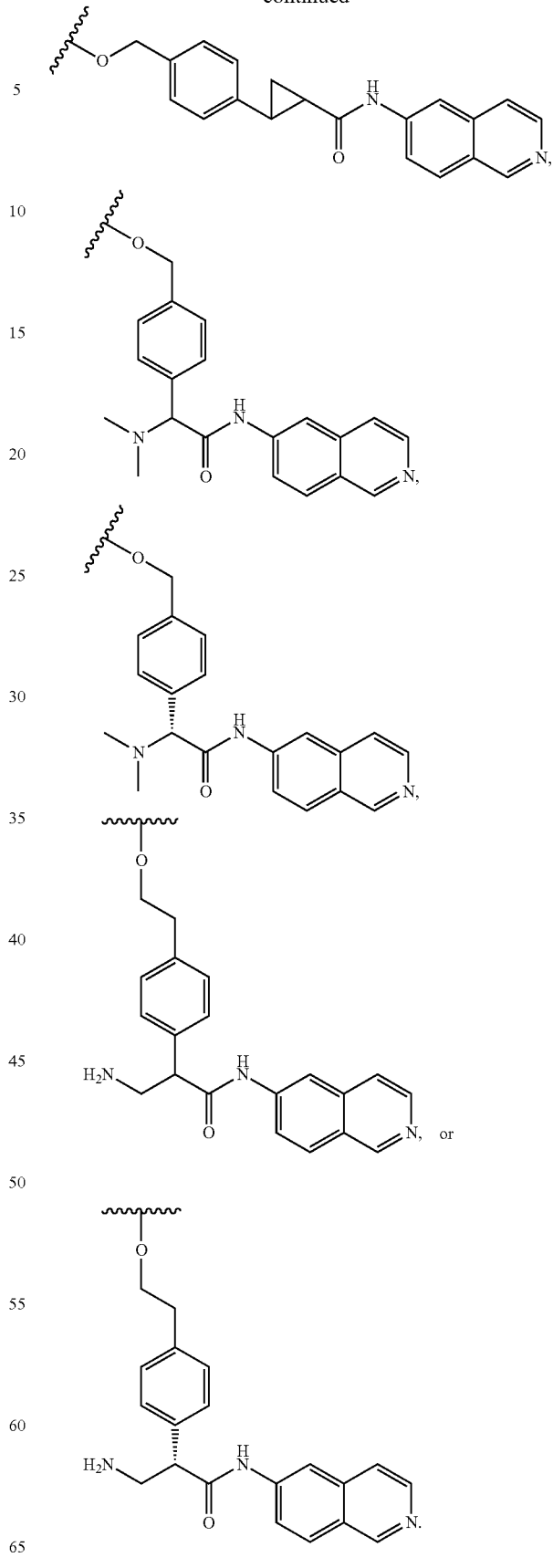

5. A compound having the formula:
$R^8$—$R^{10}$—$R^{11}$
or a pharmaceutically acceptable salt thereof, wherein
$R^8$ is
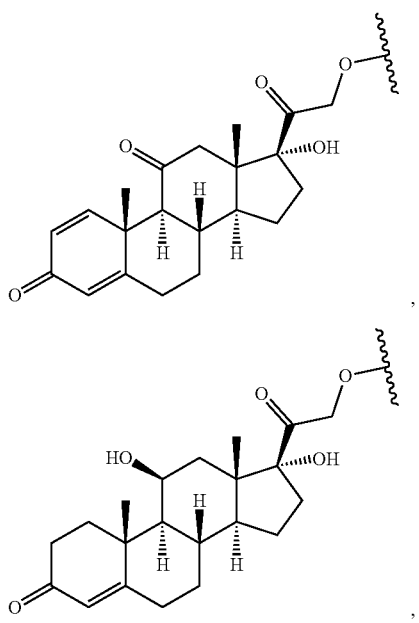
,
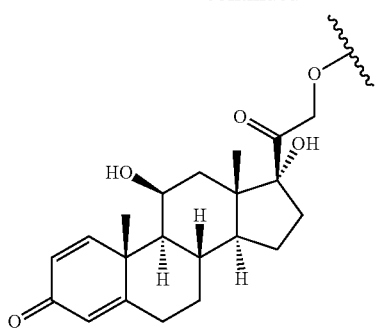
,
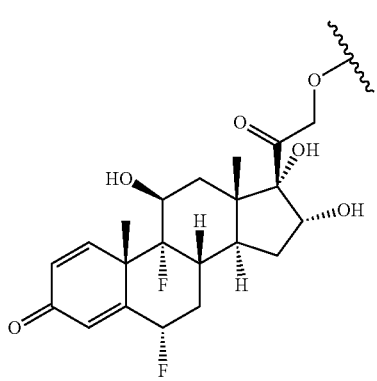
,
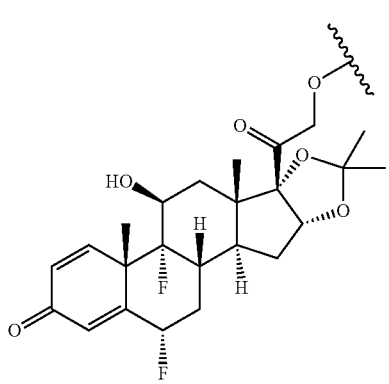
,
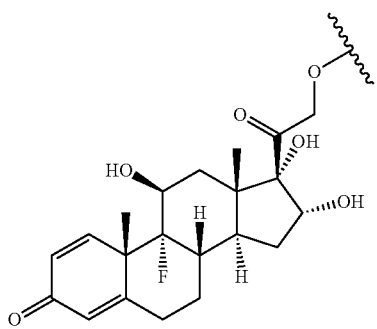
, or

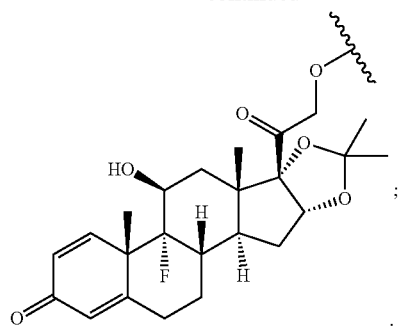
R[10] is
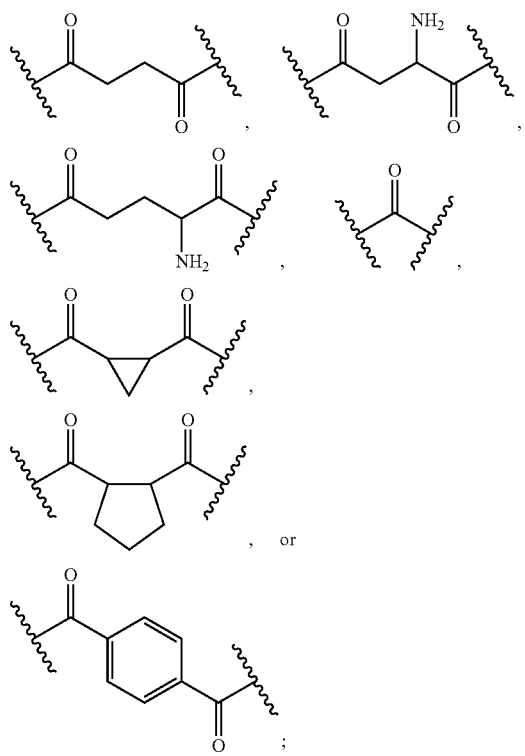
and
R[11] is
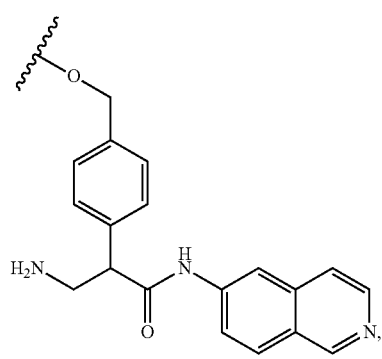
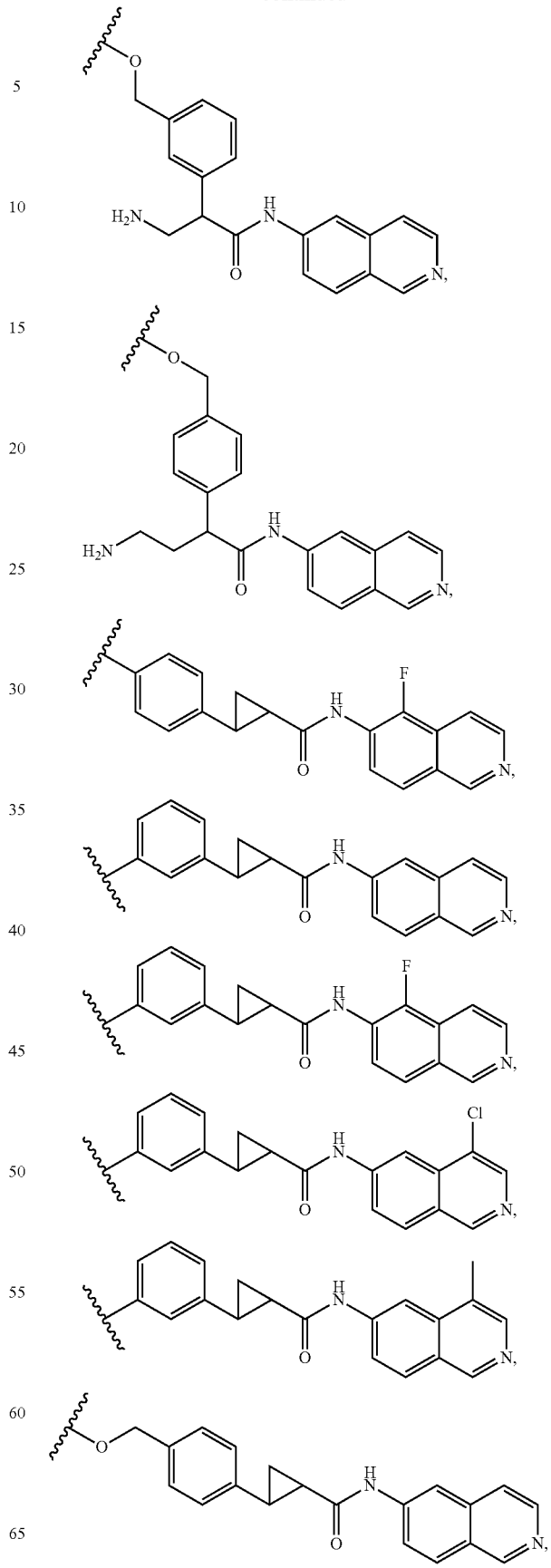

145
-continued
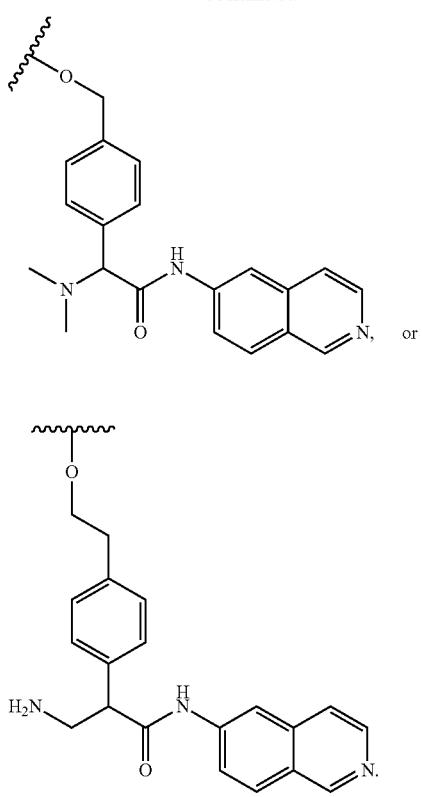
or
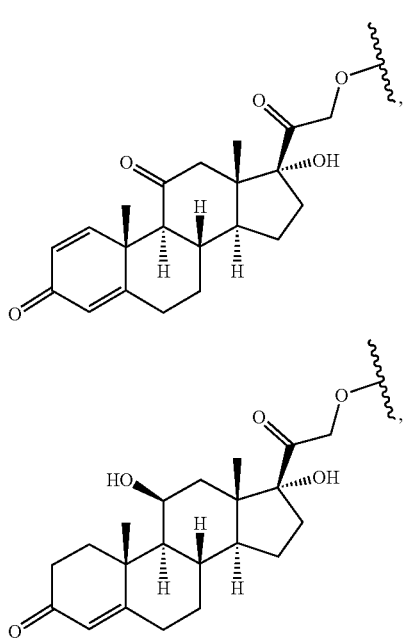
6. A compound having the formula:
$R^8$—$R^{10}$—$R^{11}$
or a pharmaceutically acceptable salt thereof, wherein
$R^8$ is
146
-continued
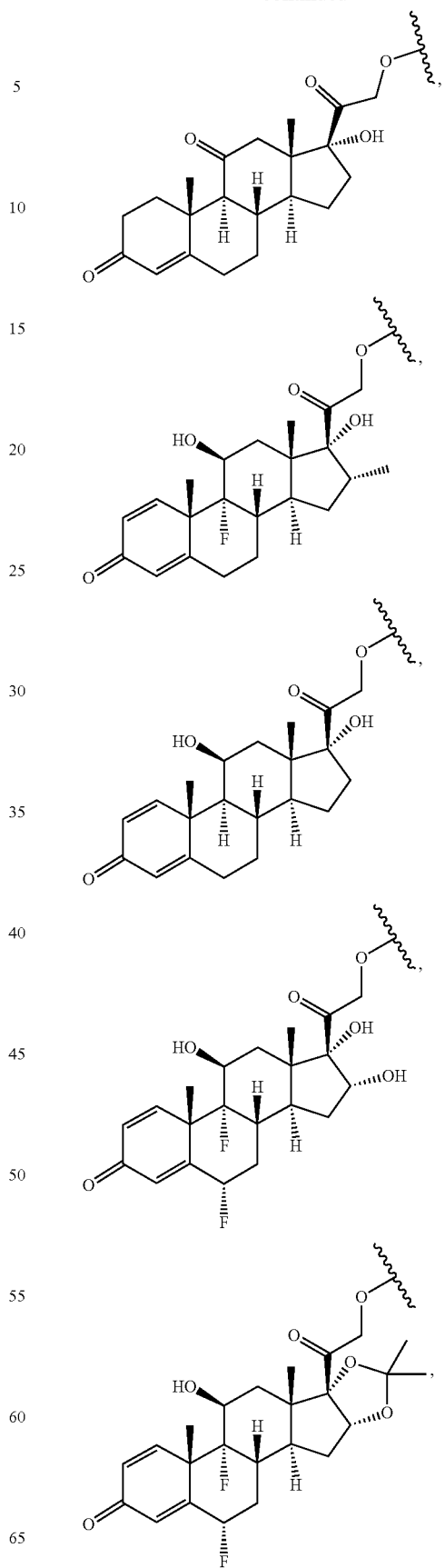

-continued
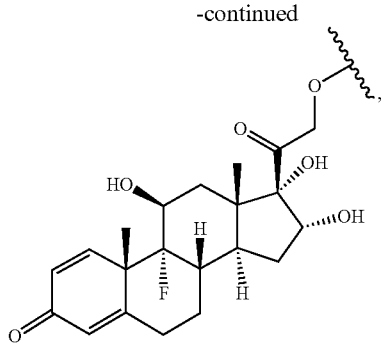
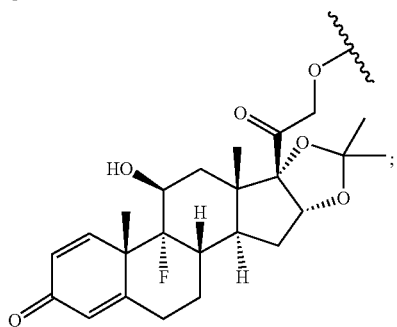
$R^{10}$ is
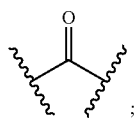 [SMILES: *C(*)=O]
and
$R^{11}$ is
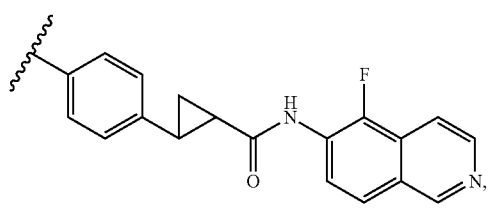
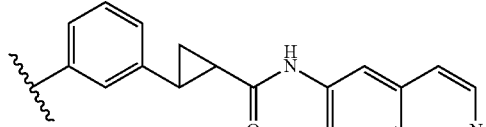
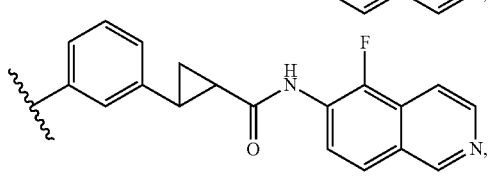
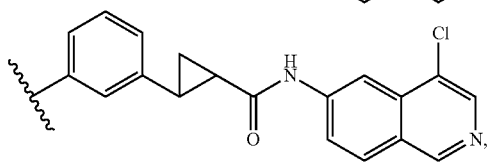 or
-continued
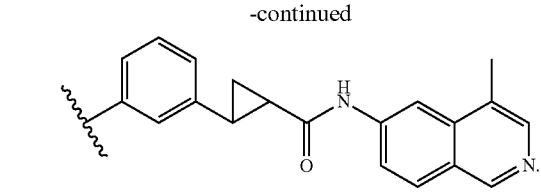
7. A compound having the formula:
$$R^8-R^{10}-R^{11}$$
or a pharmaceutically acceptable salt thereof, wherein
$R^8$ is
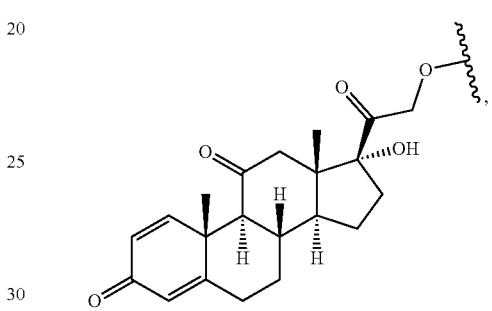
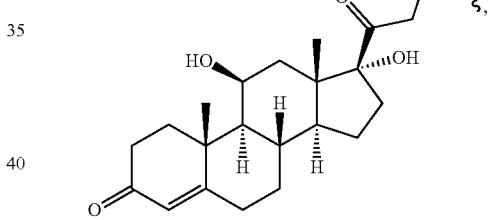
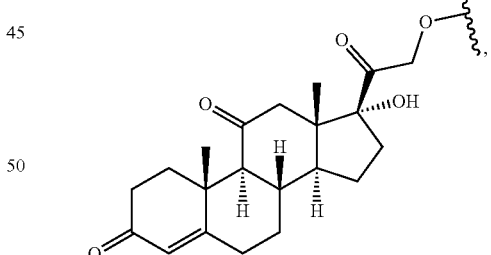
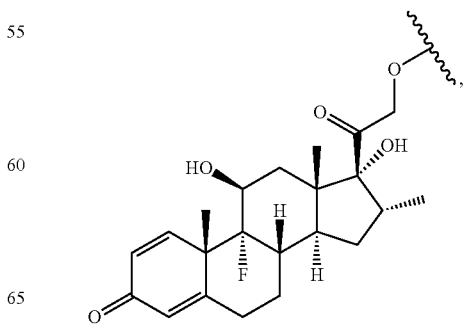

-continued
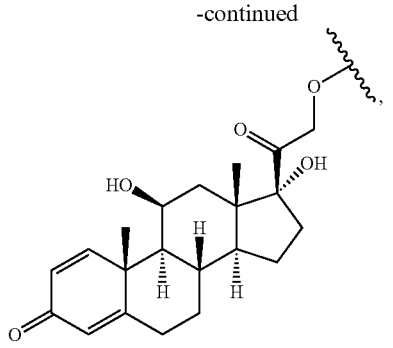
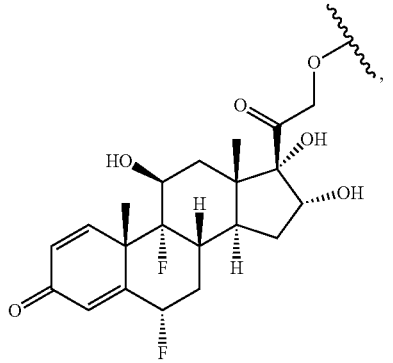
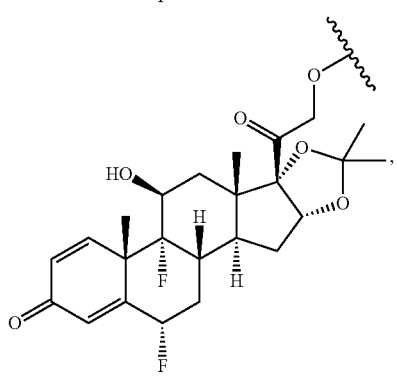
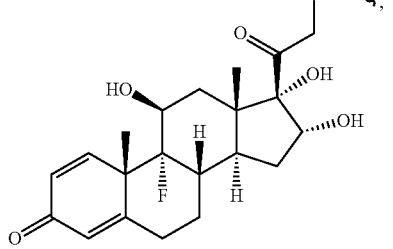, or
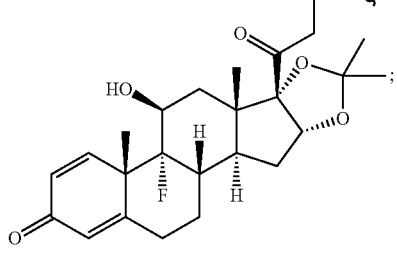;
$R^{10}$ is
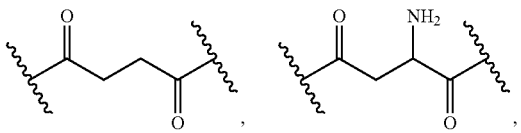,
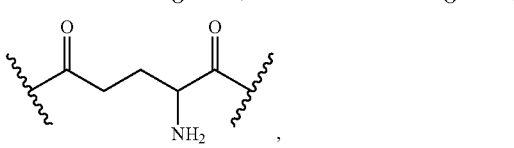,
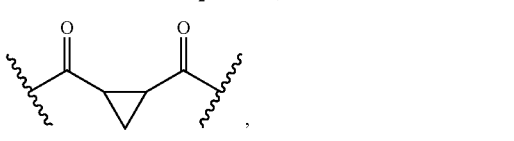,
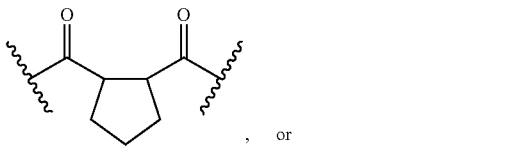, or
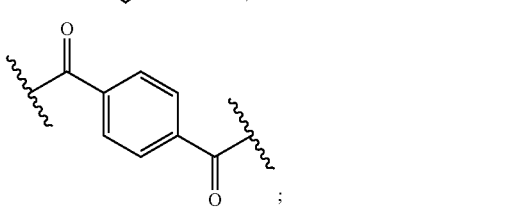;
and
$R^{11}$ is
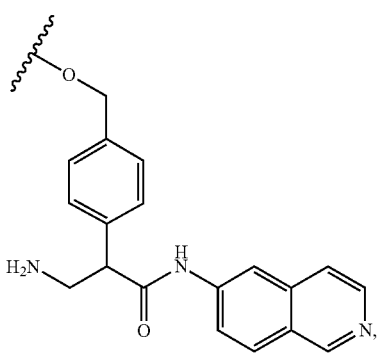,
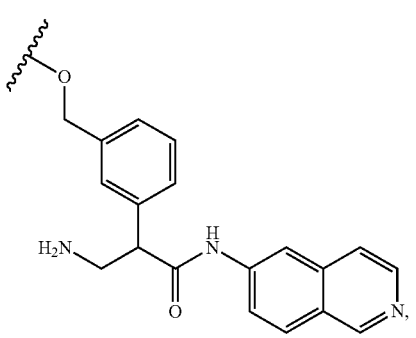, -continued
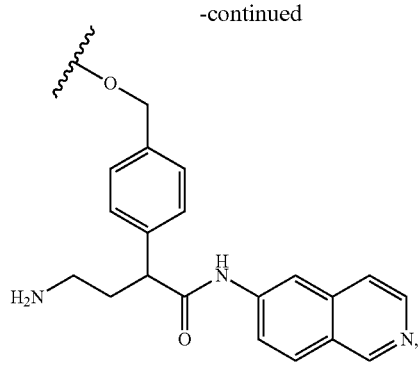
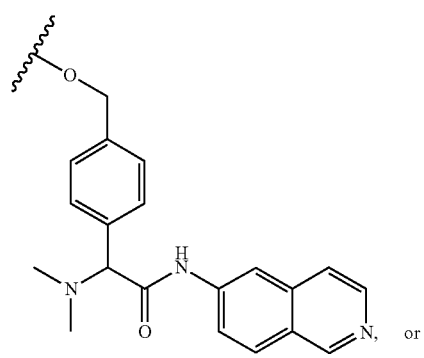
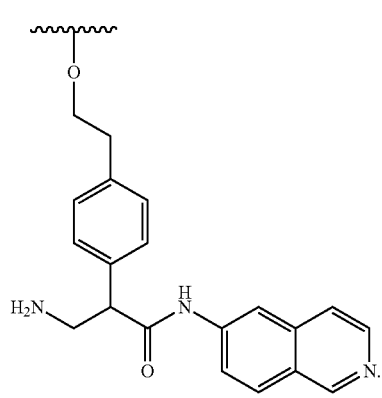 [SMILES: *OCCc1ccc([C@@H](CN)C(=O)Nc2ccc3cnccc3c2)cc1]
8. A compound having the formula:
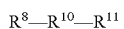
or a pharmaceutically acceptable salt thereof, wherein
$R^8$ is
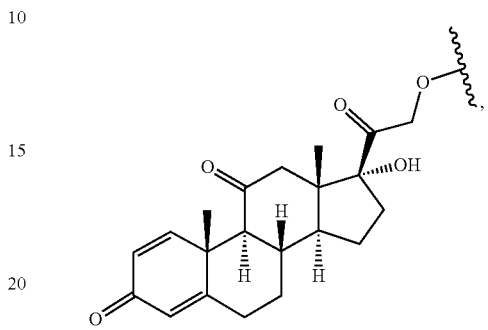
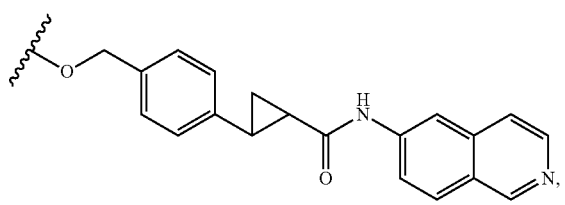
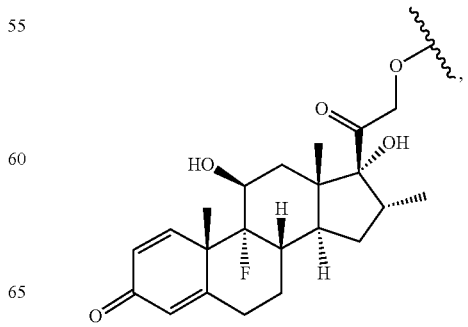

-continued
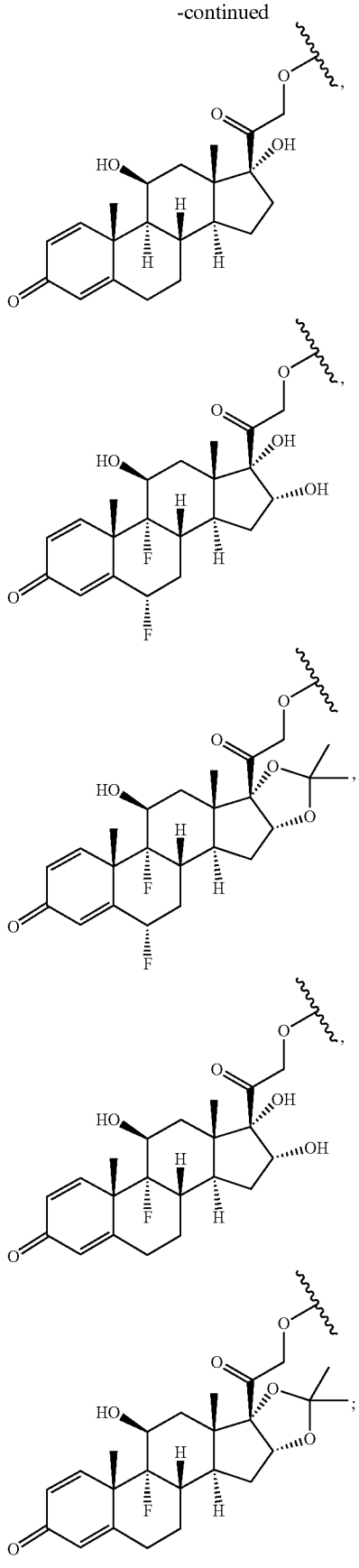
or
$R^{10}$ is
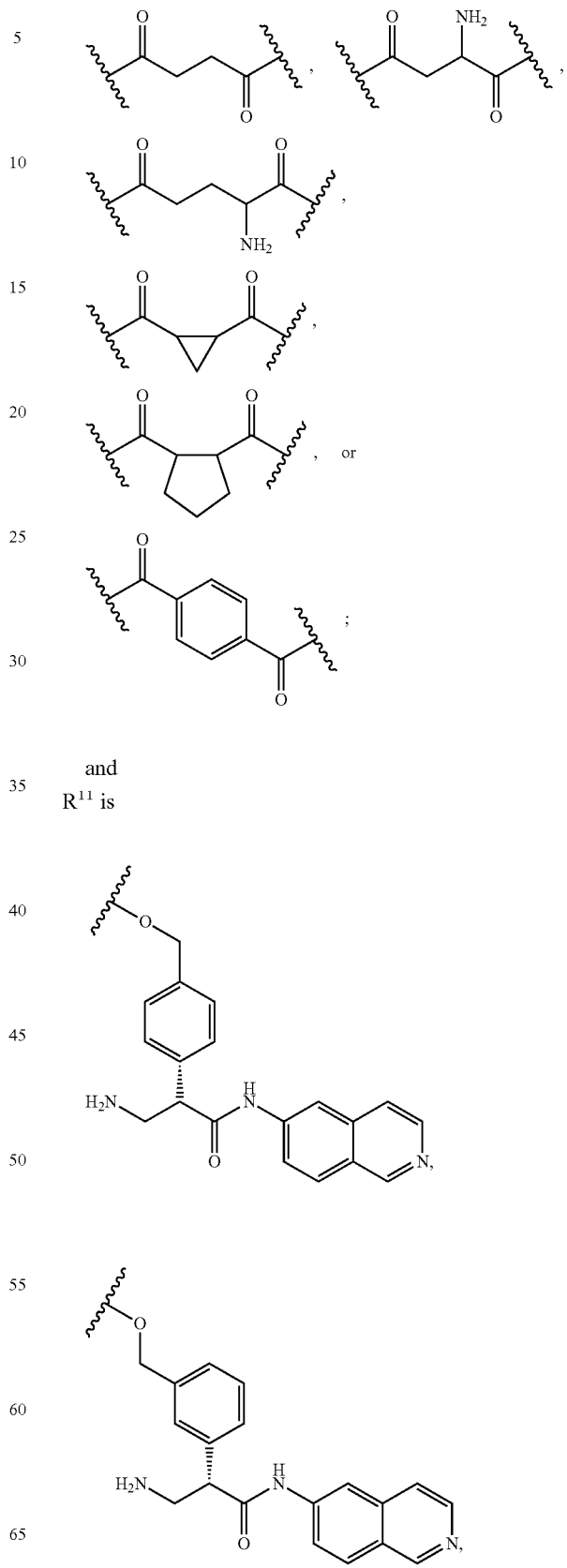
and
$R^{11}$ is

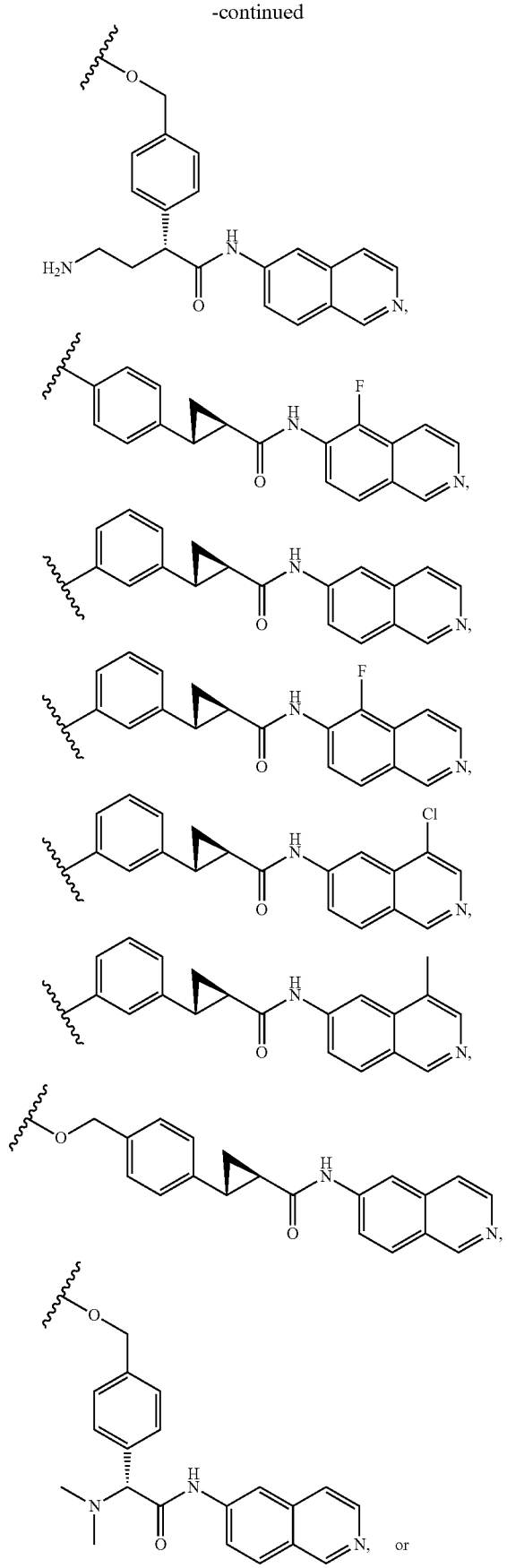
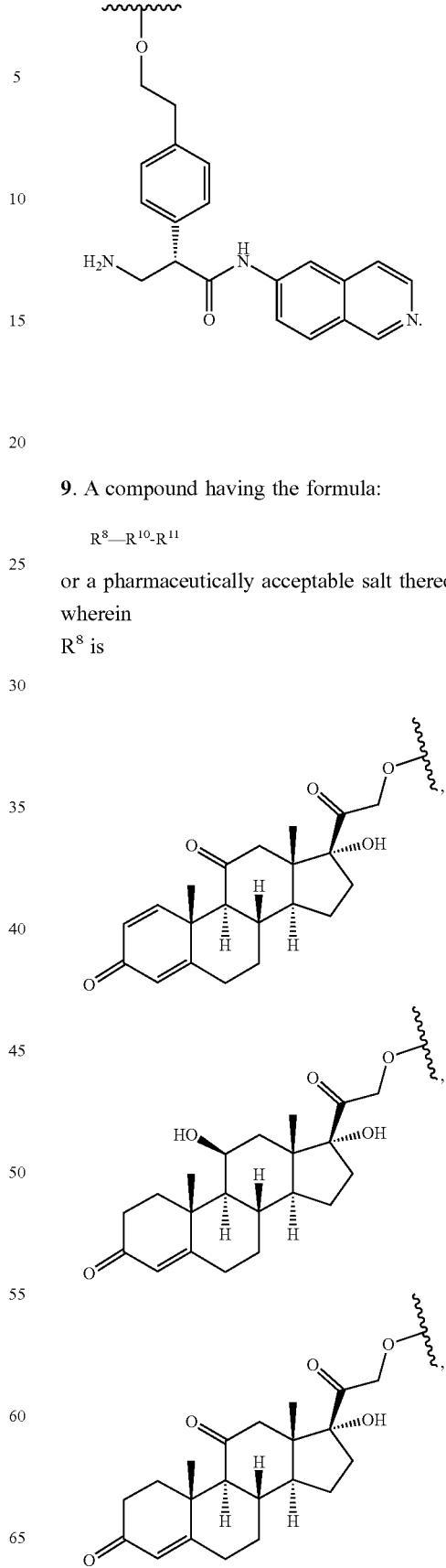
9. A compound having the formula:
$$R^8\text{—}R^{10}\text{-}R^{11}$$
or a pharmaceutically acceptable salt thereof, wherein
$R^8$ is

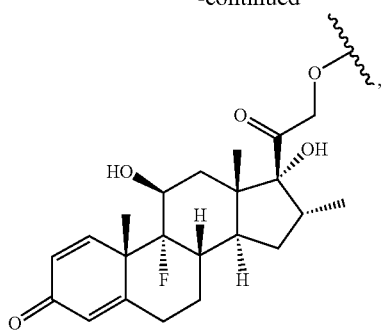
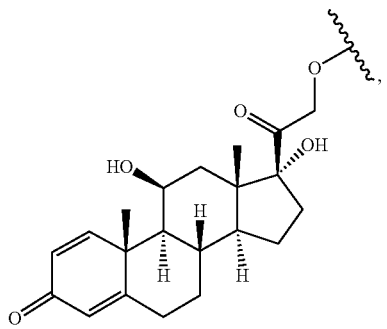
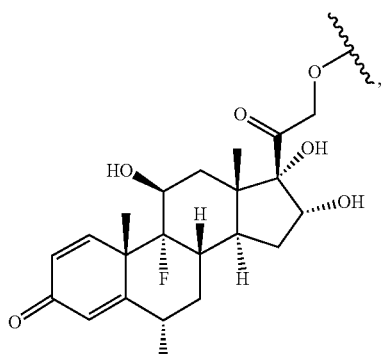
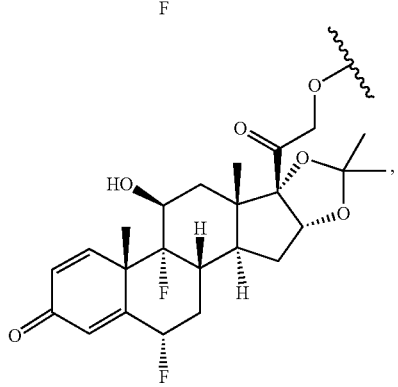
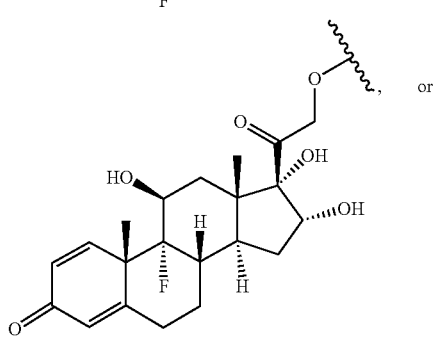
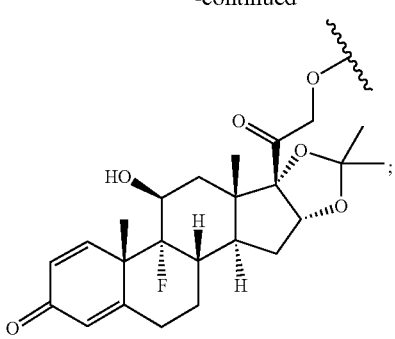
R¹⁰ is
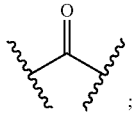
;
and
R¹¹ is
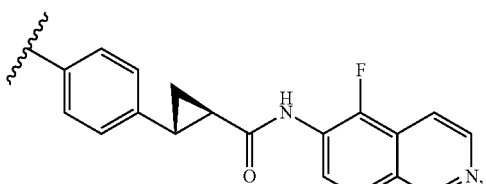
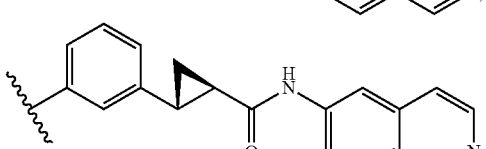
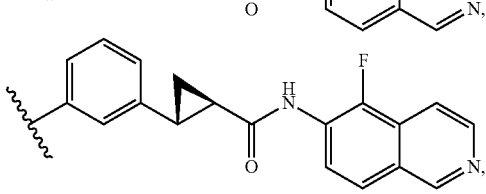
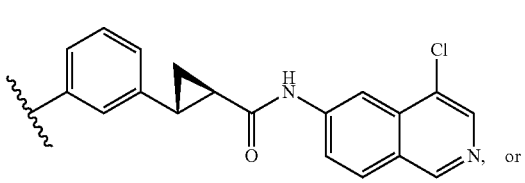
or
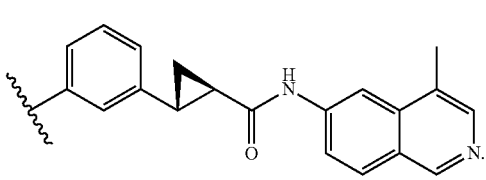

10. A compound having the formula:
$$R^8-R^{10}-R^{11}$$
or a pharmaceutically acceptable salt thereof, wherein
$R^8$ is
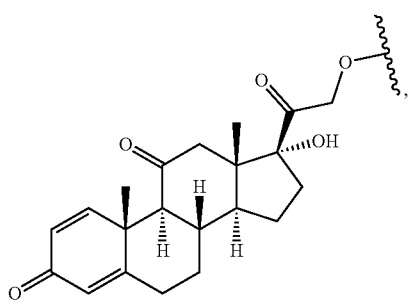
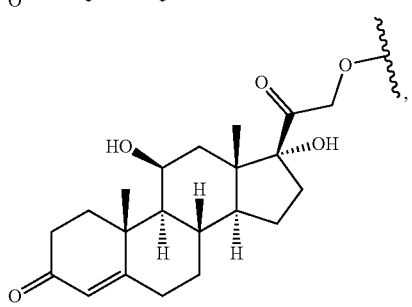
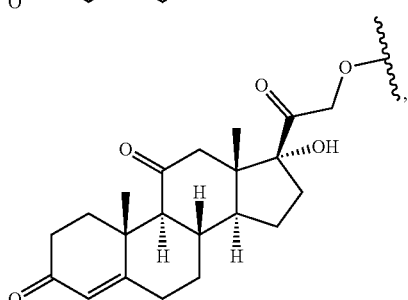
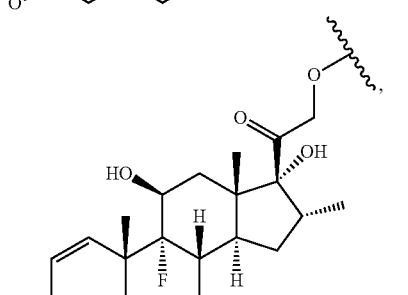
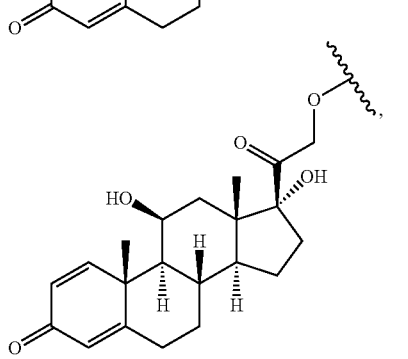
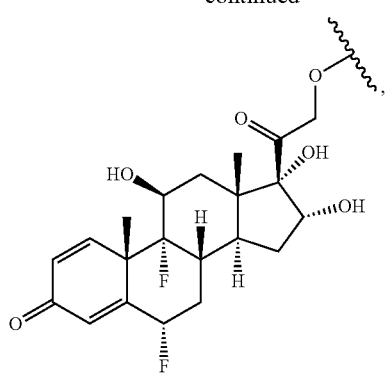
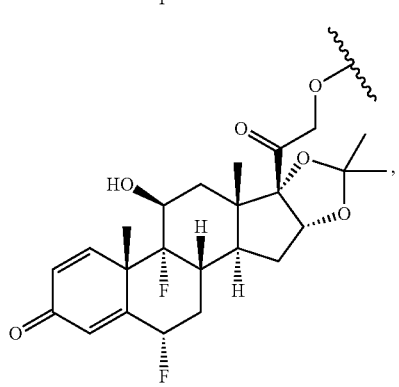
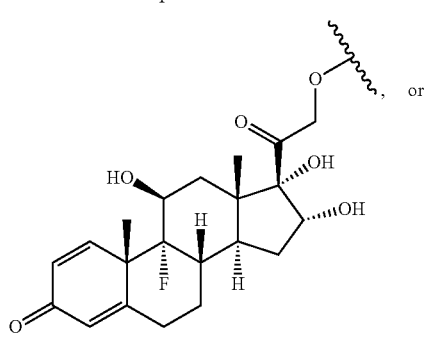
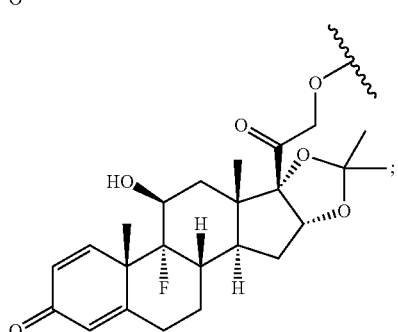
$R^{10}$ is
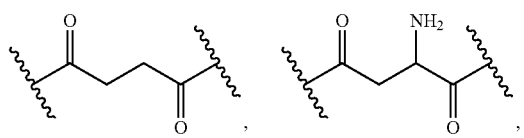

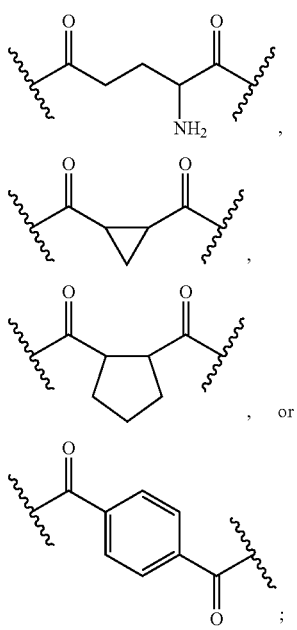

, or and
R[11] is

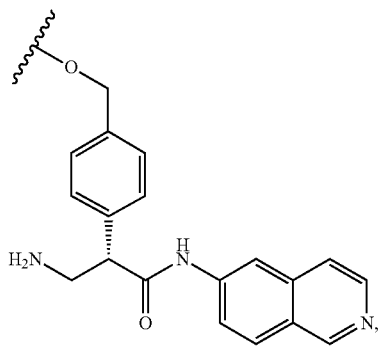

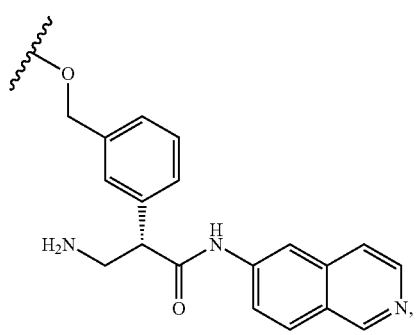

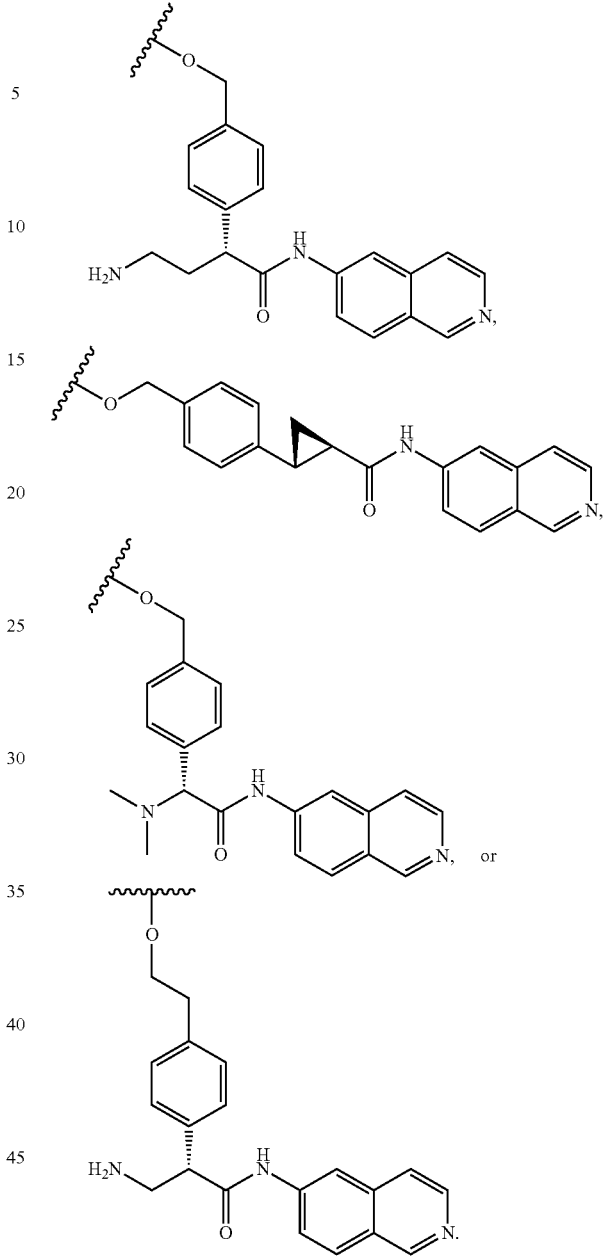

11. A composition, comprising the compound of claim 1.
12. A composition, comprising the compound of claim 2.
13. A composition, comprising the compound of claim 3.
14. A composition, comprising the compound of claim 4.
15. A composition, comprising the compound of claim 5.
16. A composition, comprising the compound of claim 6.
17. A composition, comprising the compound of claim 7.
18. A composition, comprising the compound of claim 8.
19. A composition, comprising the compound of claim 9.
20. A composition, comprising the compound of claim 10.
21. A pharmaceutical composition, comprising the compound of claim 1, and a pharmaceutically acceptable carrier.
22. A pharmaceutical composition, comprising the compound of claim 2, and a pharmaceutically acceptable carrier.
23. A pharmaceutical composition, comprising the compound of claim 3, and a pharmaceutically acceptable carrier.
24. A pharmaceutical composition, comprising the compound of claim 4, and a pharmaceutically acceptable carrier.

25. A pharmaceutical composition, comprising the compound of claim 5, and a pharmaceutically acceptable carrier.

26. A pharmaceutical composition, comprising the compound of claim 6, and a pharmaceutically acceptable carrier.

27. A pharmaceutical composition, comprising the compound of claim 7, and a pharmaceutically acceptable carrier.

28. A pharmaceutical composition, comprising the compound of claim 8, and a pharmaceutically acceptable carrier.

29. A pharmaceutical composition, comprising the compound of claim 9, and a pharmaceutically acceptable carrier.

30. A pharmaceutical composition, comprising the compound of claim 10, and a pharmaceutically acceptable carrier.

\* \* \* \* \*

UNITED STATES PATENT AND TRADEMARK OFFICE
CERTIFICATE OF CORRECTION

| | | |
|---|---|---|
| PATENT NO. | : 11,059,789 B2 | Page 1 of 3 |
| APPLICATION NO. | : 16/557779 | |
| DATED | : July 13, 2021 | |
| INVENTOR(S) | : Mitchell A. deLong et al. | |

It is certified that error appears in the above-identified patent and that said Letters Patent is hereby corrected as shown below:

In the Claims

In Claim 1, Columns 115-116, No. #3, please replace

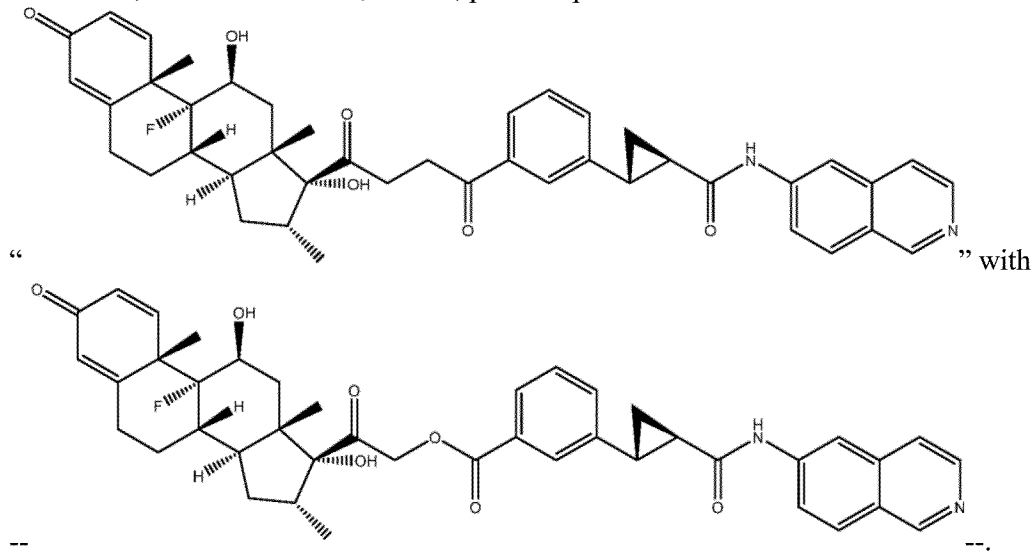

" with

" --.

Signed and Sealed this
Third Day of December, 2024

Katherine Kelly Vidal

Katherine Kelly Vidal
*Director of the United States Patent and Trademark Office*

In Claim 1, Columns 125-126, No. #3, please replace
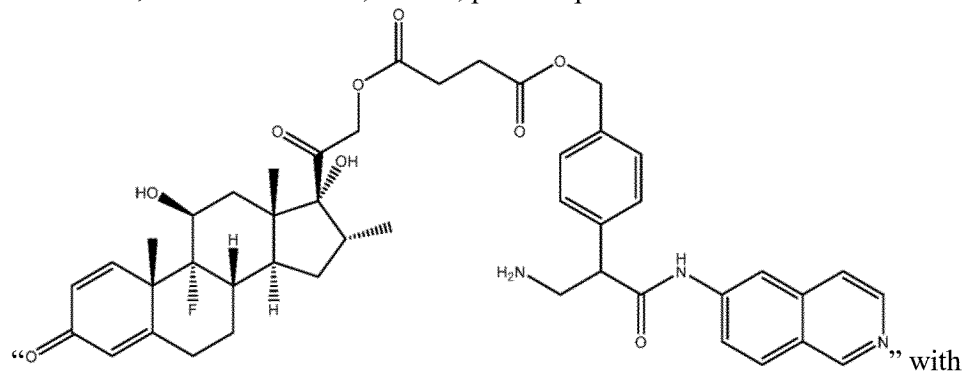 " with
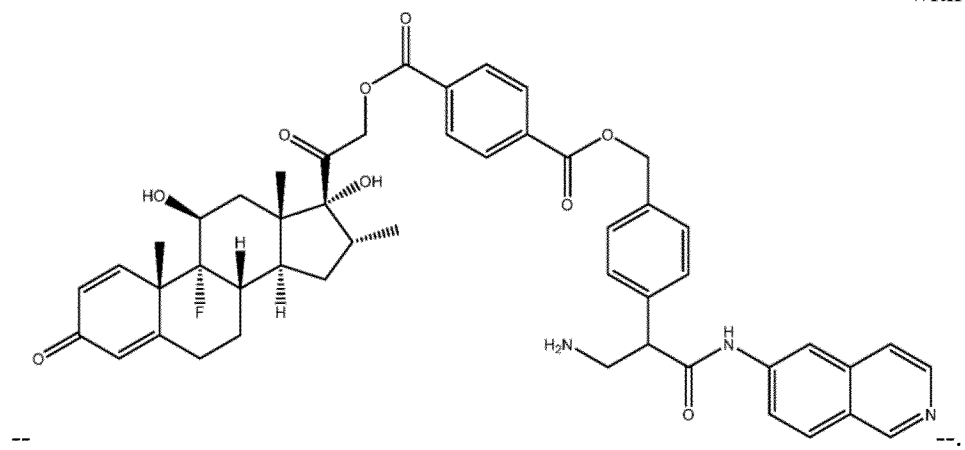 --.
In Claim 1, Columns 125-126, No. #4, please replace
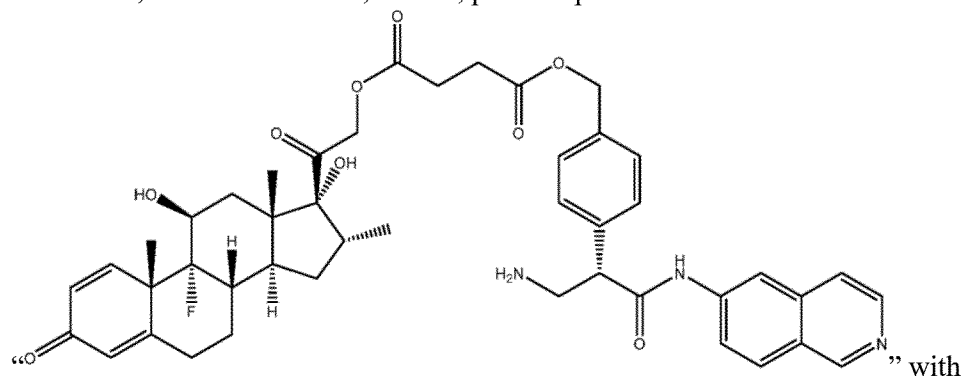 " with

CERTIFICATE OF CORRECTION (continued)

U.S. Pat. No. 11,059,789 B2

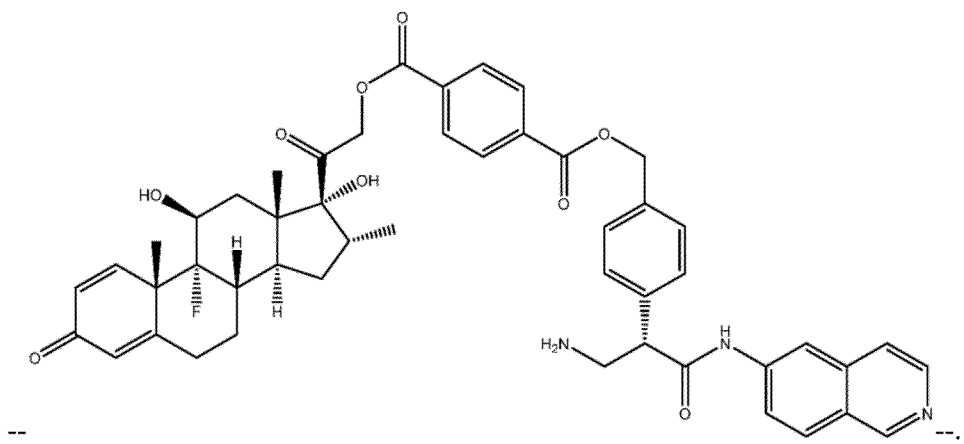
--.

In Claim 2, Column 127, Line 60, please replace " 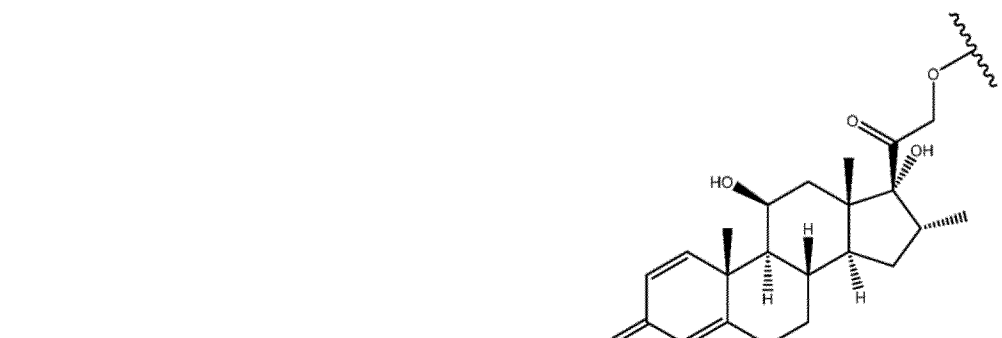 " with 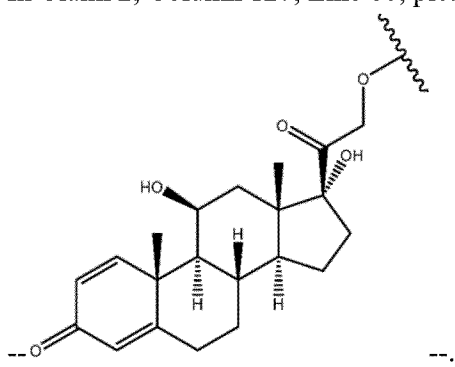 --.

In Claim 8, Column 154, Line 10, please insert -- 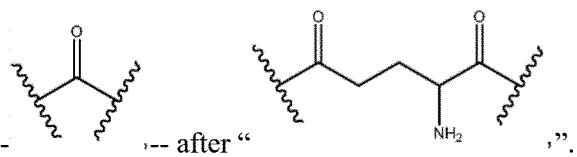 --.